US010456135B2

(12) United States Patent
Cappola

(10) Patent No.: US 10,456,135 B2
(45) Date of Patent: *Oct. 29, 2019

(54) SURGICAL INSTRUMENT

(71) Applicant: Covidien LP, Mansfield, MA (US)

(72) Inventor: Kenneth Cappola, Monroe, CT (US)

(73) Assignee: Covidien LP, Mansfield, MA (US)

( * ) Notice: Subject to any disclaimer, the term of this patent is extended or adjusted under 35 U.S.C. 154(b) by 290 days.

This patent is subject to a terminal disclaimer.

(21) Appl. No.: 15/591,215

(22) Filed: May 10, 2017

(65) Prior Publication Data

US 2017/0238930 A1 Aug. 24, 2017

Related U.S. Application Data

(60) Division of application No. 14/517,281, filed on Oct. 17, 2014, now Pat. No. 9,655,617, which is a
(Continued)

(51) Int. Cl.
*A61B 17/72* (2006.01)
*A61B 17/068* (2006.01)
(Continued)

(52) U.S. Cl.
CPC ...... *A61B 17/068* (2013.01); *A61B 17/00234* (2013.01); *A61B 17/0682* (2013.01);
(Continued)

(58) Field of Classification Search
CPC ............... A61B 17/068; A61B 17/072; A61B 17/07207; A61B 17/115;
(Continued)

(56) References Cited

U.S. PATENT DOCUMENTS 3,079,606 A    3/1963   Bobrov et al.
3,490,675 A    1/1970   Green et al.
(Continued)

FOREIGN PATENT DOCUMENTS

AU    198654765       9/1986
CA    2773414 A1     11/2012
(Continued)

OTHER PUBLICATIONS

First Examination Report issued in corresponding EP Application No. 10251794.3 dated Jul. 22, 2015.
EP Office Action for EP 10 251 7943 dated Feb. 26, 2016.

*Primary Examiner* — Scott A Smith

(57) ABSTRACT

A surgical instrument comprising a handle assembly, a body, a tool assembly and an articulation assembly is disclosed. The articulation mechanism includes a receptacle, and a main shaft. A lower clutch is fixedly positioned within the receptacle and has a serrated portion including a plurality of serrations. An upper clutch includes at least one projection positioned to engage the serrations of the lower clutch to releasably retain the main shaft at a rotatably fixed position. An angle between a first pair of adjacent serrations is defined as a first angle, an angle between a second pair of adjacent serrations is defined as a second angle, and an angle between a third pair of adjacent serrations is defined as a third angle. The first angle, the second angle, and the third angle are each different from one another.

9 Claims, 49 Drawing Sheets

Related U.S. Application Data continuation of application No. 14/062,447, filed on Oct. 24, 2013, now Pat. No. 8,888,814, which is a continuation of application No. 13/788,579, filed on Mar. 7, 2013, now Pat. No. 8,573,460, which is a continuation of application No. 13/542,690, filed on Jul. 6, 2012, now Pat. No. 8,413,868, which is a continuation of application No. 13/273,670, filed on Oct. 14, 2011, now Pat. No. 8,235,274, which is a continuation of application No. 12/580,371, filed on Oct. 16, 2009, now Pat. No. 8,061,576, which is a continuation-in-part of application No. 12/200,004, filed on Aug. 28, 2008, now Pat. No. 7,624,902.

(60) Provisional application No. 60/697,169, filed on Aug. 31, 2007.

(51) Int. Cl.
*A61B 17/072* (2006.01)
*A61B 17/00* (2006.01)
*A61B 17/29* (2006.01)

(52) U.S. Cl.
CPC ...... *A61B 17/072* (2013.01); *A61B 17/07207* (2013.01); *A61B 2017/00367* (2013.01); *A61B 2017/00473* (2013.01); *A61B 2017/07214* (2013.01); *A61B 2017/07285* (2013.01); *A61B 2017/2927* (2013.01)

(58) Field of Classification Search
CPC ........... A61B 2017/07214; A61B 2017/07271; A61B 2017/07285; A61B 17/00234; A61B 2017/00473; A61B 2017/2927
USPC .............. 227/19, 175.1, 175.2, 176.1, 180.1; 606/139, 153, 213, 219
See application file for complete search history.

(56) References Cited

U.S. PATENT DOCUMENTS

| | | |
|---|---|---|
| 3,499,591 A | 3/1970 | Green |
| 3,525,272 A * | 8/1970 | Olson ............... G05G 5/06 74/471 R |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |

(56) References Cited

U.S. PATENT DOCUMENTS

| | | |
|---|---|---|
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,855,311 A | 1/1999 | Hamblin et al. |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |

(56) References Cited

U.S. PATENT DOCUMENTS

| | | |
|---|---|---|
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |

(56) References Cited

U.S. PATENT DOCUMENTS

| | | |
|---|---|---|
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |

(56) References Cited

U.S. PATENT DOCUMENTS

| | | |
|---|---|---|
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,576 B2 | 11/2011 | Cappola |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess |
| 8,193,044 B2 | 6/2012 | Kenneth |

(56) References Cited

U.S. PATENT DOCUMENTS

| | | |
|---|---|---|
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |

(56) References Cited

U.S. PATENT DOCUMENTS

| | | |
|---|---|---|
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,460 B2 | 11/2013 | Cappola |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,888,814 B2 | 11/2014 | Cappola |
| 9,655,617 B2 * | 5/2017 | Cappola ............... A61B 17/072 |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0006434 A1 | 1/2005 | Wales et al. |
| 2005/0103819 A1 | 5/2005 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |

(56) References Cited

U.S. PATENT DOCUMENTS

| | | |
|---|---|---|
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277949 A1 | 11/2009 | Viola et al. |
| 2009/0283568 A1 | 11/2009 | Racenet et al. |
| 2009/0308907 A1 | 12/2009 | Nalagatla et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2010/0305552 A1 | 12/2010 | Shelton, IV et al. |
| 2011/0006099 A1 | 1/2011 | Hall et al. |
| 2011/0006101 A1 | 1/2011 | Hall et al. |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0068148 A1 | 3/2011 | Hall et al. |
| 2011/0087276 A1 | 4/2011 | Bedi et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132964 A1 | 6/2011 | Weisenburgh, II et al. |
| 2011/0139851 A1 | 6/2011 | McCuen |
| 2011/0147433 A1 | 6/2011 | Shelton, IV et al. |
| 2011/0155781 A1 | 6/2011 | Swensgard et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2012/0016362 A1 | 1/2012 | Heinrich et al. |
| 2012/0037683 A1 | 2/2012 | Lee |
| 2012/0053406 A1 | 3/2012 | Conlon et al. |
| 2012/0061446 A1 | 3/2012 | Knodel et al. |
| 2012/0061450 A1 | 3/2012 | Kostrzewski |
| 2012/0074196 A1 | 3/2012 | Shelton, IV et al. |
| 2012/0074200 A1 | 3/2012 | Schmid et al. |
| 2012/0080474 A1 | 4/2012 | Farascioni |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080481 A1 | 4/2012 | Widenhouse et al. |
| 2012/0080482 A1 | 4/2012 | Schall et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080494 A1 | 4/2012 | Thompson et al. |
| 2012/0080495 A1 | 4/2012 | Holcomb et al. |
| 2012/0080498 A1 | 4/2012 | Shelton, IV et al. |
| 2012/0080499 A1 | 4/2012 | Schall et al. |
| 2012/0080502 A1 | 4/2012 | Morgan et al. |
| 2012/0091183 A1 | 4/2012 | Manoux et al. |
| 2012/0100200 A1 | 4/2012 | Belcheva et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0223123 A1 | 9/2012 | Baxter, III et al. |
| 2012/0228358 A1 | 9/2012 | Zemlok et al. |
| 2012/0234893 A1 | 9/2012 | Schuckmann et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0239009 A1 | 9/2012 | Mollere et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241504 A1 | 9/2012 | Soltz et al. |
| 2012/0241505 A1 | 9/2012 | Alexander, III et al. |
| 2012/0248169 A1 | 10/2012 | Widenhouse et al. |
| 2012/0248170 A1 | 10/2012 | Marczyk |
| 2012/0255986 A1 | 10/2012 | Petty et al. |
| 2012/0286021 A1 | 11/2012 | Kostrzewski |
| 2012/0286022 A1 | 11/2012 | Olson et al. |
| 2012/0292369 A1 | 11/2012 | Munro, III et al. |
| 2012/0298719 A1 | 11/2012 | Shelton, IV et al. |
| 2012/0298722 A1 | 11/2012 | Hess et al. |
| 2012/0312858 A1 | 12/2012 | Patankar et al. |
| 2012/0312859 A1 | 12/2012 | Gupta et al. |
| 2012/0312860 A1 | 12/2012 | Ming et al. |
| 2012/0312861 A1 | 12/2012 | Gurumurthy et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037594 A1 | 2/2013 | Dhakad et al. |
| 2013/0037595 A1 | 2/2013 | Gupta et al. |
| 2013/0037596 A1 | 2/2013 | Bear et al. |
| 2013/0037597 A1 | 2/2013 | Katre et al. |
| 2013/0037598 A1 | 2/2013 | Marczyk |
| 2013/0041406 A1 | 2/2013 | Bear et al. |
| 2013/0048697 A1 | 2/2013 | Shelton, IV et al. |
| 2013/0056518 A1 | 3/2013 | Swensgard |
| 2013/0056521 A1 | 3/2013 | Swensgard |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |

(56) References Cited

U.S. PATENT DOCUMENTS

| | | |
|---|---|---|
| 2013/0068816 A1 | 3/2013 | Mandakolathur Vasudevan et al. |
| 2013/0068818 A1 | 3/2013 | Kasvikis |
| 2013/0068821 A1 | 3/2013 | Huitema et al. |
| 2013/0075443 A1 | 3/2013 | Giordano et al. |
| 2013/0075444 A1 | 3/2013 | Cappola et al. |
| 2013/0075445 A1 | 3/2013 | Balek et al. |
| 2013/0075446 A1 | 3/2013 | Wang et al. |
| 2013/0075447 A1 | 3/2013 | Weisenburgh, II et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0075451 A1 | 3/2013 | Balek et al. |
| 2013/0082086 A1 | 4/2013 | Hueil et al. |
| 2013/0087597 A1 | 4/2013 | Shelton, IV et al. |
| 2013/0087599 A1 | 4/2013 | Krumanaker et al. |
| 2013/0087600 A1 | 4/2013 | Scirica |
| 2013/0087601 A1 | 4/2013 | Farascioni |
| 2013/0087602 A1 | 4/2013 | Olson et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0112732 A1 | 5/2013 | Aranyi et al. |
| 2013/0112733 A1 | 5/2013 | Aranyi et al. |
| 2013/0119109 A1 | 5/2013 | Farascioni et al. |
| 2013/0126581 A1 | 5/2013 | Yates et al. |
| 2013/0126582 A1 | 5/2013 | Shelton, IV et al. |
| 2013/0126586 A1 | 5/2013 | Zhang et al. |
| 2013/0140343 A1 | 6/2013 | Knodel |
| 2013/0144333 A1 | 6/2013 | Viola |

FOREIGN PATENT DOCUMENTS

| | | |
|---|---|---|
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A3 | 3/1993 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 0807409 A1 | 11/1997 |
| EP | 1 970 015 A2 | 9/2008 |
| EP | 2030577 A2 | 3/2009 |
| EP | 2090253 A2 | 8/2009 |
| EP | 2090254 A1 | 8/2009 |
| EP | 2583630 A2 | 4/2013 |
| EP | 2586382 A2 | 5/2013 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 200187272 | 4/2001 |
| SU | 659146 A1 | 4/1979 |
| SU | 728848 A1 | 4/1980 |
| SU | 980703 A1 | 12/1982 |
| SU | 990220 A1 | 1/1983 |
| WO | 8302247 A1 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004032760 A2 | 4/2004 |
| WO | 2009071070 A2 | 6/2009 |

\* cited by examiner

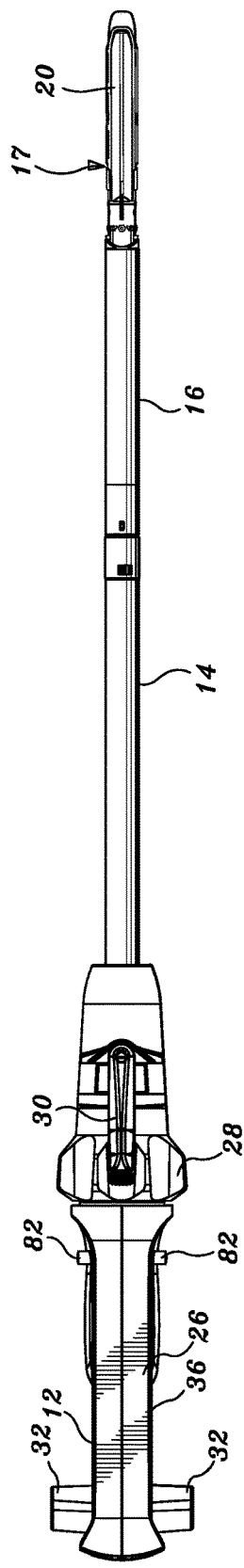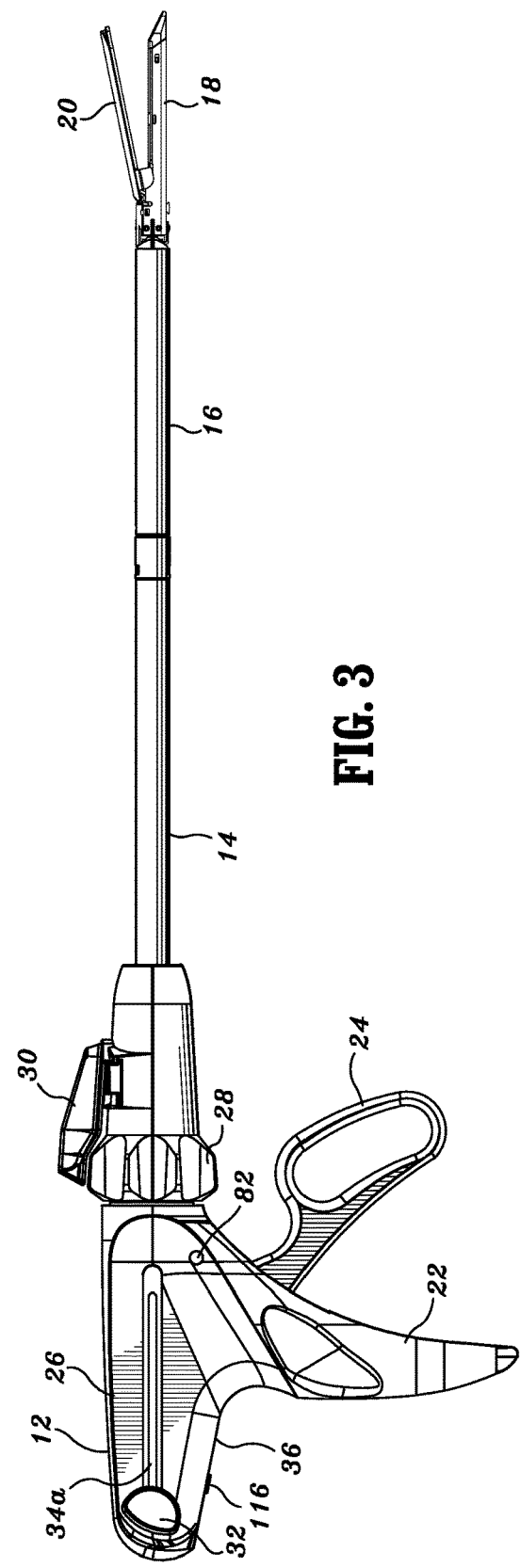
FIG. 2
FIG. 3

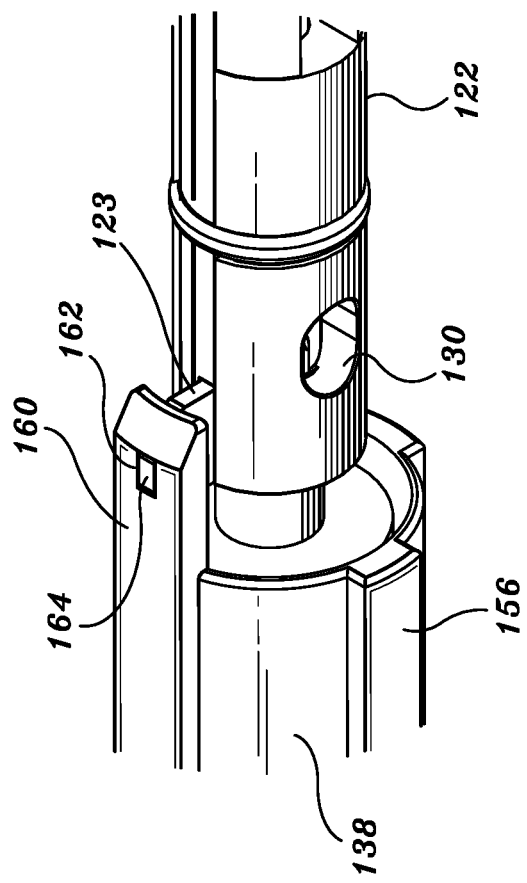

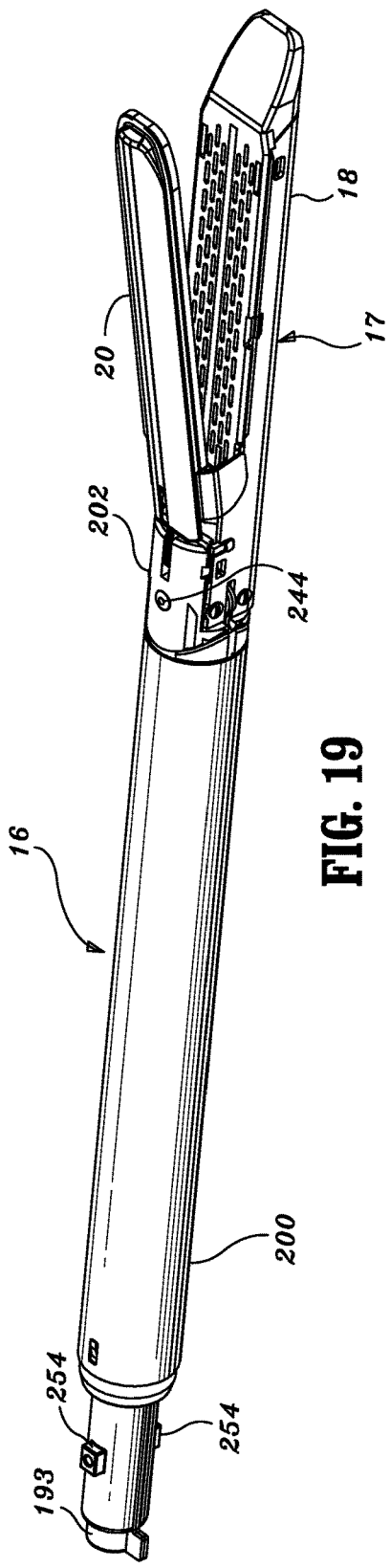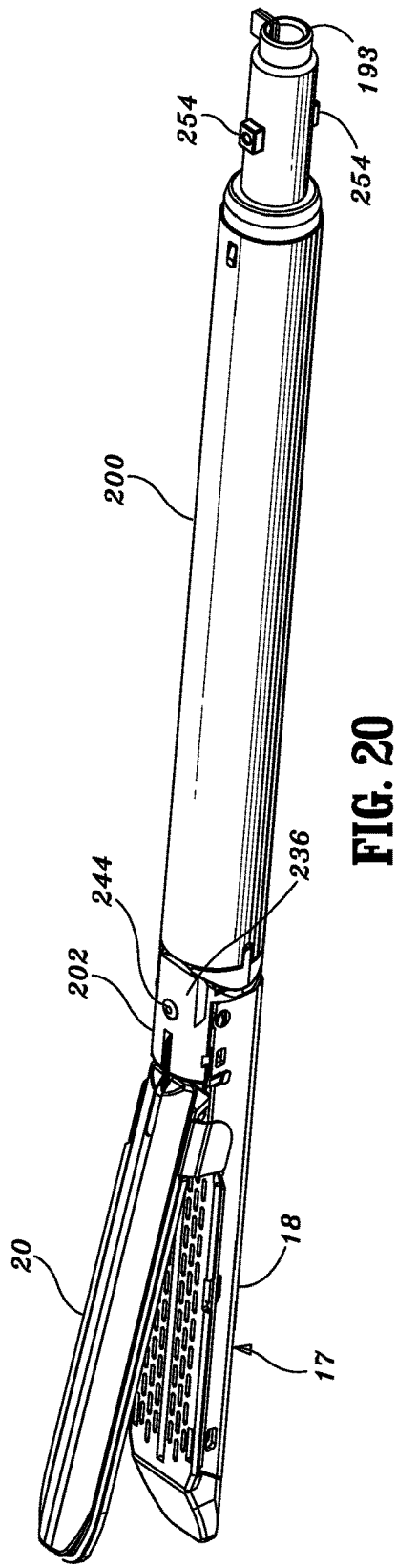

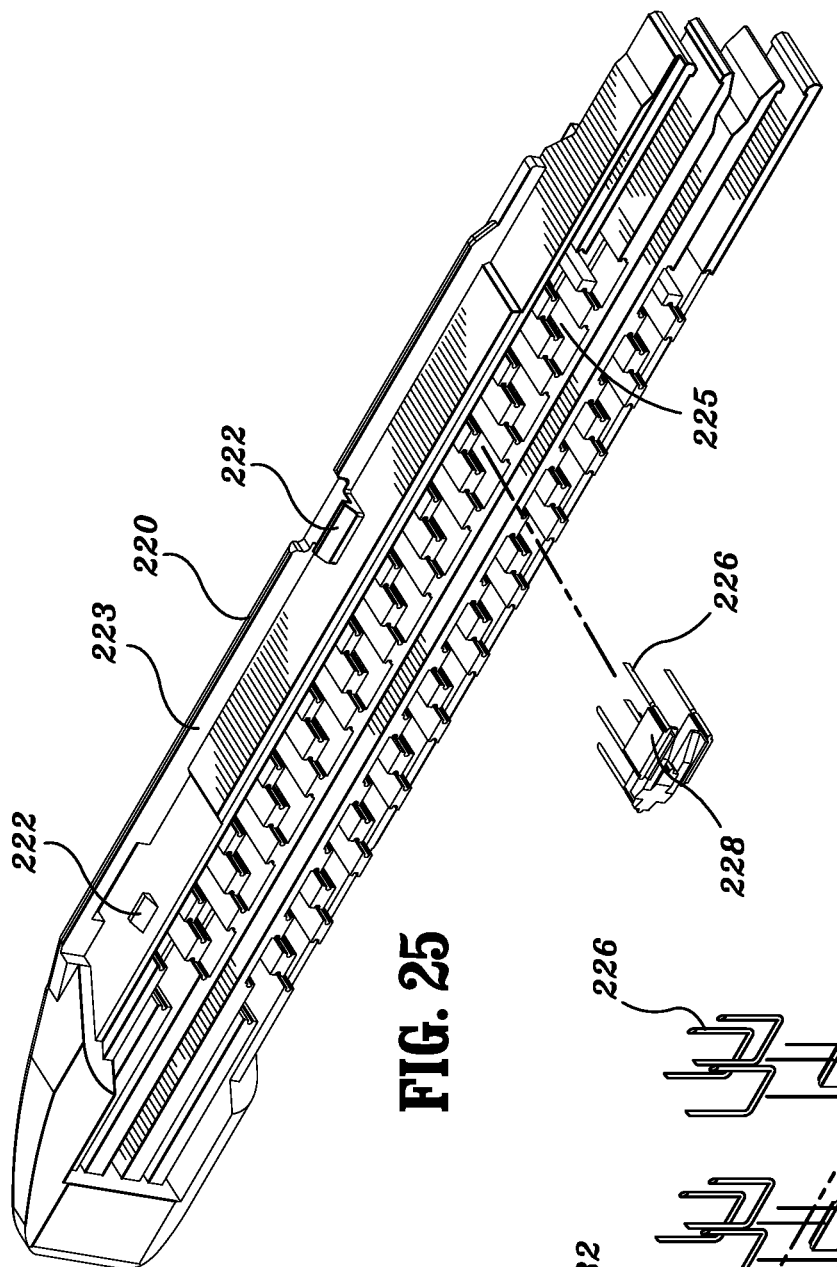
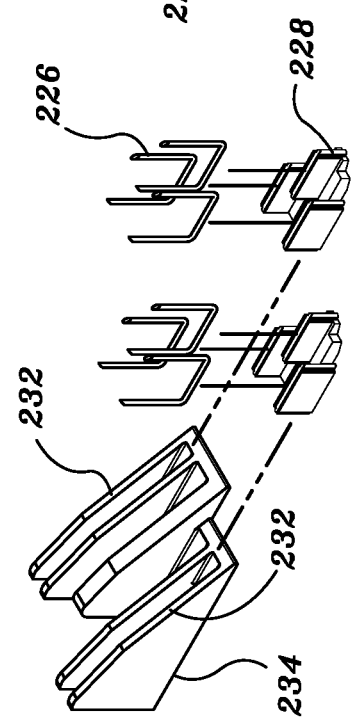
FIG. 25
FIG. 26

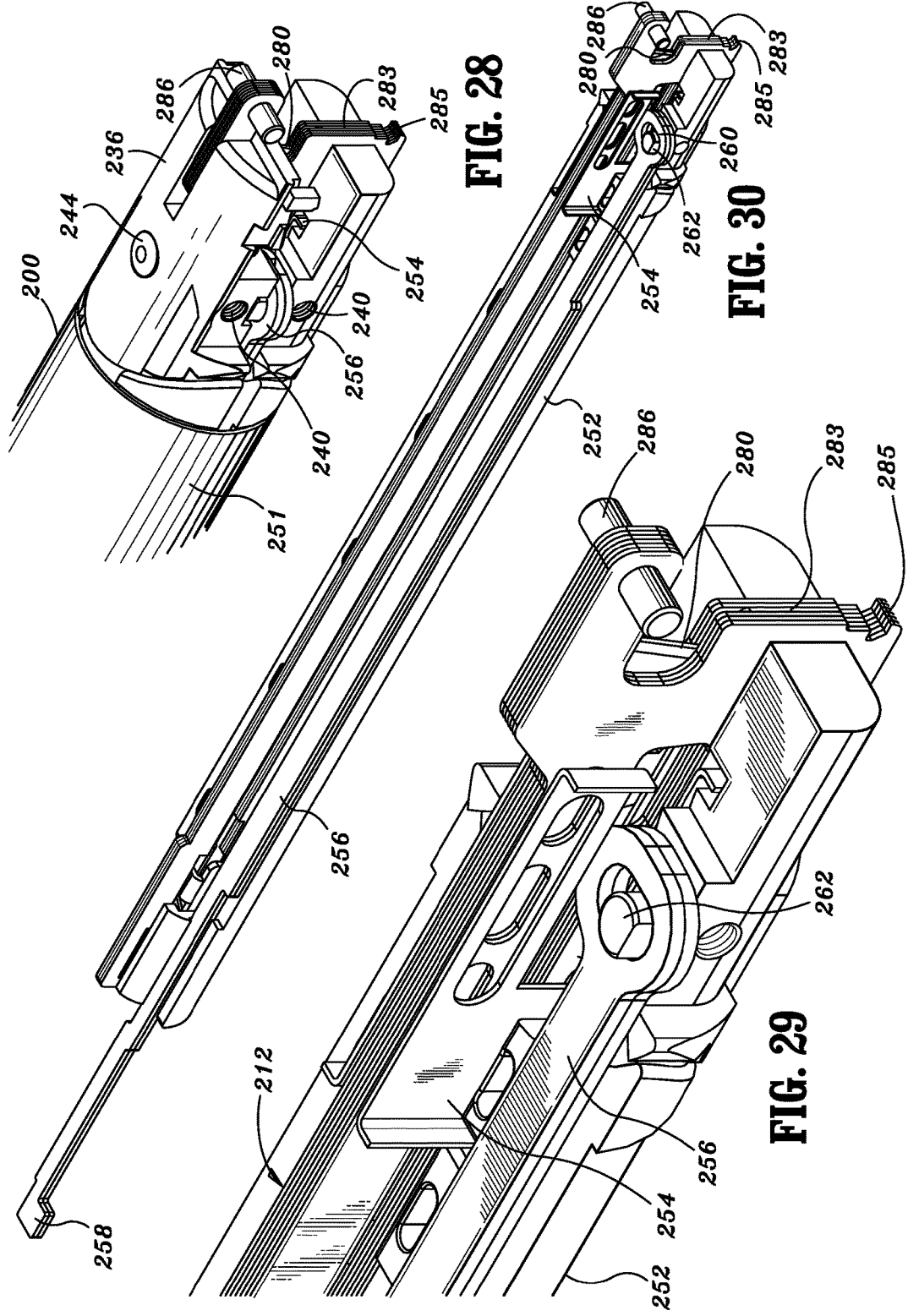

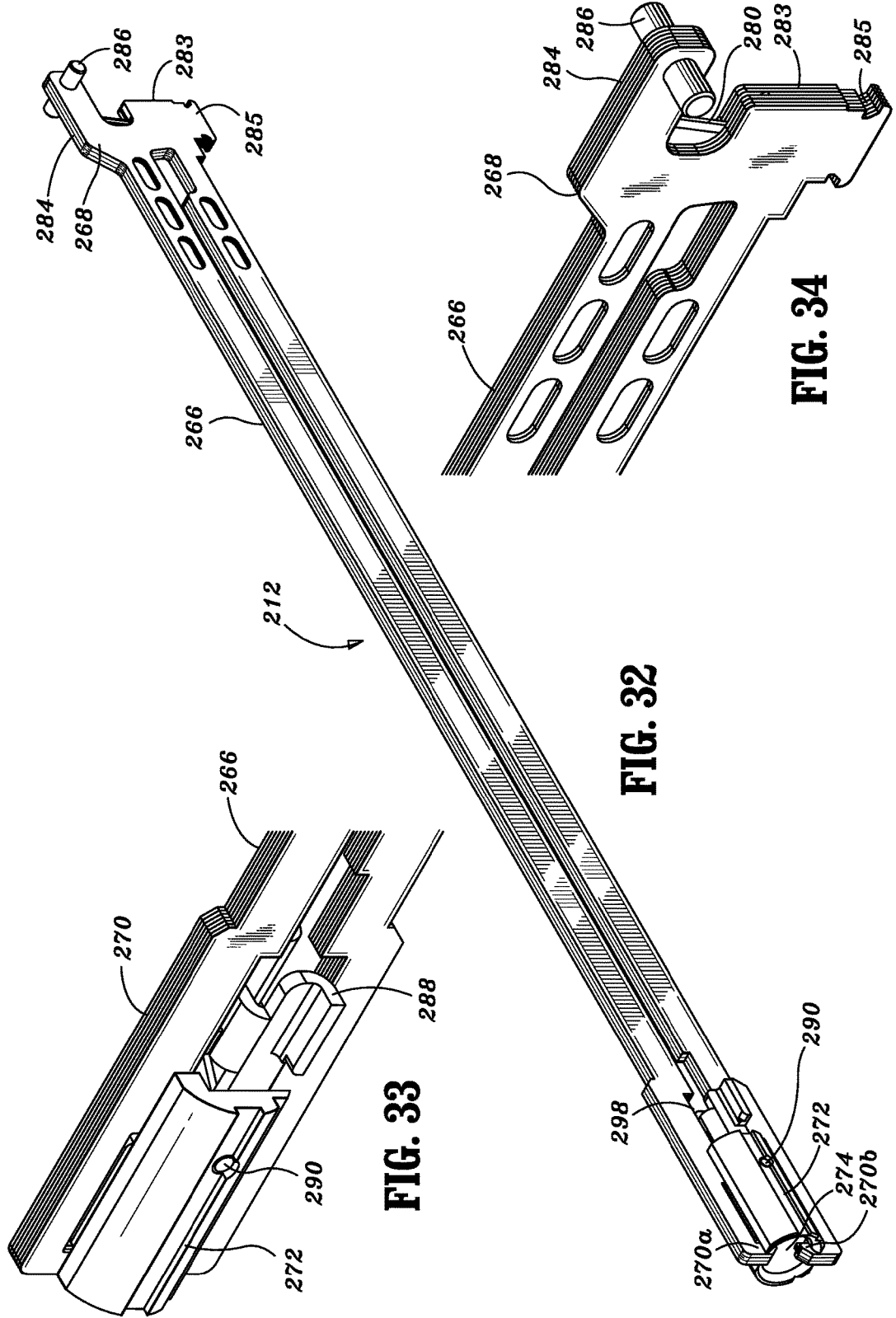

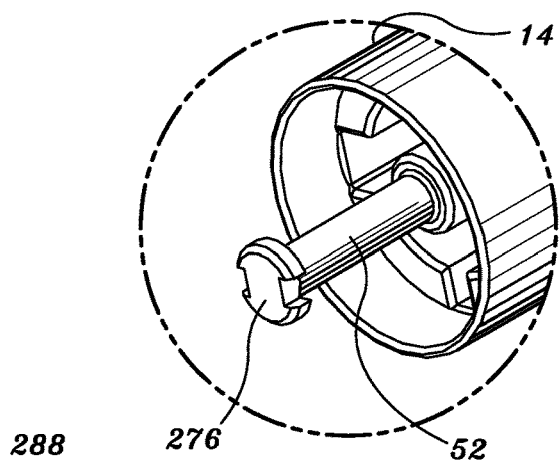
FIG. 35
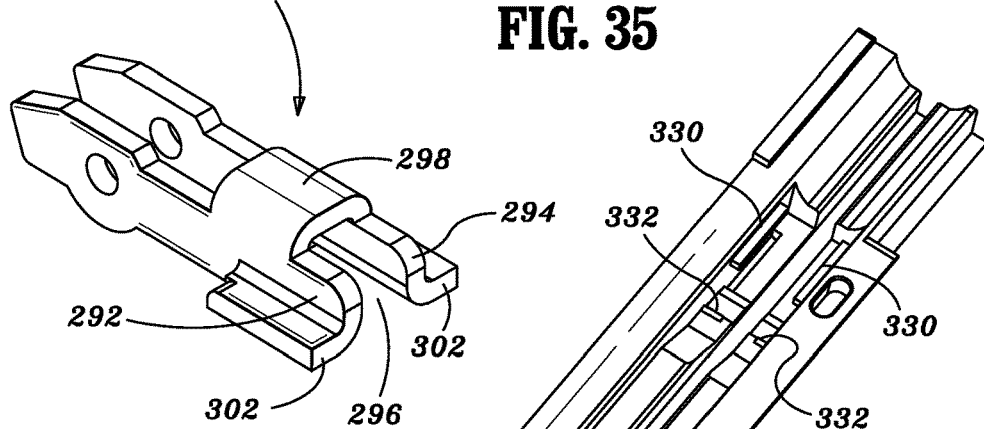
FIG. 36
FIG. 37

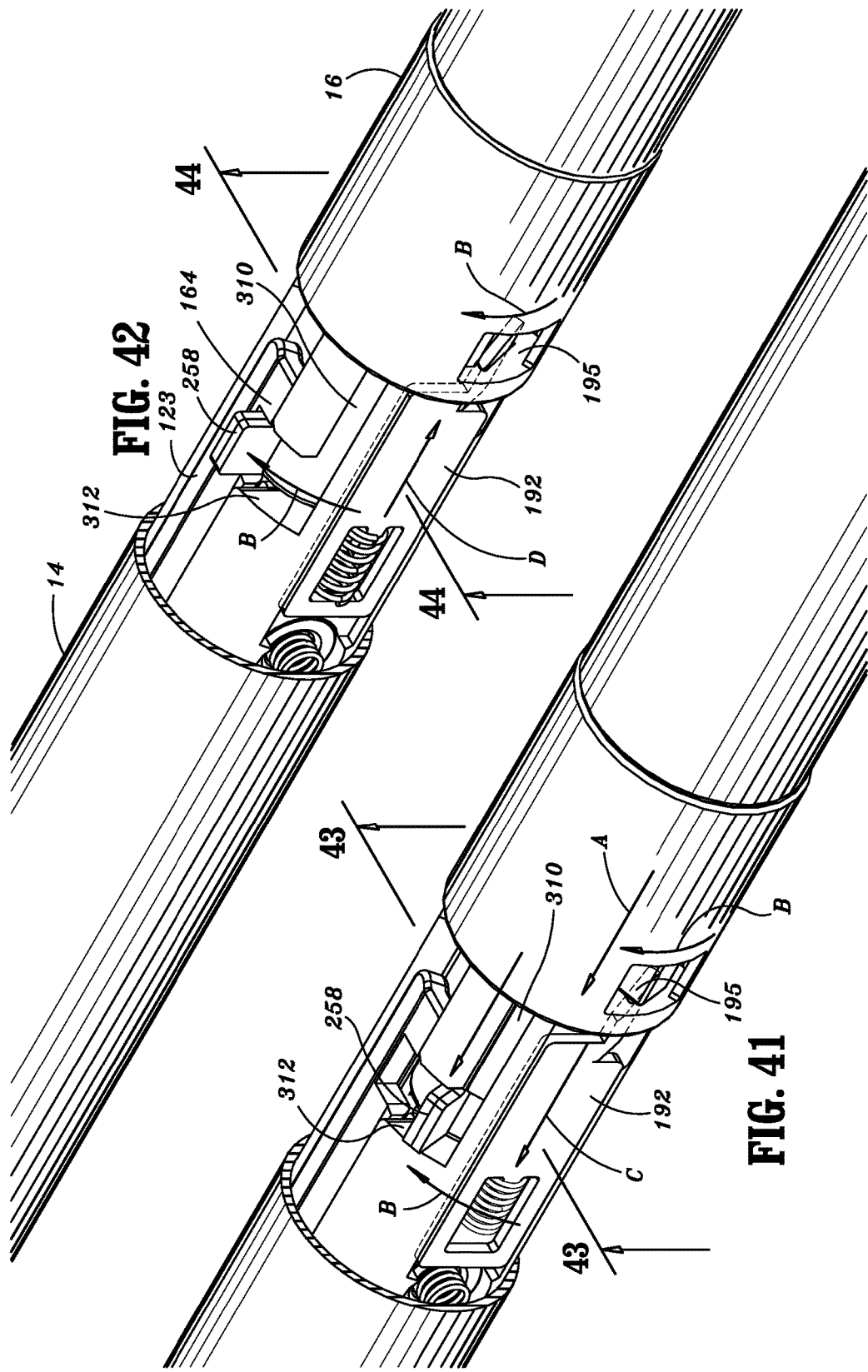

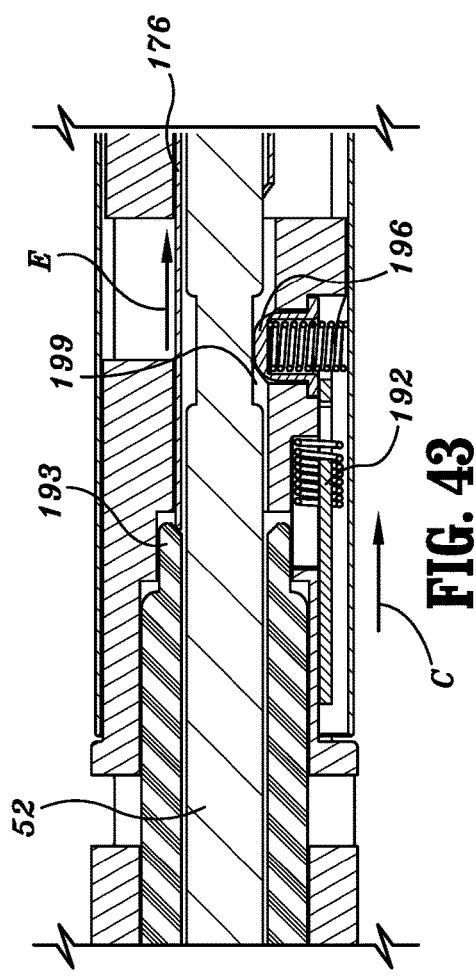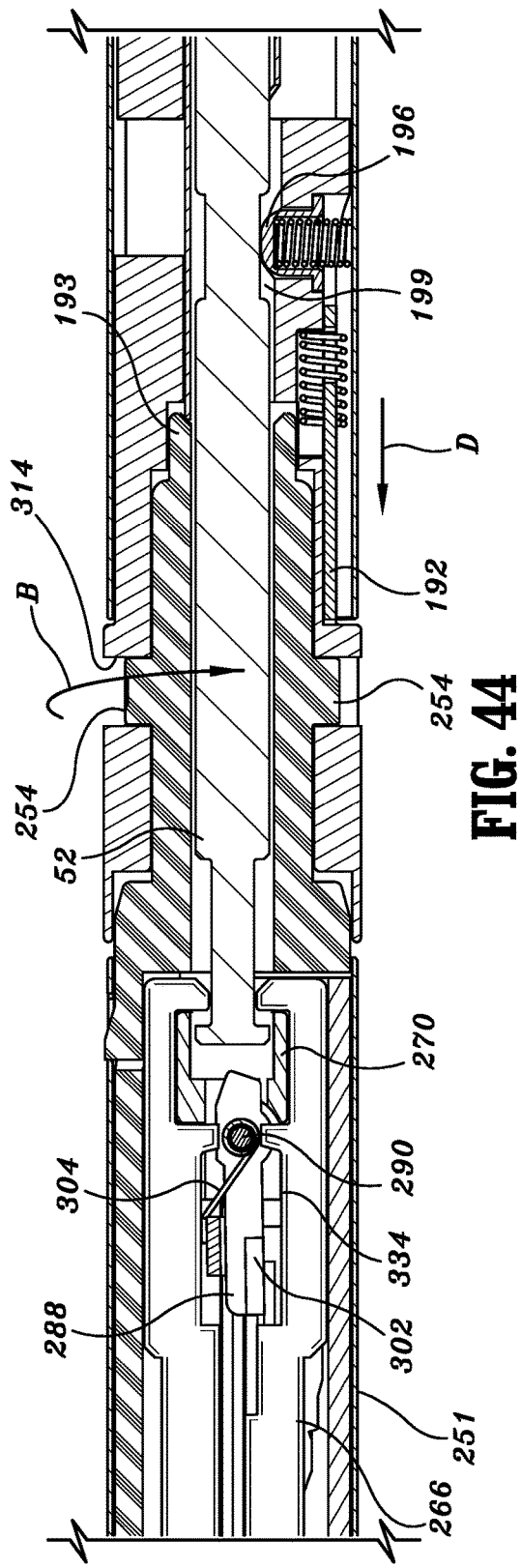
FIG. 43
FIG. 44

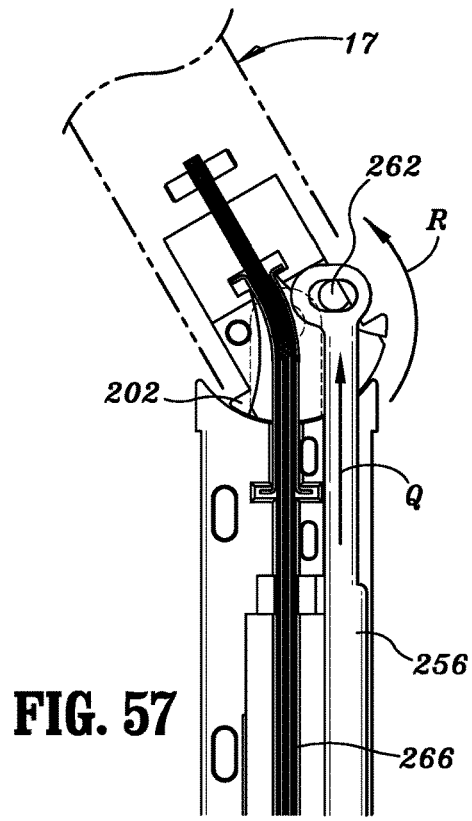
FIG. 57
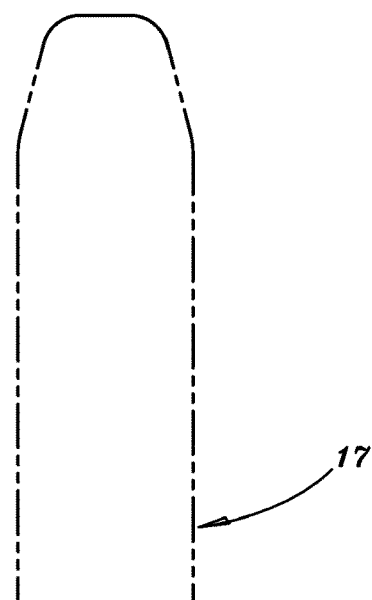
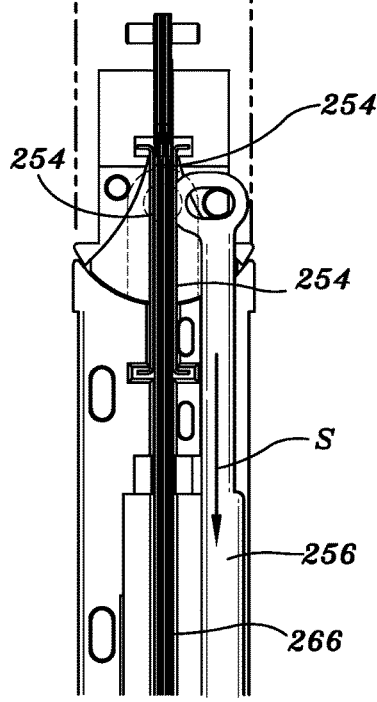
FIG. 60
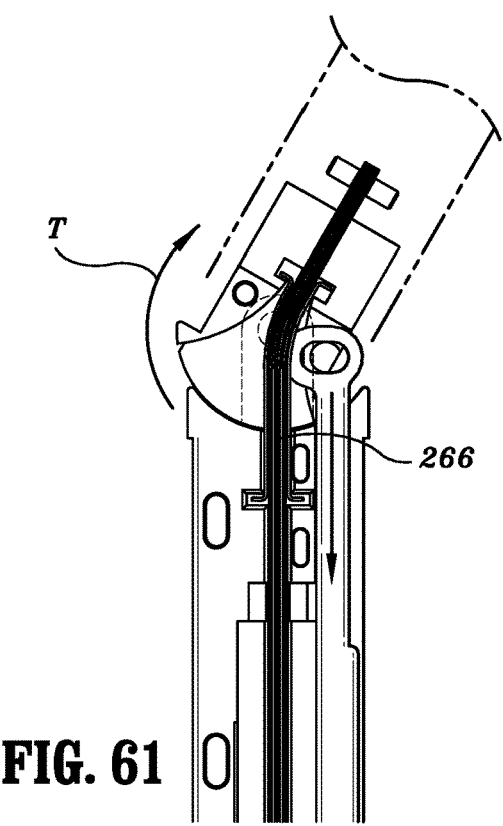
FIG. 61

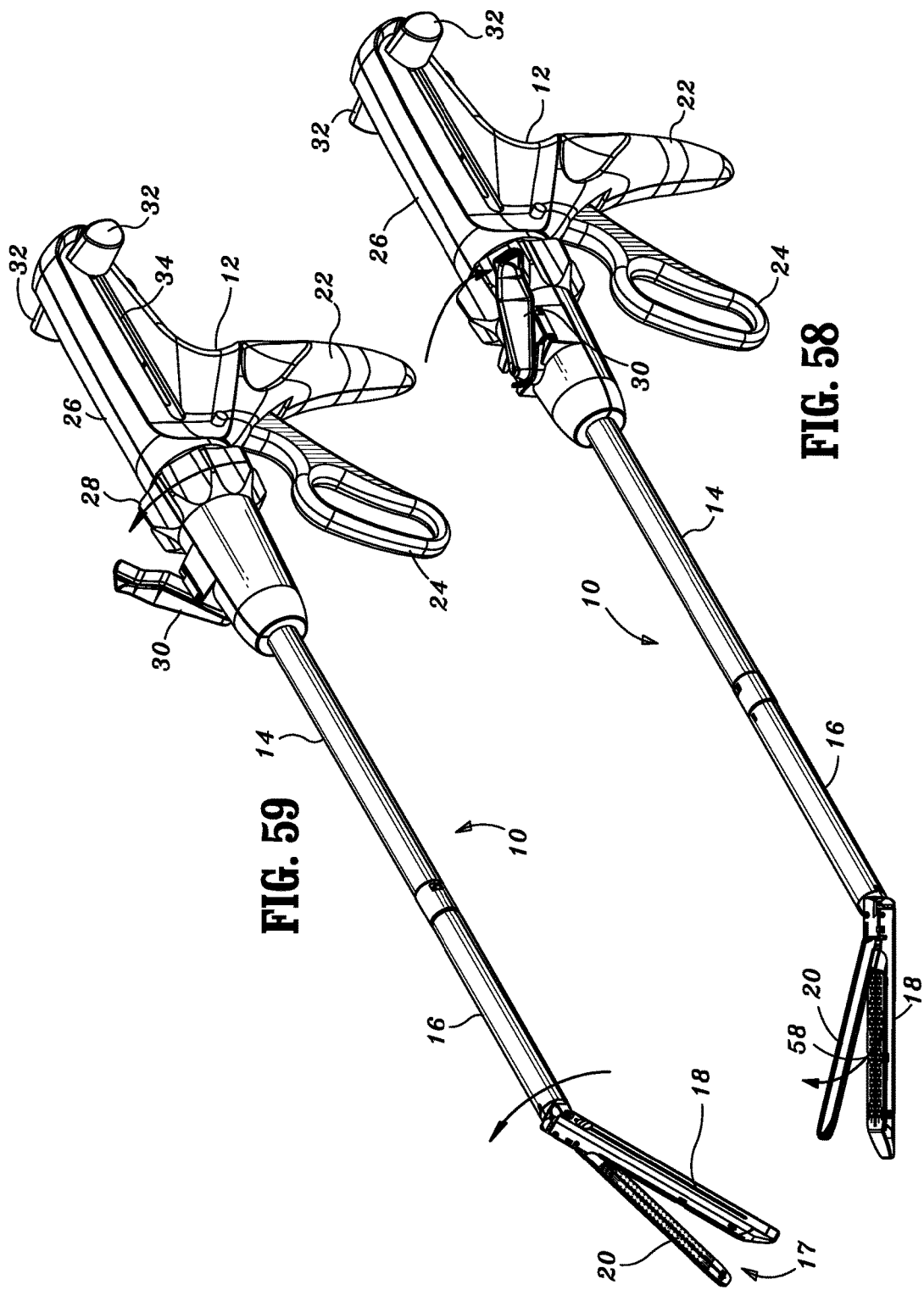

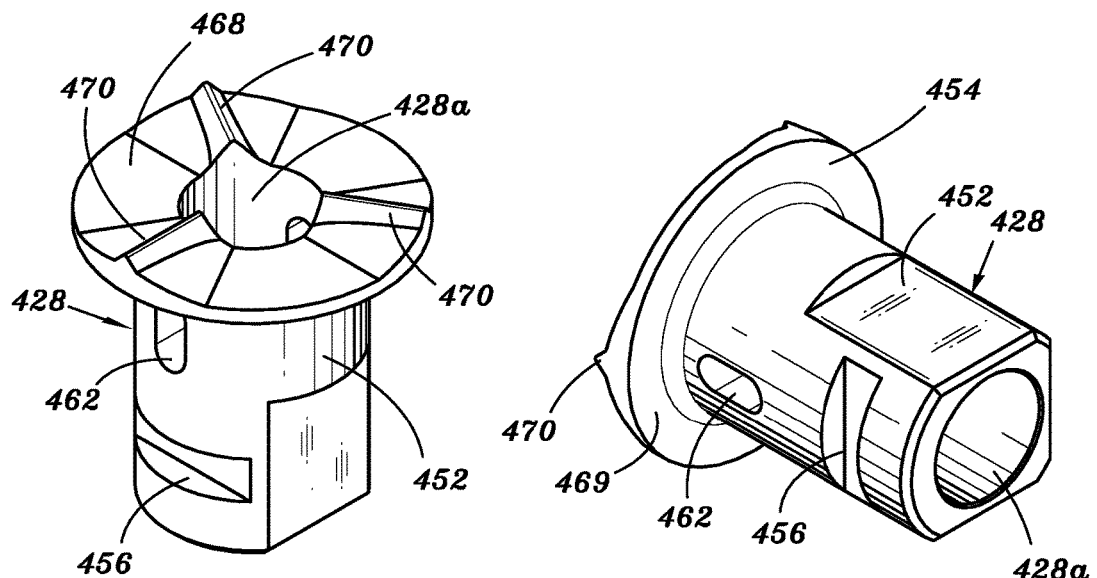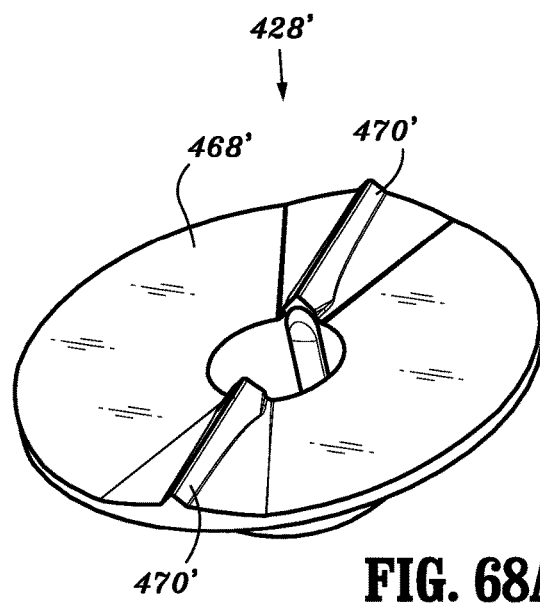

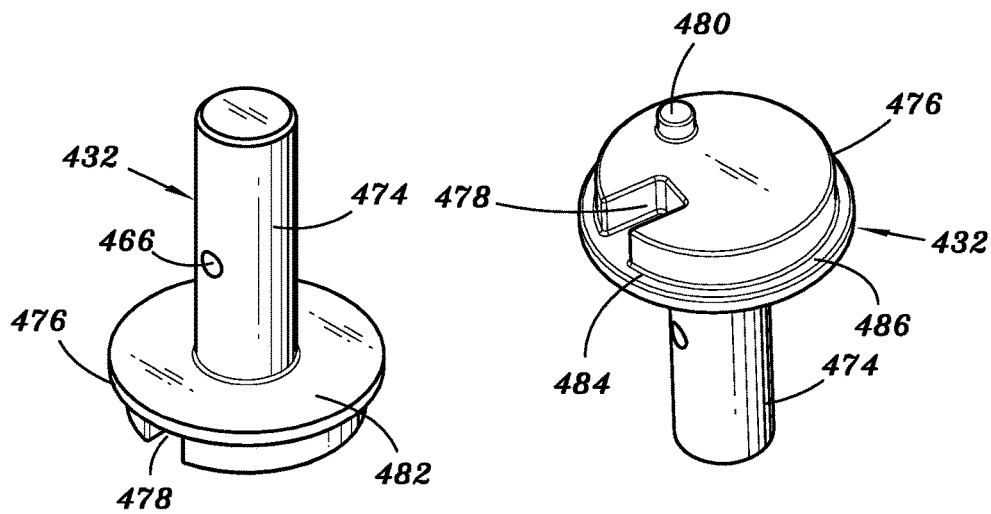
FIG. 71  FIG. 72
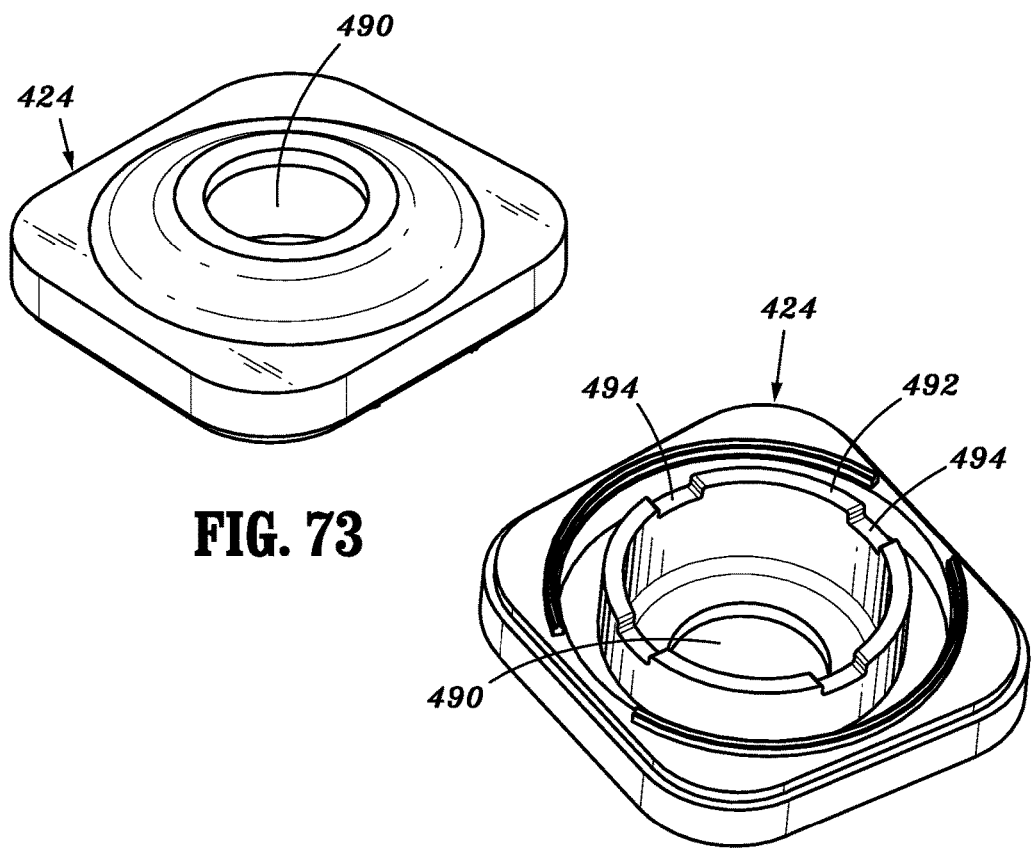
FIG. 73
FIG. 74

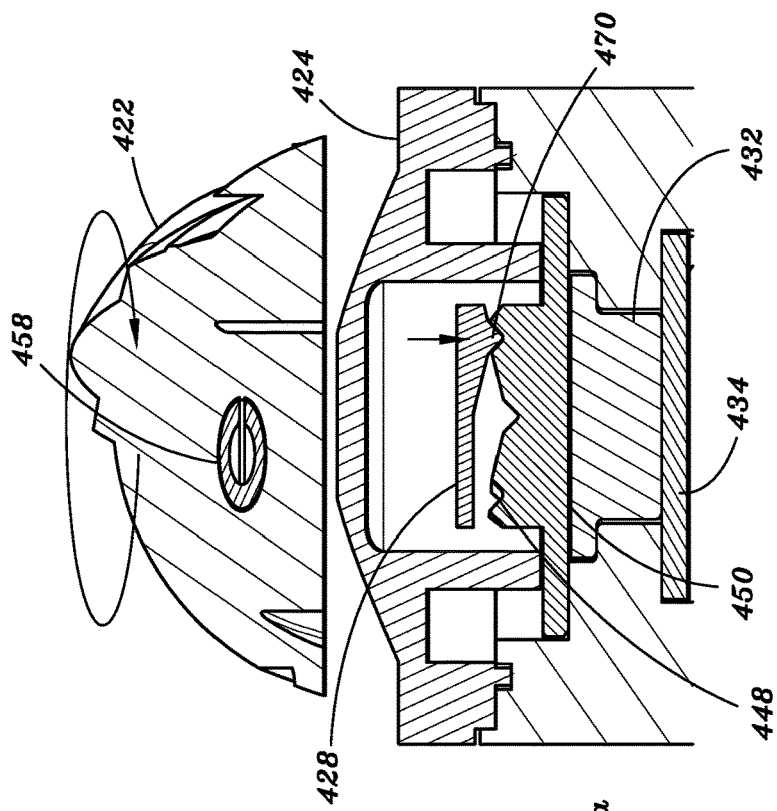
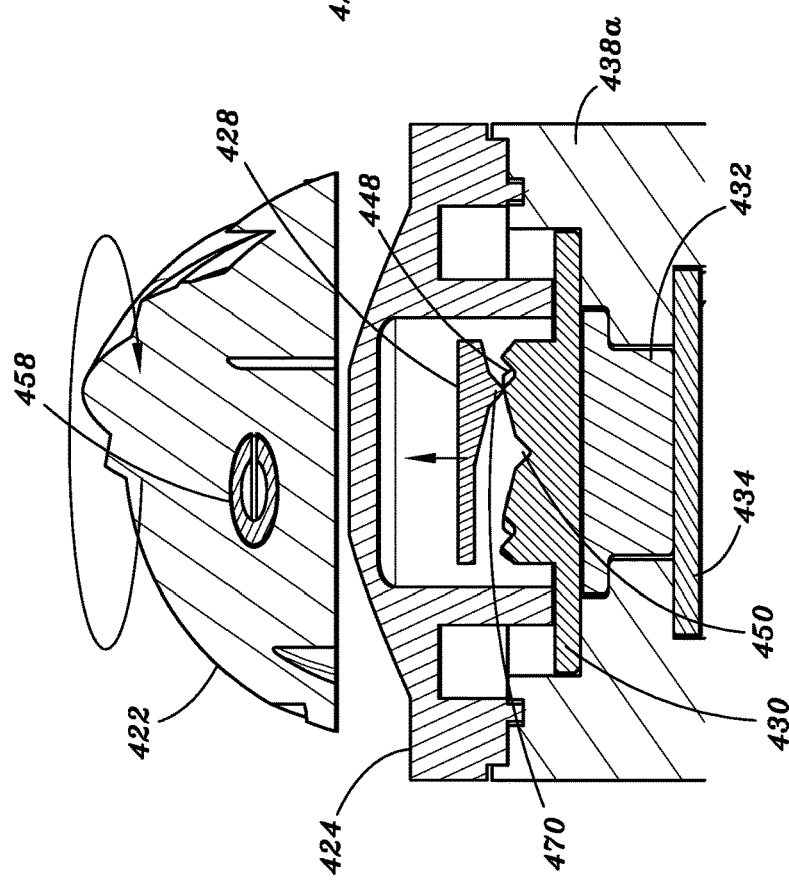

SURGICAL INSTRUMENT

CROSS-REFERENCE TO RELATED APPLICATIONS

The present application is a divisional of U.S. patent application Ser. No. 14/517,281, filed Oct. 17, 2014, now U.S. Pat. No. 9,655,617, which is a continuation of U.S. patent application Ser. No. 14/062,447, filed Oct. 24, 2013, now U.S. Pat. No. 8,888,814, which is a continuation of U.S. patent application Ser. No. 13/788,579 filed on Mar. 7, 2013, now U.S. Pat. No. 8,573,460, which is a continuation of U.S. patent application Ser. No. 13/542,690 filed on Jul. 6, 2012, now U.S. Pat. No. 8,413,868, which is a continuation of U.S. patent application Ser. No. 13/273,670 filed on Oct. 14, 2011, now U.S. Pat. No. 8,235,274, which is a Continuation of U.S. patent application Ser. No. 12/580,371 filed on Oct. 16, 2009, now U.S. Pat. No. 8,061,576, which is a Continuation-in-part of U.S. patent application Ser. No. 12/200,004 filed on Aug. 28, 2008, now U.S. Pat. No. 7,624,902, which claims the benefit of U.S. Provisional Patent Application Ser. No. 60/967,169 filed on Aug. 31, 2007, the entire contents of each of these prior applications are hereby incorporated by reference.

BACKGROUND

1. Technical Field

This application relates to a surgical instrument, and more particularly, to an articulating mechanism for use with an endoscopic surgical instrument.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

Instruments for this purpose can include two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. Nos. 3,079,606 and 3,490,675.

A later stapler disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. Other examples of such staplers are disclosed in U.S. Pat. Nos. 4,429,695 and 5,065,929.

Each of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); and U.S. Pat. No. 5,332,142 (Robinson, et al.).

U.S. Surgical, the assignee of the present application, has manufactured and marketed endoscopic stapling instruments, such as the Multifire ENDO GIA* 30 instrument, for several years. These instruments have provided significant clinical benefits. Nonetheless, improvements are possible, for example, by reducing the cost and complexity of manufacture.

Current laparoscopic linear stapling devices are configured to operate with disposable loading units and/or staple cartridges of only one size. For example, individual linear staplers are presently available for applying parallel rows of staples measuring 30 mm, 45 mm and 60 mm in length. Thus, during a normal operation, a surgeon may be required to utilize several different stapling instruments to perform a single laparoscopic surgical procedure. Such practices increase the time, complexity and overall costs associated with laparoscopic surgical procedures. In addition, costs are greater in designing and manufacturing multiple stapler sizes, as opposed to creating a single, multipurpose stapler.

SUMMARY

The present disclosure relates to a surgical instrument comprising a handle assembly, a body, a tool assembly and an articulation assembly. The body extends distally from the handle assembly and defining a first longitudinal axis. The tool assembly is pivotably supported on a distal end of the body and defines a second longitudinal axis. The tool assembly is pivotable between a non-articulated position in which the first longitudinal axis is aligned with the second longitudinal axis and at least one articulated position in which the second longitudinal axis is at an angle to the first longitudinal axis. The articulation mechanism includes a receptacle positioned adjacent the handle assembly, and a main shaft having a base portion. The main shaft is rotatably supported within the receptacle. A lower clutch is fixedly positioned within the receptacle and has a serrated portion including a plurality of serrations and being positioned about the main shaft. An upper clutch is slidably positioned about the main shaft and is rotatably fixed to the main shaft such that rotation of the main shaft affects rotation of the upper clutch. The upper clutch includes at least one projection positioned to engage the serrations of the lower clutch to releasably retain the main shaft at a rotatably fixed position. The articulation link has a proximal end operatively connected to the base portion of the main shaft and a distal end operatively connected to the tool assembly. The main shaft is rotatable to move the articulation link to affect movement of the tool assembly between the non-articulated position and the at least one articulated position. An angle between a first pair of adjacent serrations is defined as a first angle, an angle between a second pair of adjacent serrations is defined as a second angle, and an angle between a third pair of adjacent serrations is defined as a third angle. The first angle, the second angle, and the third angle are each different from one another.

The present disclosure also relates to an articulation mechanism for affecting movement of a tool assembly of a surgical instrument between a non-articulated position and at least one articulated position. The articulation mechanism comprises a receptacle, a main shaft, a lower clutch and an upper clutch. The main shaft has a base portion and is rotatably supported within the receptacle. The lower clutch is fixedly positioned within the receptacle and has a serrated portion including a plurality of serrations and being positioned about the main shaft. The upper clutch is slidably positioned about the main shaft and is rotatably fixed to the main shaft such that rotation of the main shaft affects rotation of the upper clutch. The upper clutch includes at least one projection positioned to engage the serrations of the lower clutch to releasably retain the main shaft at a rotatably fixed position. An angle between a first pair of adjacent serrations is defined as a first angle, an angle between a second pair of adjacent serrations is defined as a second angle, and an angle between a third pair of adjacent serrations is defined as a third angle. Each of the first angle, the second angle, and the third angle are different from one another.

BRIEF DESCRIPTION OF THE DRAWINGS

Various embodiments are described herein with reference to the drawings:

FIG. 2 is a top view of the surgical instrument shown in FIG. 1;

FIG. 3 is a side view of the surgical instrument shown in FIG. 1;

FIG. 10a is a perspective view of the translation member of the articulating mechanism and the proximal end of the elongated body of the surgical instrument shown in FIG. 1;

FIG. 19 is a perspective view of a disposable loading unit usable with the surgical instrument of FIG. 1;

FIG. 20 is another perspective view of a disposable loading unit usable with the surgical instrument of FIG. 1;

FIG. 25 is a bottom perspective view of the staple cartridge shown in FIG. 21;

FIG. 26 is an enlarged perspective view of the actuation sled, the pushers and the fasteners shown in FIG. 21;

FIG. 28 is an enlarged perspective view of the mounting assembly of the disposable loading unit shown in FIG. 19 mounted to a distal end portion of the proximal housing portion;

FIG. 29 is an enlarged perspective view of the proximal housing portion and the mounting assembly of the disposable loading unit shown in FIG. 19 with the upper housing half removed;

FIG. 30 is a perspective view of the proximal housing portion and the mounting assembly of the disposable loading unit shown in FIG. 19 with the upper housing half removed;

FIG. 32 is an enlarged perspective view of the axial drive assembly shown in FIG. 31;

FIG. 33 is an enlarged perspective view of the proximal end of the axial drive assembly shown in FIG. 31 including the locking device;

FIG. 34 is an enlarged perspective view of the distal end of the axial drive assembly shown in FIG. 31;

FIG. 35 is an enlarged perspective view of the distal end of the elongated body of the stapling apparatus shown in FIG. 1;

FIG. 36 is an enlarged perspective view of the locking device shown in FIG. 33;

FIG. 37 is an enlarged perspective view of a lower housing half of the proximal housing portion of the disposable loading unit shown in FIG. 27;

FIG. 41 is an enlarged perspective view of the disposable loading unit of FIG. 19 during attachment to the elongated body of the surgical instrument shown in FIG. 1;

FIG. 42 is another enlarged perspective view of the disposable loading unit of FIG. 19 during attachment to the elongated body of the surgical instrument shown in FIG. 1;

FIG. 43 is a cross-sectional view taken along section line 43-43 of FIG. 41;

FIG. 44 is a cross-sectional view taken along section line 44-44 of FIG. 42;

FIG. 54 is a side cross-sectional view of the handle assembly of the stapling apparatus during actuation of the emergency release button;

FIG. 57 is a top view of the distal end of the elongated body, the mounting assembly, and the proximal end of the tool assembly during articulation of the stapling apparatus;

FIG. 58 is a perspective view of the surgical instrument during articulation of the tool assembly;

FIG. 59 is a perspective view of the surgical instrument during articulation and rotation of the tool assembly;

FIG. 60 is a top view of the distal end of the disposable loading unit immediately prior to articulation;

FIG. 61 is a top view of the distal end of the elongated body, the mounting assembly, and the proximal end of the tool assembly during articulation of the stapling apparatus;

FIG. 68 is a bottom side perspective view of the upper clutch of the articulation mechanism shown in FIG. 65;

FIG. 68A is a perspective view of a lower face of an upper clutch according to an alternate embodiment of the present disclosure;

FIG. 69 is a perspective view from the top of the upper clutch shown in FIG. 68;

FIG. 71 is a top perspective view of the main shaft of the articulation mechanism shown in FIG. 65;

FIG. 72 is a bottom perspective view of the main shaft shown in FIG. 71;

FIG. 73 is a top perspective view of the cover of the articulation mechanism shown in FIG. 65;

FIG. 74 is a bottom perspective view of the cover shown in FIG. 73;

FIG. 79 is a cross-sectional view taken along section lines 79-79 of FIG. 78; and FIG. 80 is a cross-sectional view of the articulation mechanism shown in FIG. 64 with the articulation lever rotated and the upper clutch projection reengaged with the serrations of the lower clutch.

DETAILED DESCRIPTION OF EMBODIMENTS

Figure 1:
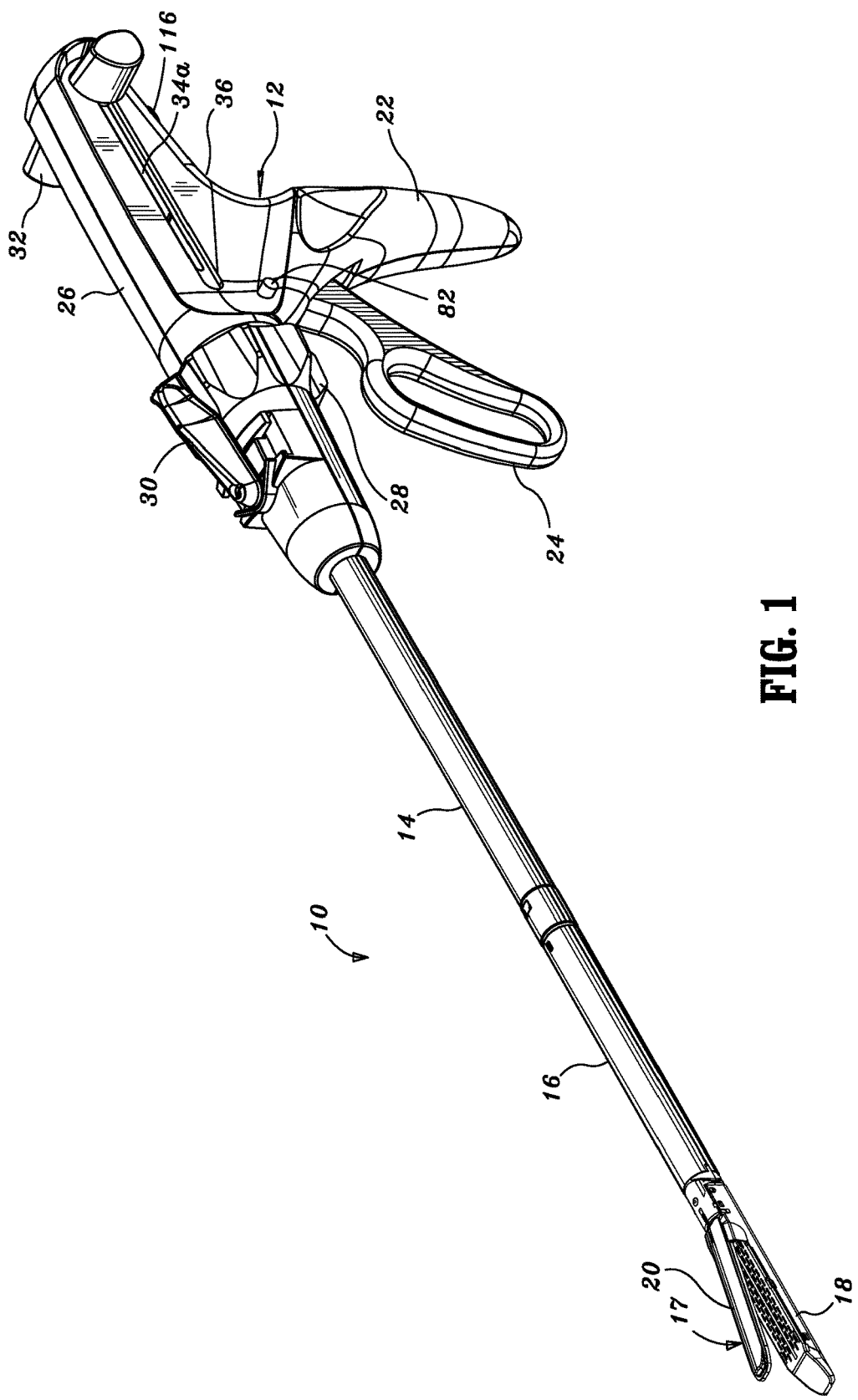
FIG. 1 is a perspective view of one preferred embodiment of the presently disclosed surgical instrument.

Preferred embodiments of the presently disclosed endoscopic surgical instrument will now be described in detail with reference to the drawings, in which like reference numerals designate identical or corresponding elements in each of the several views.

In the drawings and in the description that follows, the term "proximal", as is traditional, will refer to the end of the stapling apparatus which is closest to the operator, while the term distal will refer to the end of the apparatus which is furthest from the operator.

FIGS. 1-3 illustrate one embodiment of the presently disclosed surgical instrument shown generally as 10. Briefly, surgical instrument 10 includes a handle assembly 12 and an elongated body 14. A disposable loading unit or DLU 16 is releasably secured to a distal end of elongated body 14. Disposable loading unit 16 includes a tool assembly 17 having a cartridge assembly 18 housing a plurality of surgical staples and an anvil assembly 20 movably secured in relation to cartridge assembly 18. Disposable loading unit 16 is configured to apply linear rows of staples measuring from about 30 mm to about 60 mm in length. Disposable loading units having linear rows of staples of other lengths are also envisioned, e.g., 45 mm. Handle assembly 12 includes a stationary handle member 22, a movable handle member 24, and a barrel portion 26. A rotatable member 28 is preferably mounted on the forward end of barrel portion 26 to facilitate rotation of elongated body 14 with respect to handle assembly 12. An articulation lever 30 is also preferably mounted on the forward end of barrel portion 26 adjacent rotatable knob 28 to facilitate articulation of tool assembly 17. A pair of retraction knobs 32 are movably positioned along barrel portion 26 to return surgical instrument 10 to a retracted position, as will be described in detail below.

Figure 4:
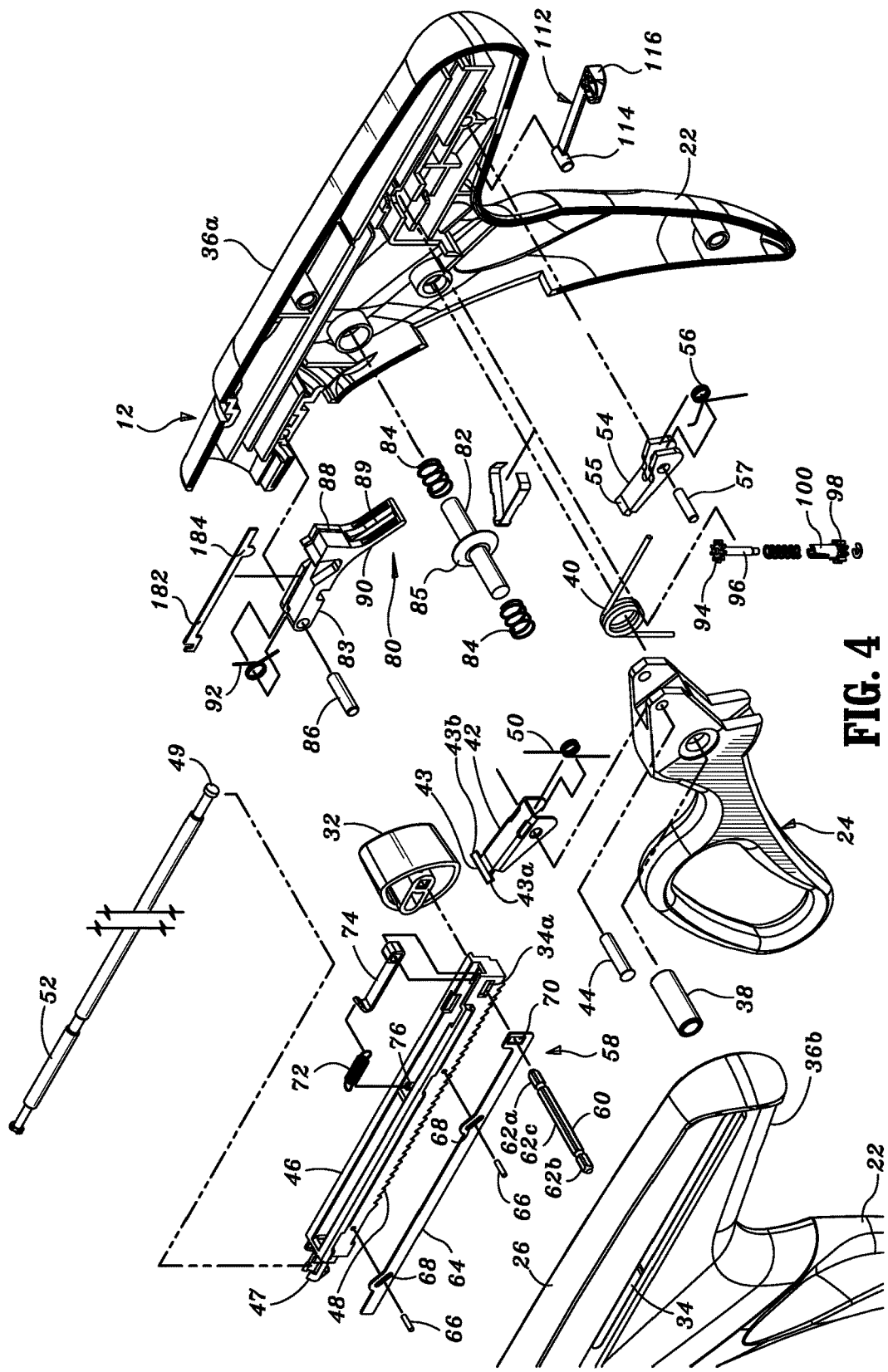
FIG. 4 is a perspective view with parts separated of the handle assembly of the surgical instrument shown in FIG. 1.

Referring to FIG. 4, handle assembly 12 includes housing 36, which is preferably formed from molded housing half-sections 36a and 36b, which forms stationary handle member 22 and barrel portion 26 of handle assembly 12 (See FIG. 1). Movable handle member 24 is pivotably supported between housing half-sections 36a and 36b about pivot pin 38. A biasing member 40, which is preferably a torsion spring, biases movable handle 24 away from stationary handle 22. An actuation shaft 46 is supported within barrel portion 26 of housing 36 and includes a toothed rack 48. A driving pawl 42 having a rack engagement finger 43 with laterally extending wings 43a and 43b is pivotably mounted to one end of movable handle 24 about a pivot pin 44. A biasing member 50, which is also preferably a torsion spring, is positioned to urge engagement finger 43 of driving pawl 42 towards toothed rack 48 of actuation shaft 46. Movable handle 24 is pivotable to move engagement finger 43 of driving pawl 42 into contact with toothed rack 48 of actuation shaft 46 to advance the actuation shaft linearly in the distal direction. The forward end of actuation shaft 46 rotatably receives the proximal end 49 of a control rod 52 such that linear advancement of actuation shaft 46 causes corresponding linear advancement of control rod 52. A locking pawl 54 having a rack engagement member 55 is pivotably mounted within housing 36 about pivot pin 57 and is biased towards toothed rack 48 by biasing member 56, which is also preferably a torsion spring. Engagement member 55 of locking pawl 54 is movable into engagement with toothed rack 48 to retain actuation shaft 46 in a longitudinally fixed position.

A retraction mechanism 58 which includes a pair of retractor knobs 32 (See FIG. 1) is connected to the proximal end of actuation shaft 46 by a coupling rod 60. Coupling rod 60 includes right and left engagement portions 62a and 62b for receiving retractor knobs 32 and a central portion 62c which is dimensioned and configured to translate within a pair of longitudinal slots 34a formed in actuation shaft 46 adjacent the proximal end thereof. A release plate 64 is operatively associated with actuation shaft 46 and is mounted for movement with respect thereto in response to manipulation of retractor knobs 32. A pair of spaced apart pins 66 extend outwardly from a lateral face of actuation shaft 46 to engage a pair of corresponding angled cam slots 68 formed in release plate 64. Upon rearward movement of retractor knobs 32, pins 66 can release plate 64 downwardly with respect to actuation shaft 46 and with respect to toothed rack 48 such that the bottom portion of release plate 64 extends below toothed rack 48 to disengage engagement finger 43 of driving pawl 42 from toothed rack 48. A transverse slot 70 is formed at the proximal end of release plate 64 to accommodate the central portion 62c of coupling rod 60, and elongated slots 34 (See FIG. 1) are defined in the barrel section 26 of handle assembly 12 to accommodate the longitudinal translation of coupling rod 60 as retraction knobs 32 are pulled rearwardly to retract actuation shaft 46 and thus retract control rod 52 rearwardly. Actuation shaft 46 is biased proximally by spring 72 which is secured at one end to coupling rod portion 62 via connector 74 and at the other end to post 76 on actuation shaft 46.

Figure 5:
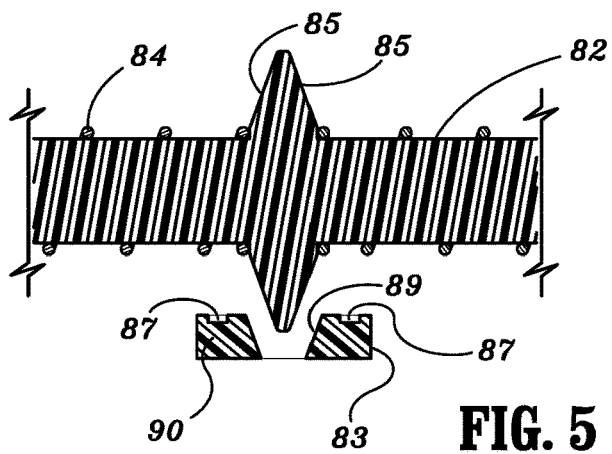
FIG. 5 is a cross-sectional view of a portion of the firing lockout mechanism shown in FIG. 4.

Referring also to FIG. 5, handle assembly 12 includes a firing lockout assembly 80 which includes a plunger 82 and a pivotable locking member 83. Plunger 82 is biased to a central position by biasing springs 84 and includes annular tapered camming surfaces 85. Each end of plunger 82 extends through housing 36 (See FIG. 1) adjacent an upper end of stationary handle 22. Pivotable locking member 83 is pivotably attached at its distal end between housing half-sections 36a and 36b about pivot pin 86 and includes a locking surface 88 and proximal extension 90 having a slot 89 formed therein. Locking member 83 is biased by spring 92 counter-clockwise (as viewed in FIG. 4) to move locking surface 88 to a position to abut the distal end of actuation shaft 46 to prevent advancement of shaft 46 and subsequent firing of stapling apparatus 10. Annular tapered camming surface 85 is positioned to extend into tapered slot 89 in proximal extension 90. Lateral movement of plunger 82 in either direction against the bias of either spring 84 moves tapered camming surface 85 into engagement with the sidewalls of tapered slot 89 to pivot locking member 83 clockwise about pivot pin 86, as viewed in FIG. 4, to move blocking surface 88 to a position to permit advancement of actuation shaft 46 and thus firing of stapling apparatus 10. Blocking surface 88 is retained in this position by recesses 87 which receive the tapered tip of camming surface 85 to lock locking member 83 in a counter-clockwise position. Operation of firing lockout assembly 80 will be further illustrated below.

Figure 6:
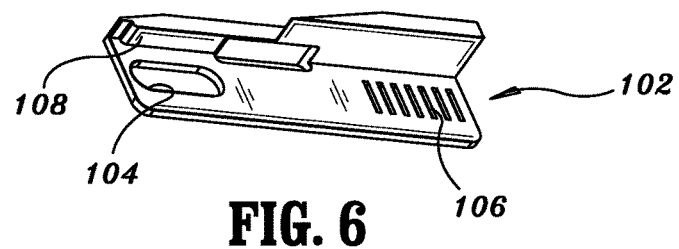
FIG. 6 is a perspective of the slide plate of the anti-reverse clutch mechanism of the surgical instrument.
Figure 7:
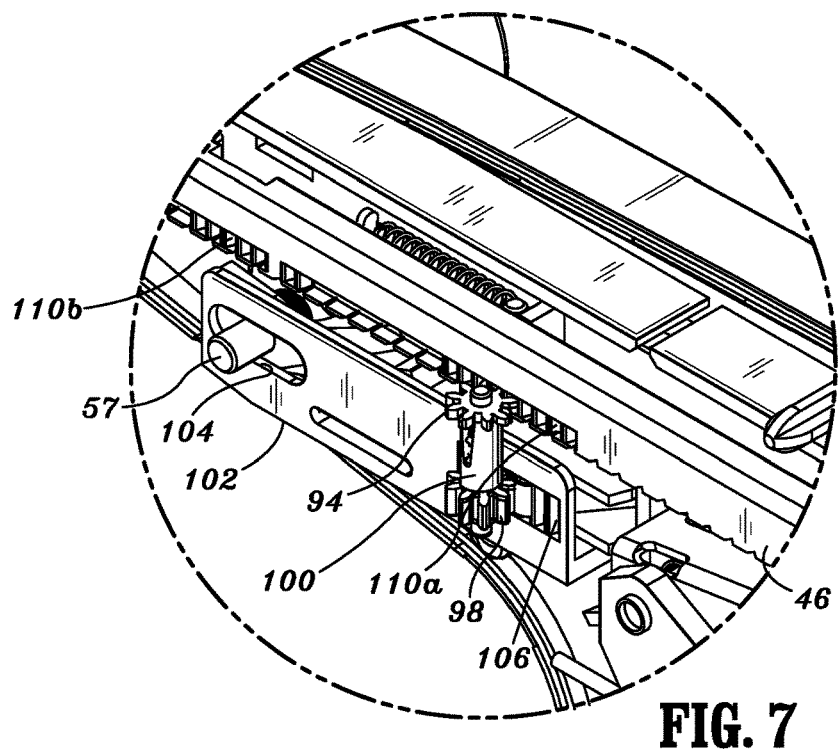
FIG. 7 is an enlarged perspective view of the anti-reverse clutch mechanism shown in FIG. 1.

Referring to FIGS. 4, 6, and 7, handle mechanism 12 also includes an anti-reverse clutch mechanism which includes a first gear 94 rotatably mounted on a first shaft 96, and second gear 98 mounted on a second shaft 100, and a slide plate 102 (FIGS. 6 and 7) slidably mounted within housing 36. Slide plate 102 includes an elongated slot 104 dimensioned and configured to be slidably positioned about locking pawl pivot pin 57, a gear plate 106 configured to mesh with the teeth of second gear 98, and a cam surface 108. In the retracted position, cam surface 108 of slide plate 102 engages locking pawl 54 to prevent locking pawl 54 from engaging toothed rack 48. Actuation shaft 46 includes a distal set of gear teeth 110a spaced from a proximal set of gear teeth 110b positioned to engage first gear 94 of actuation shaft 46 during movement of actuation shaft 46. When actuation shaft 46 is advanced by pivoting movable handle 24 about pivot pin 38, distal gear teeth 110a on actuation shaft 46 mesh with and rotate first gear 94 and first shaft 96. First shaft 96 is connected to second shaft 100 by spring clutch assembly such that rotation of first shaft 96 will cause corresponding rotation of second shaft 100. Rotation of second shaft 100 causes corresponding rotation of second gear 98 which is engaged with gear plate 106 on slide plate 102 to cause linear advancement of slide plate 102. Linear advancement of slide plate 102 is limited to the length of elongated slot 104. When slide plate has been advanced the length of slot 104, cam surface 108 releases locking pawl 54 such that it is moved into engagement with toothed rack 48. Continued advancement of actuation shaft 46 eventually moves gear teeth 110b into engagement with gear plate 106. However, since slide plate 102 is longitudinally fixed in position, the spring clutch is forced to release, such that continued distal advancement of actuation shaft 46 is permitted.

When actuation shaft 46 is returned to the retracted position (by pulling retraction knobs 34 proximally, as discussed above) gear teeth 110b engage first gear 94 to rotate second gear 98 in the reverse direction to retract slide member 102 proximally within housing 36. Proximal movement of slide member 102 advances cam surface 108 into locking pawl 54 prior to engagement between locking pawl 54 and toothed rack 48 to urge locking pawl 54 to a position to permit retraction of actuation shaft 46.

Referring again to FIG. 4, handle assembly 12 includes an emergency return button 112 pivotally mounted within housing 36 about a pivot member 114 supported between housing half-sections 36a and 36b. Return button 112 includes an externally positioned member 116 positioned on the proximal end of barrel portion 26. Member 116 is movable about pivot member 114 into engagement with the proximal end of locking pawl 54 to urge rack engagement member 55 out of engagement with toothed rack 48 to permit retraction of actuation shaft 46 during the firing stroke of the stapling apparatus 10. As discussed above, during the clamping portion of advancement of actuation shaft 46, slide plate 102 disengages pawl 54 from rack 48 and thus actuation of return button 112 is not necessary to retract the actuation shaft 46.

Figure 8:
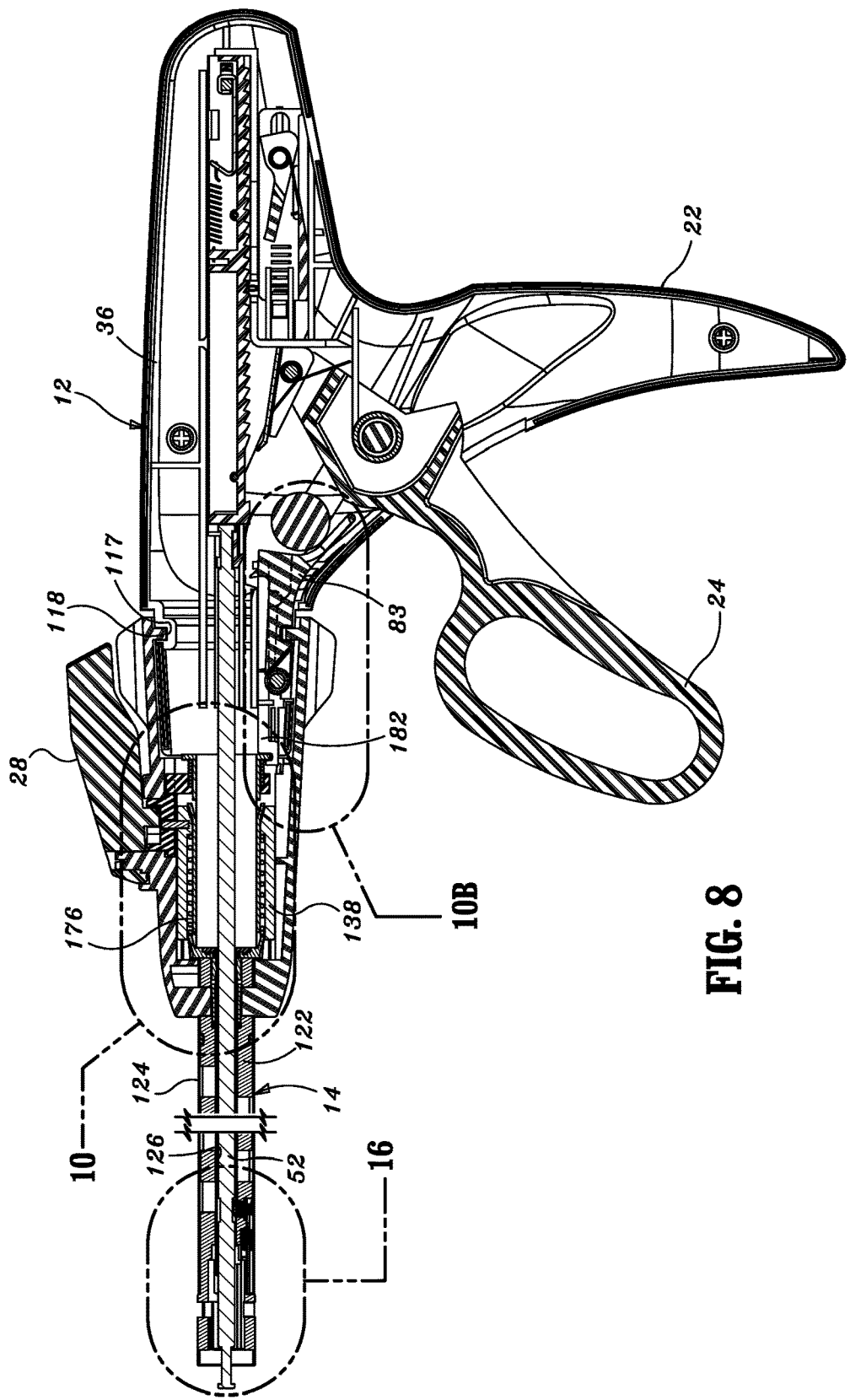
FIG. 8 is a side cross-sectional view of the surgical instrument shown in FIG. 1 in the non-actuated position with the disposable loading unit removed.
Figure 9:
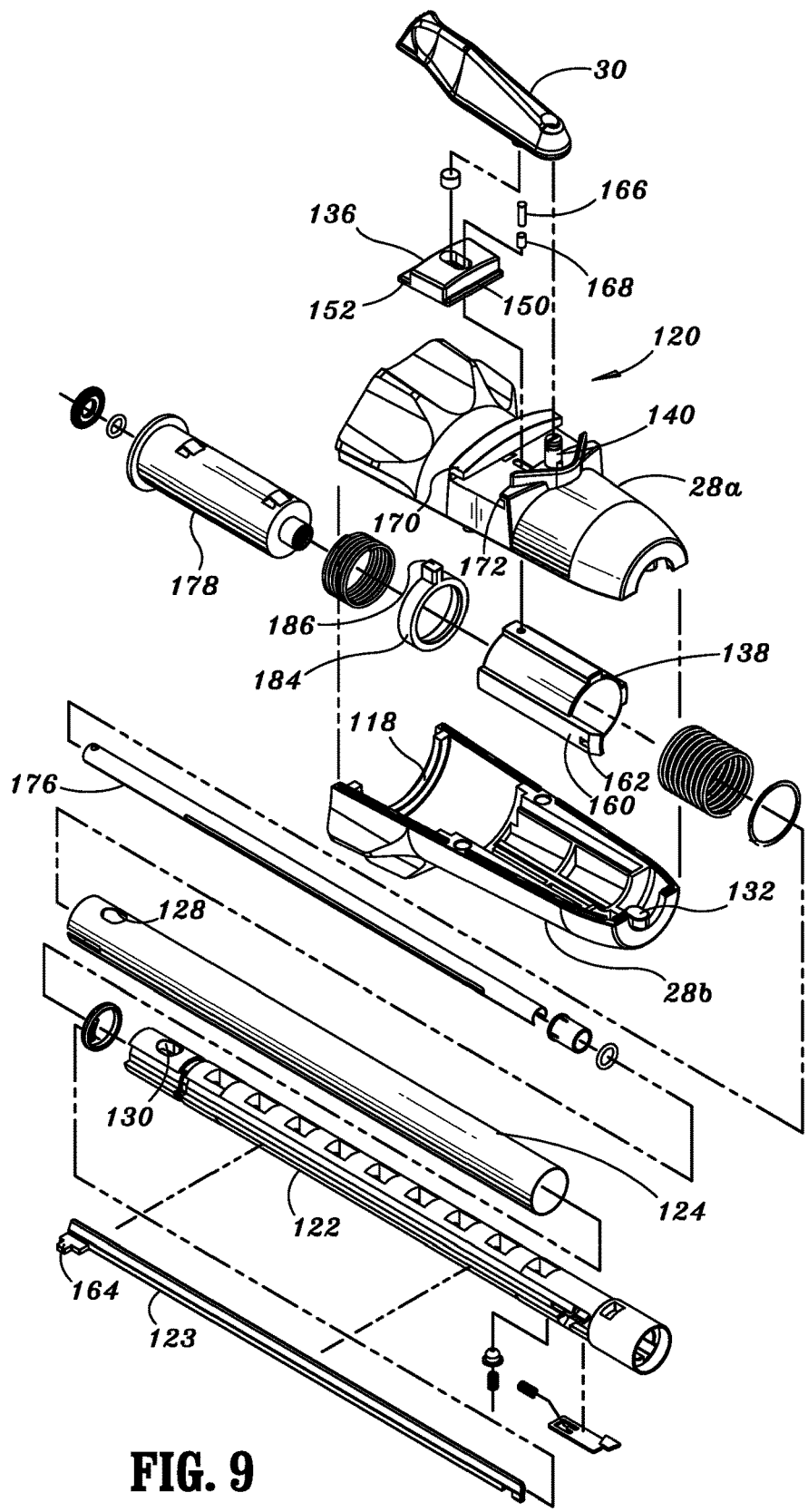
FIG. 9 is a perspective view with parts separated of the rotation member, the articulation mechanism, and the elongated body of the surgical instrument shown in FIG. 1.
Figure 10:
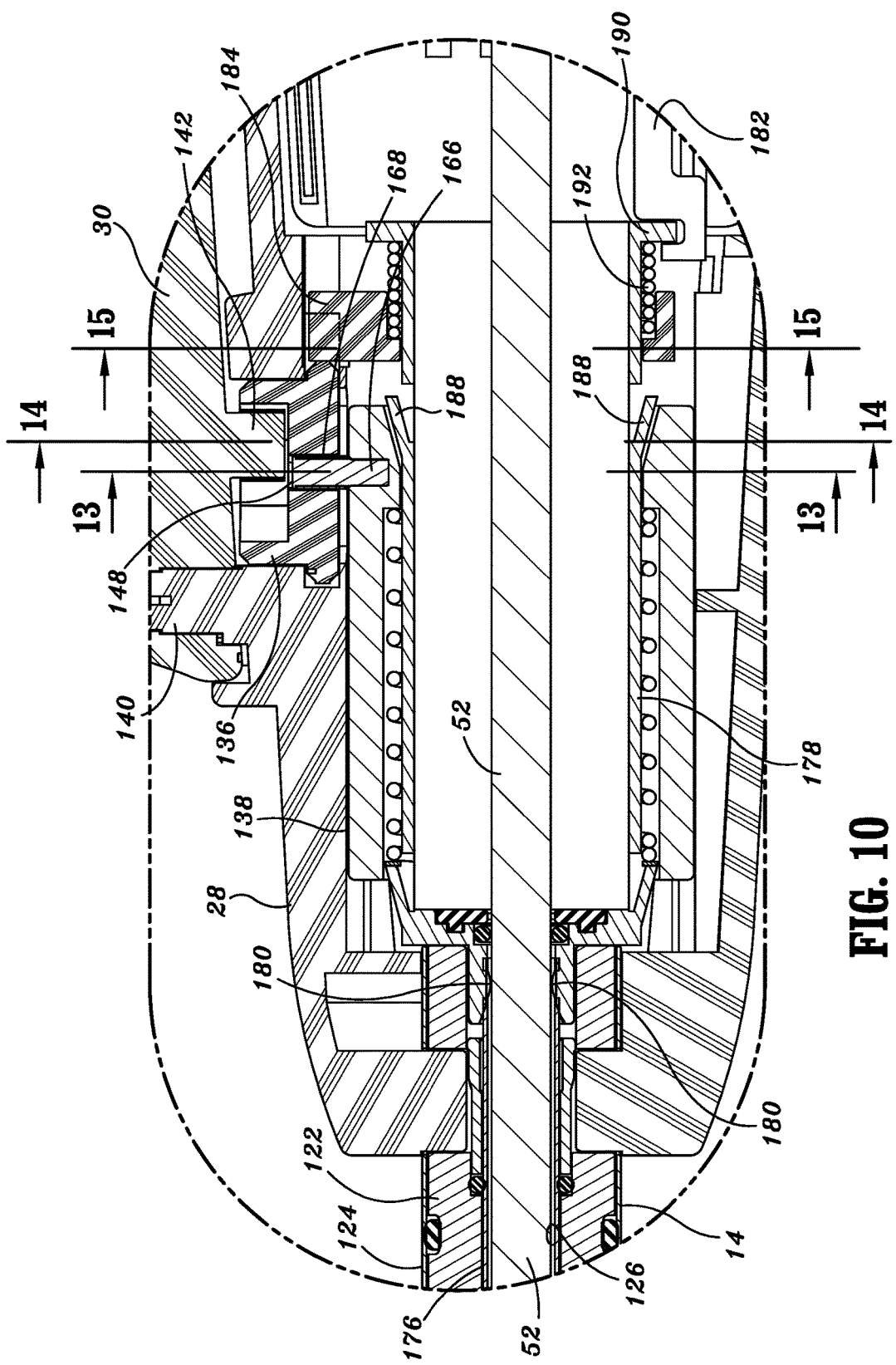
FIG. 10 is an enlarged view of the indicated area of detail shown in FIG. 8.
Figure 10B:
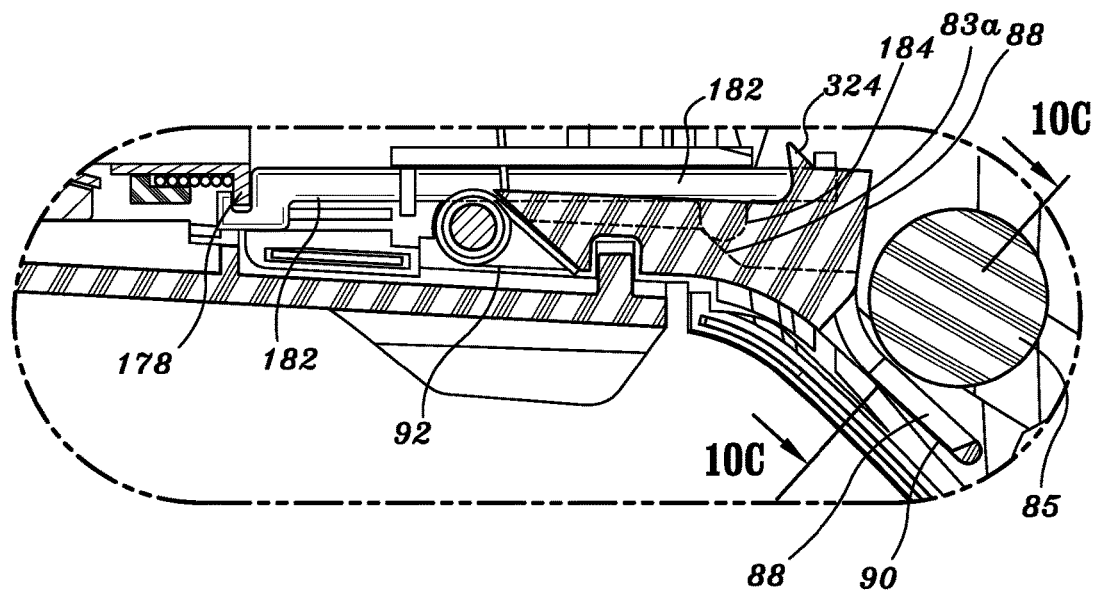
FIG. 10b is an enlarged cross-sectional view of the indicated area of detail of FIG. 8.
Figure 10C:
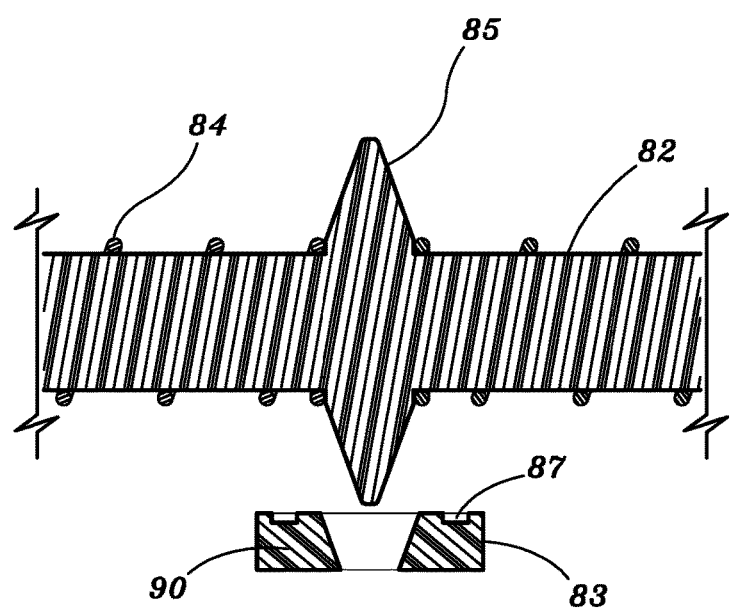
FIG. 10c is a cross-sectional view along section line 10c-10c of FIG. 8.

FIG. 8 illustrates the interconnection of elongated body 14 and handle assembly 12. Referring to FIGS. 8-10, housing 36 includes an annular channel 117 configured to receive an annular rib 118 formed on the proximal end of rotation member 28, which is preferably formed from molded half-sections 28a and 28b. Annular channel 117 and rib 118 permit relative rotation between rotation member 28 and housing 36. Elongated body 14 includes inner housing 122 and an outer casing 124. Inner housing 122 is dimensioned to be received within outer casing 124 and includes an internal bore 126 (FIG. 8) which extends therethrough and is dimensioned to slidably receive a first articulation link 123 and control rod 52. The proximal end of housing 122 and casing 124 each include a pair of diametrically opposed openings 130 and 128, respectively, which are dimensioned to receive radial projections 132 formed on the distal end of rotation member 28. Projections 132 and openings 128 and 130 fixedly secure rotation member 28 and elongated body 14 in relation to each other, both longitudinally and rotatably. Rotation of rotation knob 28 with respect to handle assembly 12 thus results in corresponding rotation of elongated body 14 with respect to handle assembly 12.

An articulation mechanism 120 is supported on rotatable member 28 and includes articulation lever 30, a cam member 136, a translation member 138, and first articulation link 123 (FIG. 9). Articulation lever 30 is pivotably mounted about pivot member 140 which extends outwardly from rotation member 28 and is preferably formed integrally therewith. A projection 142 extends downwardly from articulation lever 30 for engagement with cam member 136.

Figure 12:
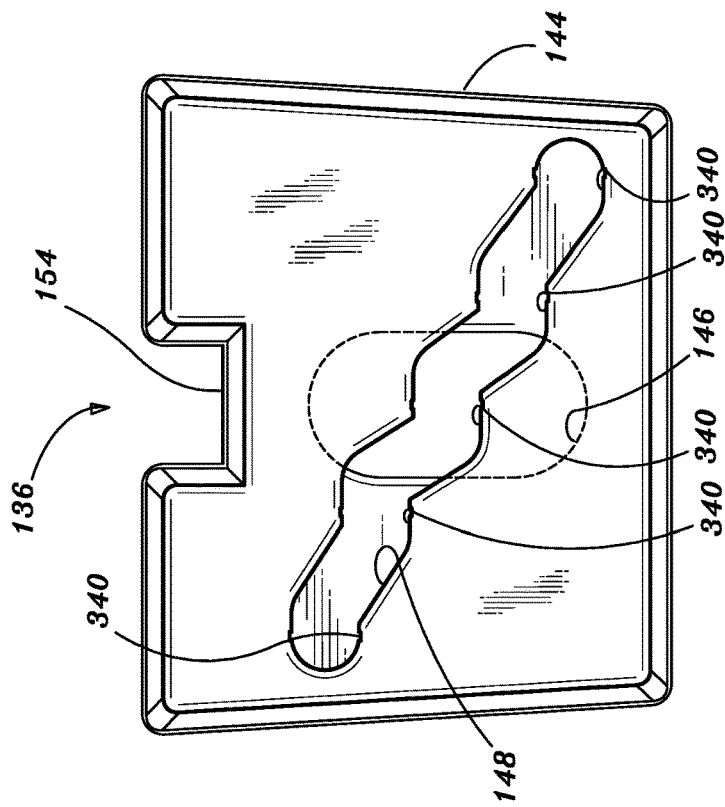
FIG. 12 is a top view of the cam member of the articulation mechanism of the surgical instrument shown in FIG. 1.
Figure 11:
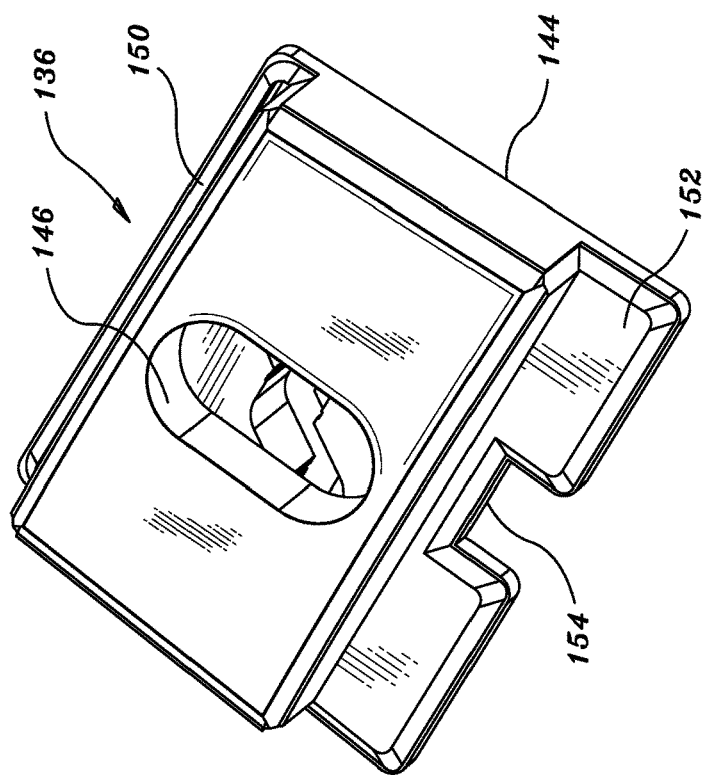
FIG. 11 is a perspective view of the cam member of the articulation mechanism of the surgical instrument shown in FIG. 1.

Referring temporarily to FIGS. 11 and 12, cam member 136 includes a housing 144 having an elongated slot 146 extending through one side thereof and a stepped camming surface 148 formed in the other side thereof. Each step of camming surface 148 corresponds to a particular degree of articulation of stapling apparatus 10. Although five steps are illustrated, fewer or more steps may be provided. Elongated slot 146 is configured to receive projection 142 formed on articulation lever 30. Housing 144 includes a distal stepped portion 150 and a proximal stepped portion 152. Proximal stepped portion 152 includes a recess 154.

Figure 13:
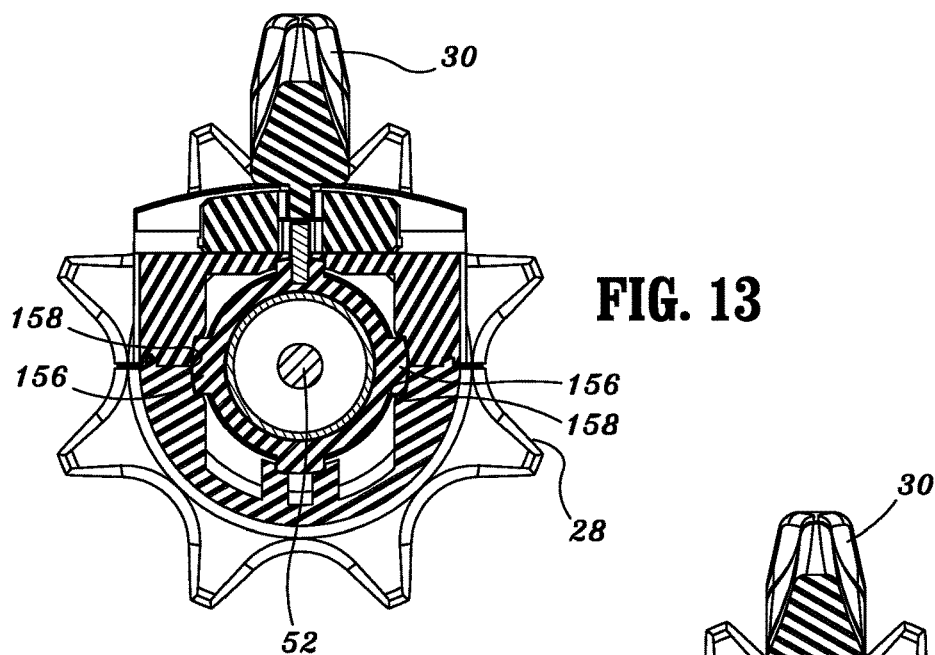
FIG. 13 is a cross-sectional view taken along section line 13-13 of FIG. 10.
Figure 14:
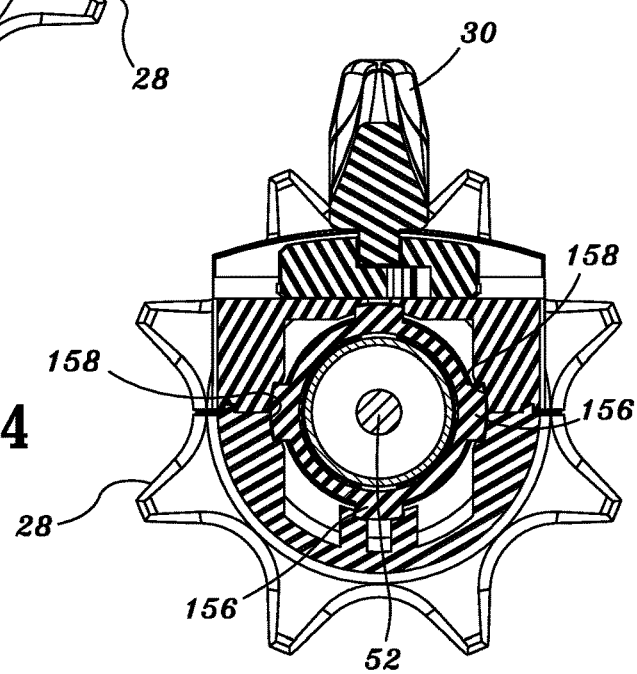
FIG. 14 is a cross-sectional view taken along section line 14-14 of FIG. 10.
Figure 15:
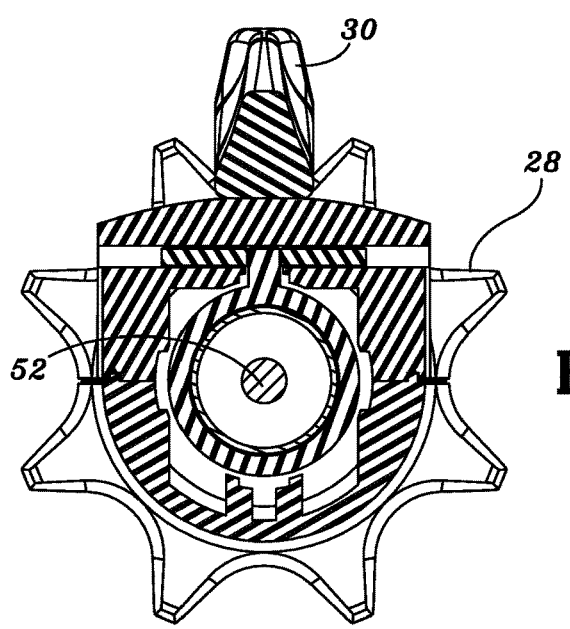
FIG. 15 is a cross-sectional view taken along section line 15-15 of FIG. 10.

Referring again to FIGS. 8-10 and also to FIGS. 13-15, translation member 138 includes a plurality of ridges 156 which are configured to be slidably received within grooves 158 formed along the inner walls of rotation member 28. Engagement between ridges 156 and grooves 158 prevent relative rotation of rotation member 28 and translation member 138 while permitting relative linear movement. The distal end of translation member 138 includes arm 160 which includes an opening 162 configured to receive a finger 164 extending from the proximal end of articulation link 123 (See FIG. 10a). A pin 166 having a housing 168 constructed from a non-abrasive material, e.g., teflon, is secured to translation member 138 and dimensioned to be received within stepped camming surface 148.

In an assembled condition, proximal and distal stepped portions 150 and 152 of cam member 136 are positioned beneath flanges 170 and 172 formed on rotation member 28 to restrict cam member 136 to transverse movement with respect to the longitudinal axis of stapling apparatus 10. When articulation lever 30 is pivoted about pivot member 140, cam member 136 is moved transversely on rotation member 28 to move stepped camming surface 148 transversely relative to pin 166, forcing pin 166 to move proximally or distally along stepped cam surface 148. Since pin 166 is fixedly attached to translation member 138, translation member 138 is moved proximally or distally to effect corresponding proximal or distal movement of first actuation link 123.

Figure 64:
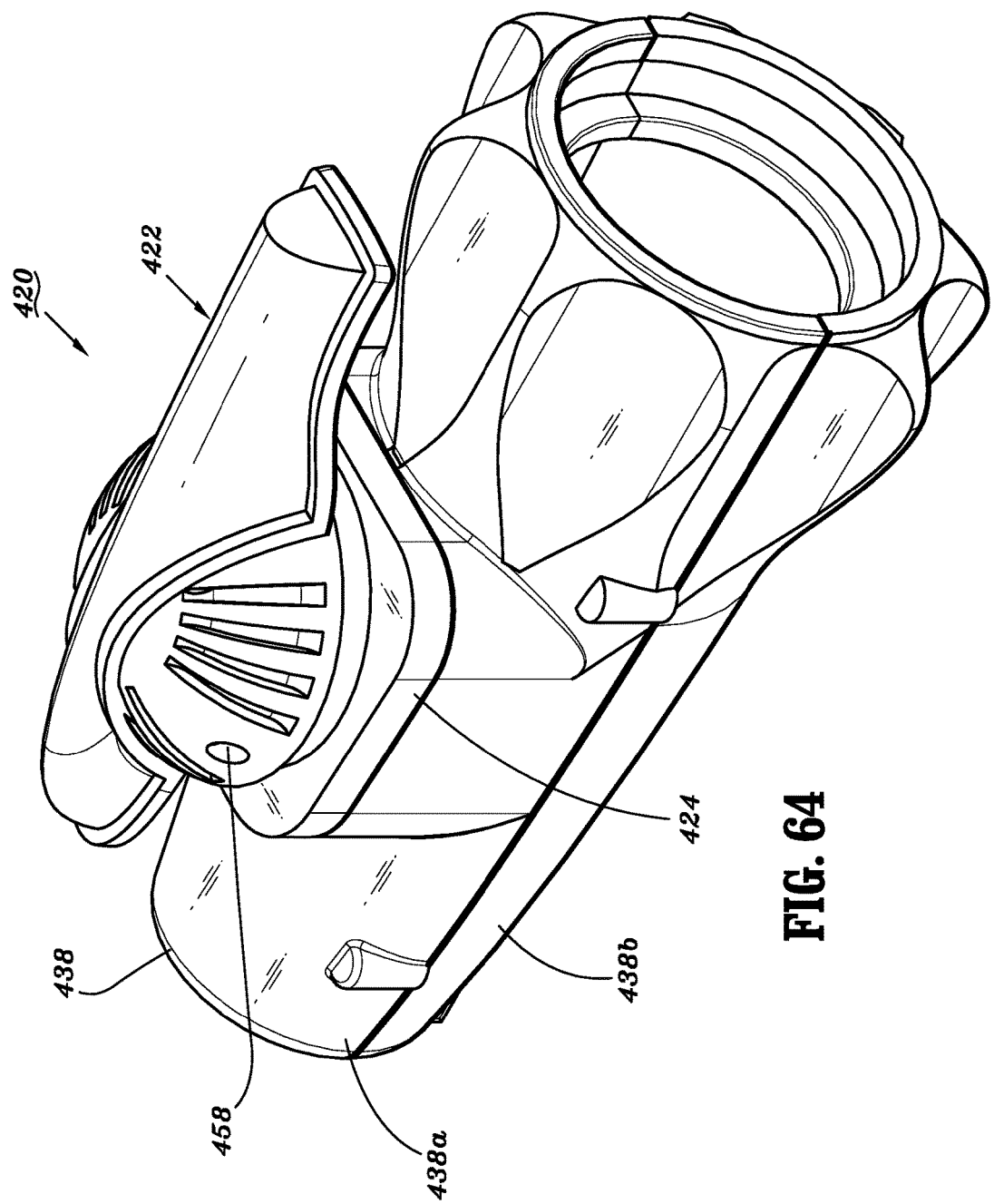
FIG. 64 is a perspective view of another embodiment of the presently disclosed articulation mechanism.
Figure 65:
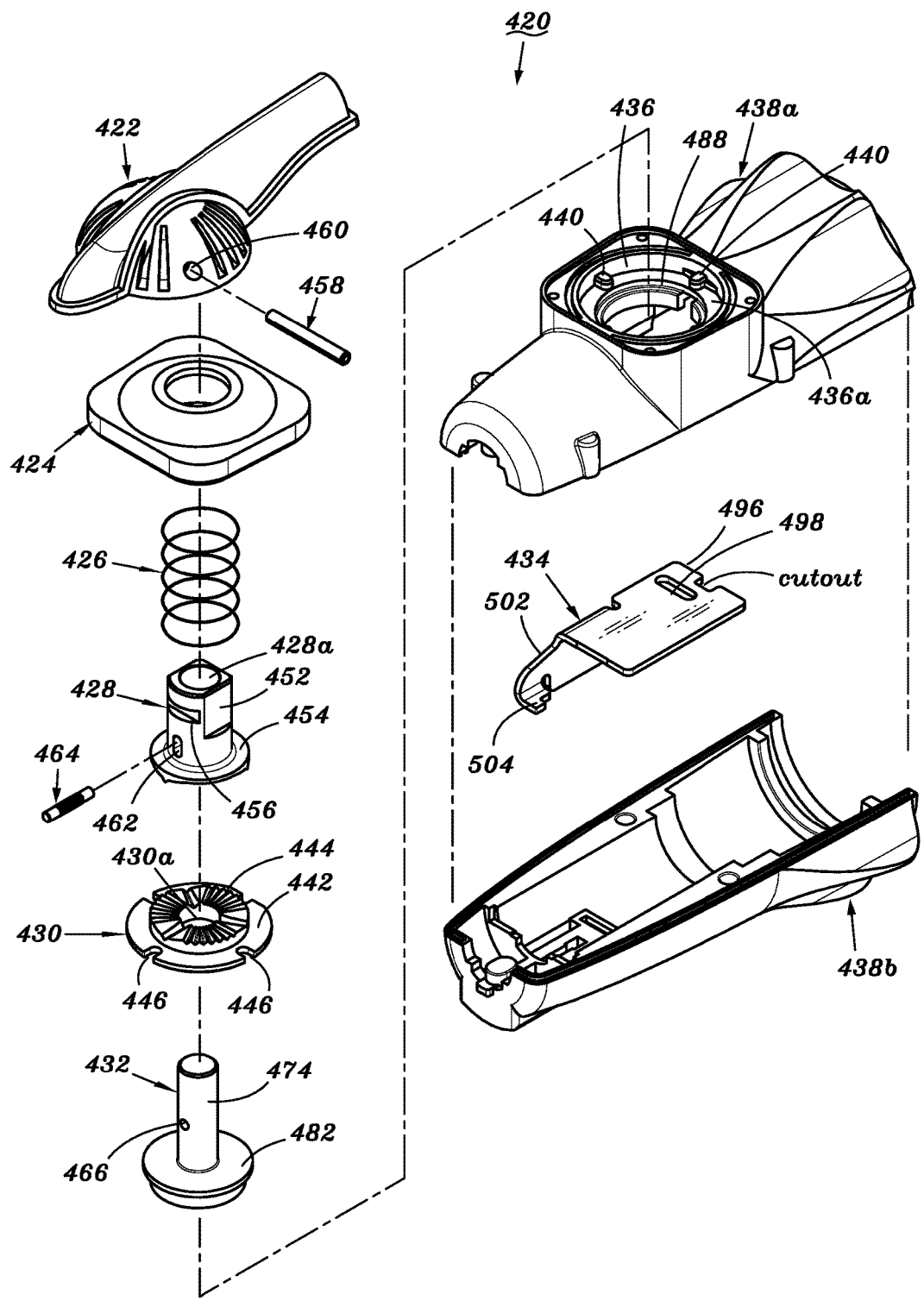
FIG. 65 is a perspective view of the articulation mechanism shown in FIG. 64 with parts separated.

FIGS. 64-80 illustrate another embodiment of the presently disclosed articulation mechanism shown generally as 420. Referring to FIGS. 64 and 65, articulation mechanism 420 includes an articulation lever 422, a mechanism cover 424, a biasing member 426, an upper clutch 428, a lower clutch 430, a main shaft 432, a translation member 434, and a cam member 480. The entire articulation mechanism is supported in a receptacle 436 formed in the top half-section 438a of rotatable member 438 but may also be supported in the handle assembly. Receptacle 436 defines a substantially cylindrical throughbore having a shoulder 436a dimensioned to receive and support lower clutch 430. Shoulder 436a includes one or more tabs 440.

Figure 66:
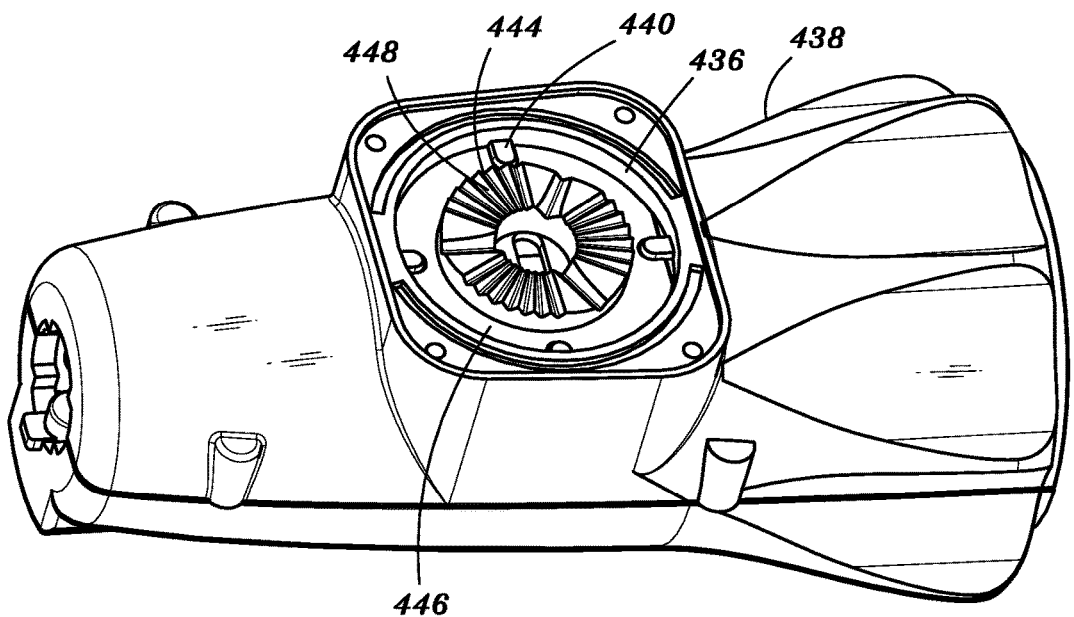
FIG. 66 is a perspective view of the rotatable member of the articulation mechanism shown in FIG. 64 with the lower clutch positioned in the receptacle of the rotatable member.
Figure 70:
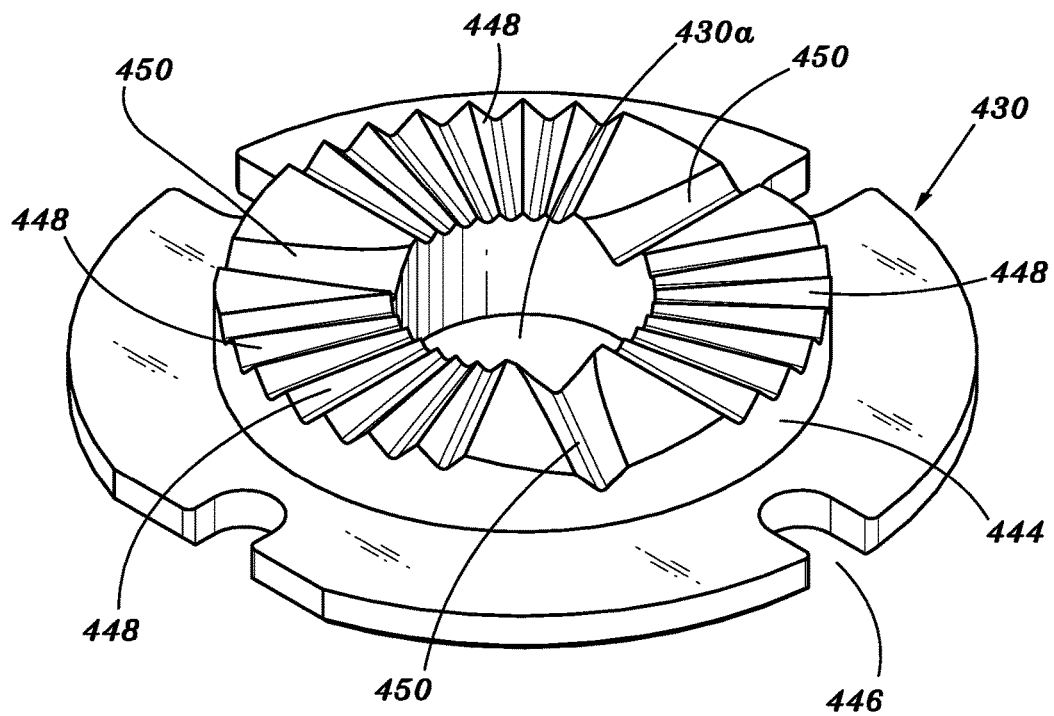
FIG. 70 is a top perspective view of the lower clutch of the articulation mechanism shown in FIG. 65.

Referring also to FIGS. 66 and 70, lower clutch 430 includes an outer rim portion 442 and an inner circular serrated portion 444. Outer rim portion 442 includes one or more cutouts 446 which are dimensioned to receive tabs 440 on shoulder 436a of receptacle 436. Lower clutch 430 is positioned within receptacle 436 atop shoulder 436a such that tabs 440 are received within cutouts 446 and lower clutch 430 is prevented from rotating within receptacle 436 (FIG. 66). Circular serrated portion 444 includes a series of shallow serrations 448 and three spaced deep serrations 450 (FIG. 70). These serrations 448 and 450 include angled walls and function to retain articulation lever 422 at a plurality of different articulated positions as will be discussed in further detail below. Lower clutch 430 also defines a central throughbore 430a which is dimensioned to receive main shaft 432.

Referring to FIGS. 65, 68 and 69, upper clutch 428 includes a hub portion 452 and a base portion 454. Hub portion 452 defines a central throughbore 428a and a channel 456 which is dimensioned to receive a pin 458. Pin 458 is inserted through an opening 460 in articulation lever 422 and into channel 456 to rotatably fix articulation lever 422 to upper clutch 428. Hub portion 422 also includes an elongated slot 462 which is dimensioned to receive a pin 464. Pin 464 is inserted through slot 462 and a hole 466 formed in main shaft 432 to rotatably fix upper clutch 428 to main shaft 432. Pin 464 is longitudinally slidable in slot 462 to allow upper clutch 428 to move axially in relation to main shaft 432.

Base portion 454 of upper clutch includes an upper face 469 and a lower face 468 (FIG. 68) which is positioned in juxtaposed alignment with serrated portion 444 of lower clutch 430. Lower face 468 includes a plurality of spaced projections 470 configured to be received within deep and shallow serrations 450 and 448 of lower clutch 430. In one embodiment, projections 470 have a triangularly shaped cross-section in which the walls defining the triangle are steeper near the apex of the triangle. Such a configuration allows the apex of projections 470 to be received in shallow serrations 448 and substantially the entire projection 470 to be received in deep serrations 450, thus effecting a more secure engagement. The shape of projections 470 has two portions and two different engagement surfaces to define two different vertical positions for the mechanism.

Referring to FIGS. 65, 71 and 72, main shaft 432 includes a substantially cylindrical body portion 474 and a disc-shaped base portion 476. Base portion 476 defines a cutout 478 (FIG. 72) and includes a cam member or protrusion 480. Base portion 476 defines an annular support surface 482 (FIG. 71). Body portion 474 is dimensioned to extend through central throughbore 430a of lower clutch 430 and central throughbore 428a of upper clutch 428 such base portion 476 is positioned beneath upper clutch 428 and lower clutch 430 within receptacle 436 of rotatable member 438. Base portion 476 also includes a stepped portion 484 defining a shoulder 486. Shoulder 486 is supported on an annular shelf 488 (FIG. 65) formed in receptacle 436 such that main shaft 432 is rotatably supported within receptacle 436 of rotatable member 438.

Referring to FIGS. 65, 73 and 74, mechanism cover 424 defines an opening 490 dimensioned to allow passage of hub portion 452 of upper clutch 428 such that hub portion 452 can be rotatably fixed to articulation lever 422. An inner cylindrical portion 492 (FIG. 74) of cover 424 includes cutouts 494. When cover 424 is placed over receptacle 436 of top half section 438a of rotatable member 438, cutouts 494 of cylindrical portion 492 of cover 424 receive tabs 440 and cylindrical portion 492 compresses lower clutch 430 against shoulder 436a (FIG. 65). Cover 424 can be secured to rotatable member using any known fastening technique including welding, adhesives or any known mechanical attachment structure, e.g., screws, rivets, etc.

Referring to FIG. 65, translation member 434 includes an angled body 496 which defines a cam slot 498, a cutout 500 and an arm 502 having engagement structure 504 configured to engage a proximal end of an articulation link 123 (FIG. 10A). Although the engagement structure 504 is illustrated as a finger-like projection other mating engagement structures are envisioned to facilitate connection of translation member 434 to articulation link 123 (FIG. 10A).

Figure 67:
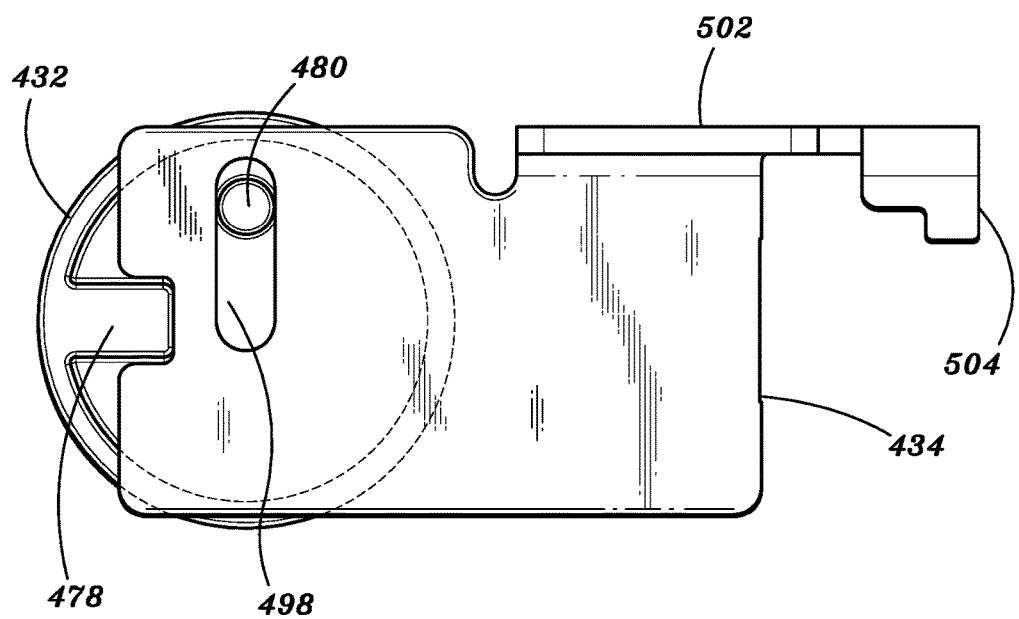
FIG. 67 is a bottom view of the cam member, main shaft and translation member of the articulation mechanism shown in FIG. 65.

Referring also to FIG. 67, cam slot 498 of translation member 434 is dimensioned to slidably receive cam member 480 of main shaft 432. As discussed above, articulation lever 422 is rotatably fixed to upper clutch 428 and upper clutch 428 is rotatably fixed to body portion 474 of main shaft 432. Thus, when articulation lever 422 is rotated, upper clutch 428, main shaft 432, and cam member 480 rotate in relation to translation member 434. Although not shown, translation member 434 is confined to linear movement within rotatable member 438. As such, when cam member 480 is driven in rotation, translation member 434 is forced to move linearly within rotatable member 438. Since translation member 438 is fastened to articulation link 123 (FIG. 10A), linear movement of translation member 438 effects linear movement of articulation link 123 to articulate tool assembly 17.

Figure 75:
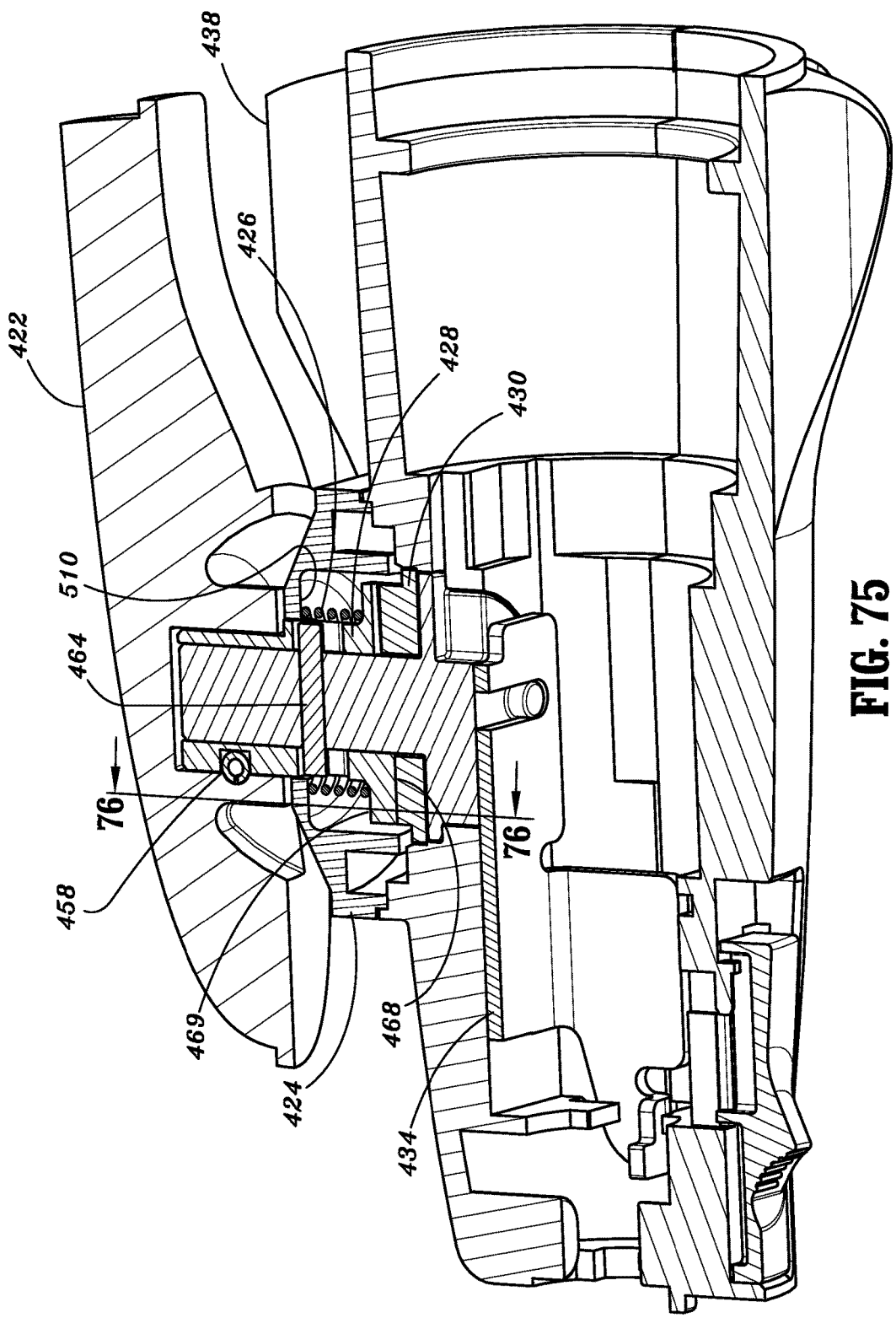
FIG. 75 is a cross-sectional view of the articulation mechanism shown in FIG. 64 with the articulation mechanism in a non-articulated position.
Figure 76:
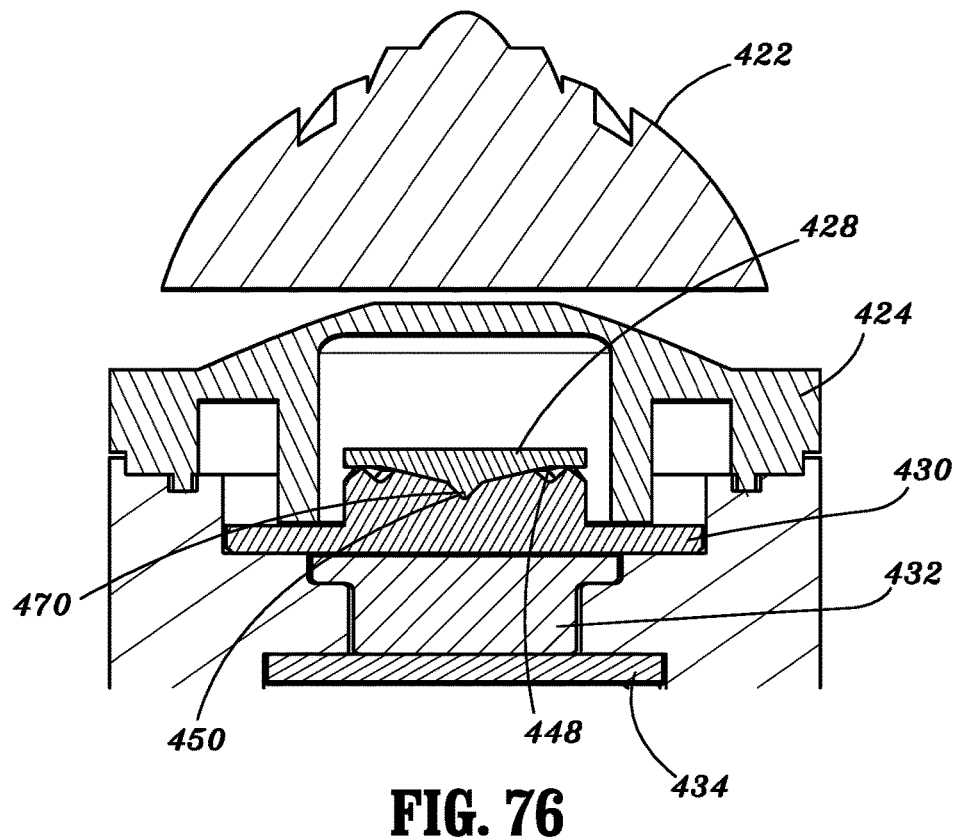
FIG. 76 is a cross-sectional view taken along section lines 76-76 of FIG. 75.
Figure 77:
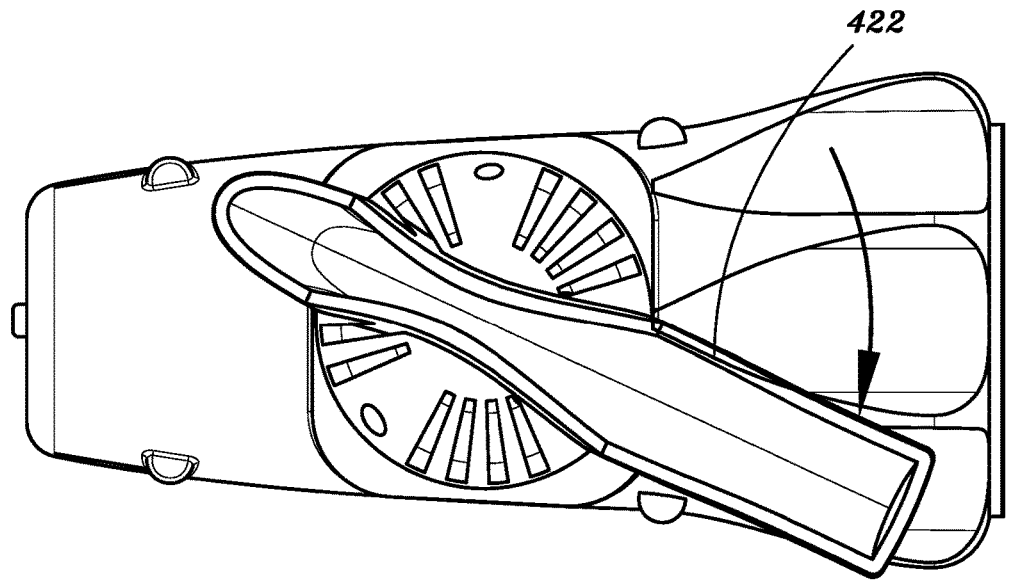
FIG. 77 is a top view of the articulation mechanism shown in FIG. 64 with the articulation lever rotated.
Figure 78:
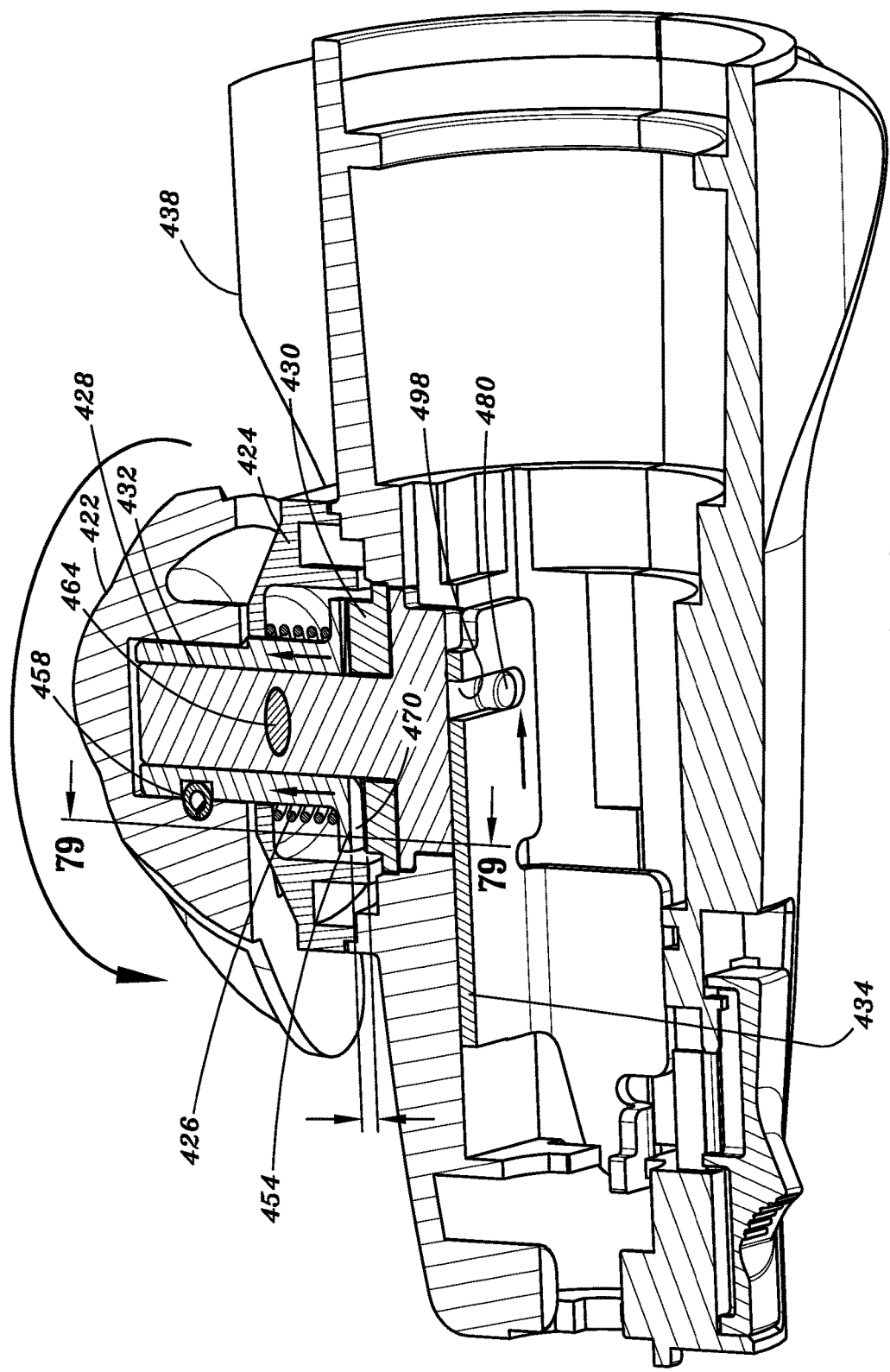
FIG. 78 is a cross-sectional view of the articulation mechanism shown in FIG. 64 with the articulation lever rotated as shown in FIG. 77.

Referring now to FIGS. 65 and 75, biasing member 426 is positioned between upper face 469 of base portion 454 of upper clutch 428 and an inner surface 510 of cover 424. Biasing member urges lower face 468 (FIG. 68) of upper clutch 428 into engagement with serrated portion 444 (FIG. 70) of lower clutch 430 such that spaced projections 470 on upper clutch 428 are received within shallow serrations 448 or deep serrations 450 of lower clutch 430. Engagement between projections 470 and serrations 448 and 450 releasably secure articulation mechanism 420 in a fixed position to thereby releasably secure a tool assembly 17 (FIG. 1) at a fixed angle of articulation. See FIG. 76.

Referring to FIGS. 77-80, when articulation lever 422 is rotated, (as discussed above) upper clutch 428 and main shaft 432 are driven in rotation. When base portion 454 of upper clutch 428 is rotated in relation to serrated portion 444 of lower clutch 428, the triangular projections 470 are driven against angled serrations 448 and 450. When this occurs, upper clutch 428 is urged upwardly against the bias of biasing member 426 (FIG. 78) to disengage projections 470 from serrations 448 or 450 (FIG. 79), to allow rotation of upper clutch 428, and thus, main shaft 432. Thereafter, biasing member 426 urges upper clutch downwardly to urge projection 470 back into engagement with the next serration (FIG. 80). It is noted, projections 470 are positioned to be received within deep serrations 450 when tool assembly 17 (FIG. 1) is in its non-articulated position aligned with body portion 14 (FIG. 1). This provides increased resistance to movement of tool assembly 17 from its non-articulated position. Desirably, the deep serrations 450 correspond to the non-articulated position of the tool assembly 17. However, deep serrations may be incorporated into the mechanism to provide other positions with increased resistance to movement.

Figure 70A:
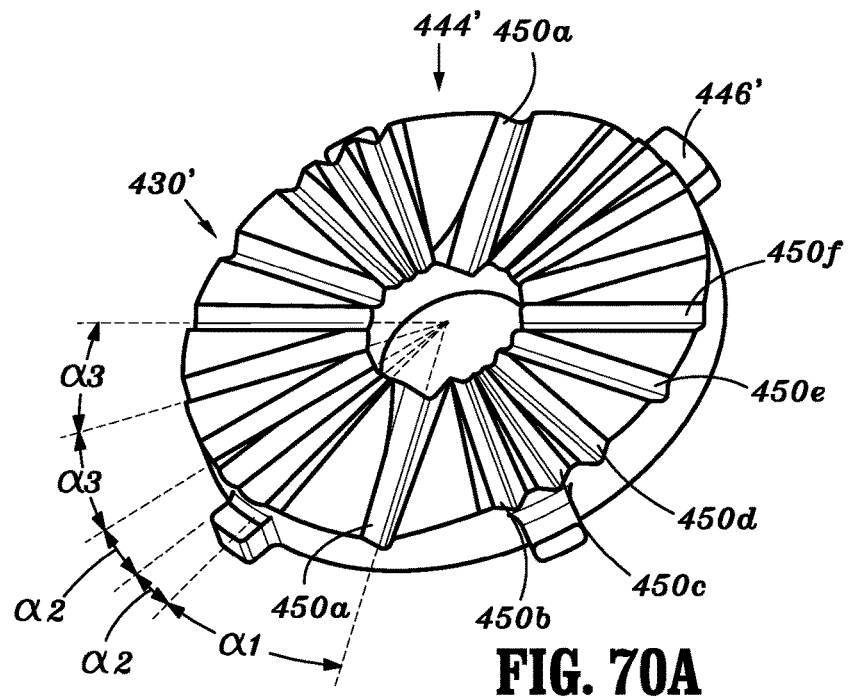
FIG. 70A is a top perspective view of a lower clutch according to an alternate embodiment of the present disclosure.

With reference to FIGS. 68A and 70A, another embodiment of an upper clutch 428' and a lower clutch 430', respectively, is illustrated. In this embodiment, upper clutch 428' includes a lower face 468' which is positioned in juxtaposed alignment with a serrated portion 444' of lower clutch 430'. Lower face 468' includes two spaced projections 470' configured to be received within serrations 450a-450f of lower clutch 430'.

As shown, serrations 450a-450f are symmetrically disposed in quadrants (i.e., about two axes) about lower clutch 430'. A first axis of symmetry extends between an opposing pair of serrations 450a-450a; a second axis of symmetry, which is off-set 90° from the first axis of symmetry, extends between an opposing pair of serrations 450f-450f. As such, there are two of each serrations 450a and 450f, and there are four of each serrations 450b-450e. The orientation of projections 470' and serrations 450a-450f help provide articulation lever 422 with a 90° range of rotation.

With particular regard to FIG. 70A, the spacing and the corresponding angle between some adjacent serrations is substantially equal, and the spacing between other adjacent serrations is non-equal. In particular, the space and corresponding angle between adjacent serrations 450b, 450c, and 450d is substantially equal, and the space and corresponding angle between adjacent serrations 450d, 450e and 450f is substantially equal. The space and angle between adjacent serrations 450a and 450b is greater than the space and angle between adjacent serrations 450d and 450e, which is greater than the spacing and angles between adjacent serrations 450b and 450c. More particularly, for example, an angle α1 between valleys of adjacent serrations 450a and 450b may be between about 25° and about 35°, and may be equal to about 30°; an angle α2 between valleys of adjacent serrations 450b and 450c, and 450c and 450d may be between about 5° and about 15°, and may be equal to about 10°; and an angle α3 between valleys of adjacent serrations 450d and 450e, and 450e and 450f may be between about 15° and about 25°, and may be equal to about 20°. In the illustrated embodiment, lower clutch 430' includes exactly twenty serrations.

As can be appreciated, the amount of torque that must be exerted to move projections 470' via articulation lever 422 between relatively closely-spaced serrations (e.g., 450b and 450c) is larger than the amount of torque necessary to move projections 470' between adjacent serrations that are farther apart (e.g., 450a and 450b). The tool assembly 17 has a greater resistance to moment in articulation as the tool assembly 17 approaches 90 degrees of articulated movement. Drive beam 266 bends as the tool assembly 17 is articulated, and the greater degree of articulation, the greater force required to bend the drive beam 266 to further articulate the tool assembly 17.

With continued reference to FIG. 70A, lower clutch 430' includes a plurality of tabs 446' which are dimensioned to receive corresponding slots or grooves (not shown) on the shoulder of receptacle 436. As can be appreciated, the interaction between tabs 446' and the corresponding slots help prevent rotation movement of lower clutch 430' with respect to receptacle 436. It is envisioned that at least one tab is differently-sized from at least one other tab to help ensure proper angular placement of lower clutch 430' within receptacle 436. Additionally or alternatively, it is envisioned that adjacent tabs 446' and corresponding slots are spaced at a non-90° angle from one other, which also helps ensure proper angular placement of lower clutch 430' within receptacle 436. Further, tabs 446' help ensure proper placement of lower clutch 430' within receptacle 436, and also help ensure that lower clutch 430' is not positioned up-side-down within receptacle 436.

Referring to FIGS. 8-10 and 16, a disposable loading unit sensing mechanism extends within stapling apparatus 10 from elongated body 14 into handle assembly 12. The sensing mechanism includes a sensor tube 176 which is slidably supported within bore 26 of elongated body 14. The distal end of sensor tube 176 is positioned towards the distal end of elongated body 14 and the proximal end of sensor tube 176 is secured within the distal end of a sensor cylinder 176 via a pair of nubs 180. The distal end of a sensor link 182 is secured to the proximal end of sensor cylinder 178. Sensor link 182 (See FIGS. 8a and 8c) has a bulbous end 184 which engages a camming surface 83a on pivotable locking member 83. When a disposable loading unit (not shown) is inserted in the distal end of elongated body 14, the disposable loading unit engages the distal end 177 of sensor tube 176 to drive sensor tube 176 proximally, and thereby drive sensor cylinder 178 and sensor link 182 proximally. Movement of sensor link 182 proximally causes bulbous end 184 of sensor link 182 to move distally of camming surface 83a to allow locking member 83 to pivot under the bias of spring 92 from a position permitting firing of stapling apparatus 10 to a blocking position, wherein blocking member 83 is positioned to engage actuation shaft 46 and prevent firing of stapling apparatus 10. Sensor link 182 and locking member 83 function to prevent firing of surgical instrument 10 after a disposable loading unit has been secured to elongated body 14, without first operating firing lockout assembly 80. It is noted that movement of link 182 proximally permits locking member 83 to move to its position shown in FIG. 5.

Figure 12A:
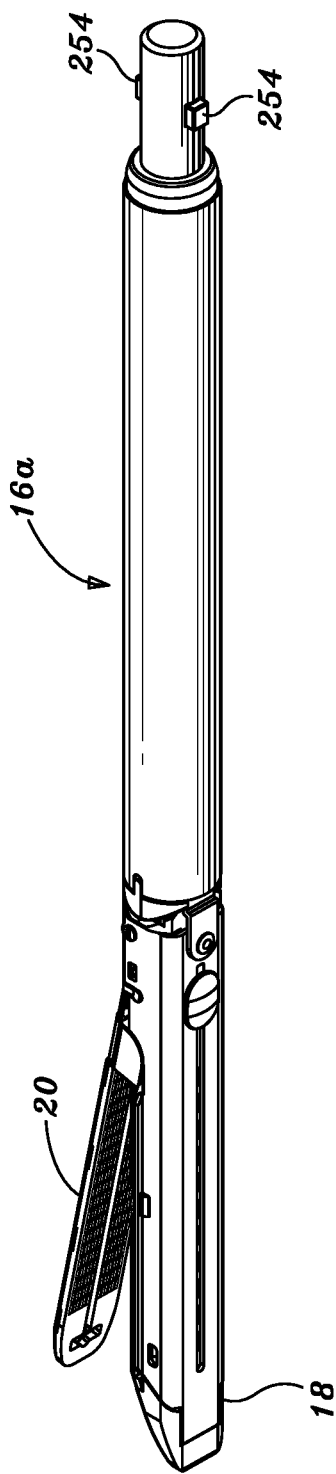
FIG. 12a is a perspective view of a non-articulating disposable loading unit usable with the surgical instrument shown in FIG. 1.
Figure 12B:
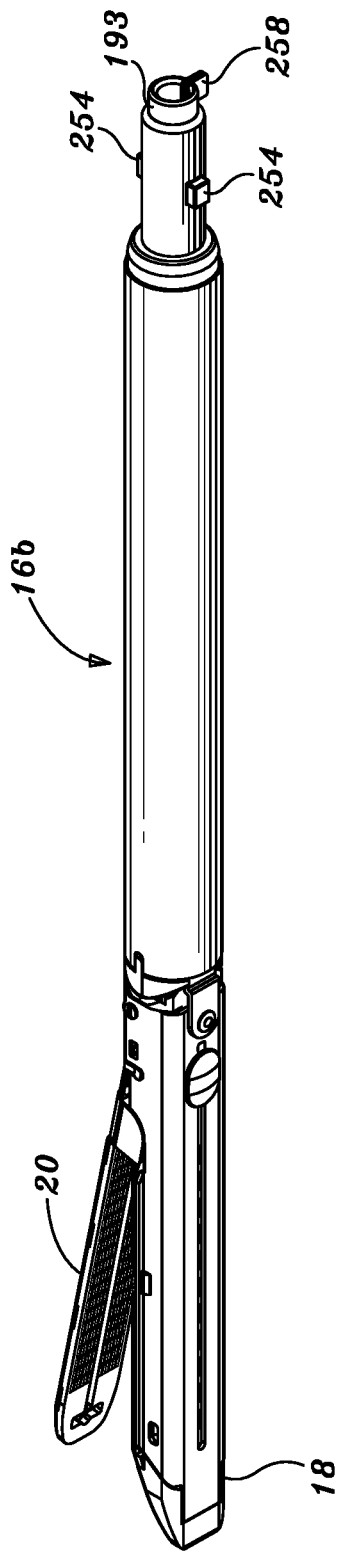
FIG. 12b is a perspective view of the preferred articulating disposable loading unit of the surgical instrument shown in FIG. 1.

Referring again to FIGS. 9-12, cam member 136 includes recess 154. A locking ring 184 having a nub portion 186 configured to be received within recess 154 is positioned about sensor cylinder 178 between a control tab portion 188 and a proximal flange portion 190. A spring 192 positioned between flange portion 190 and locking ring 184 urges locking ring distally about sensor cylinder 178. When an articulating disposable loading unit 16b having an extended insertion tip 193 is inserted into the distal end of elongated body 14 of stapling apparatus 10, insertion tip 193 causes tab portion 188 to move proximally into engagement with locking ring 184 to urge locking ring 184 and nub 186 proximally of recess 154 in cam member 136 (See FIG. 12b). With nub 186 positioned proximally of recess 154, cam member 136 is free to move transversely to effect articulation of stapling apparatus 10. A non-articulating disposable loading unit does not have an extended insertion tip (See FIG. 12a). As such, when a non-articulating disposable loading unit is inserted in elongated body 14, sensor cylinder 178 is not retracted proximally a sufficient distance to move nub 186 from recess 154. Thus, cam member 136 is prevented from moving transversely by nub 186 of locking ring 184 which is positioned in recess 154 and articulation lever 30 is locked in its central position.

Figure 16:
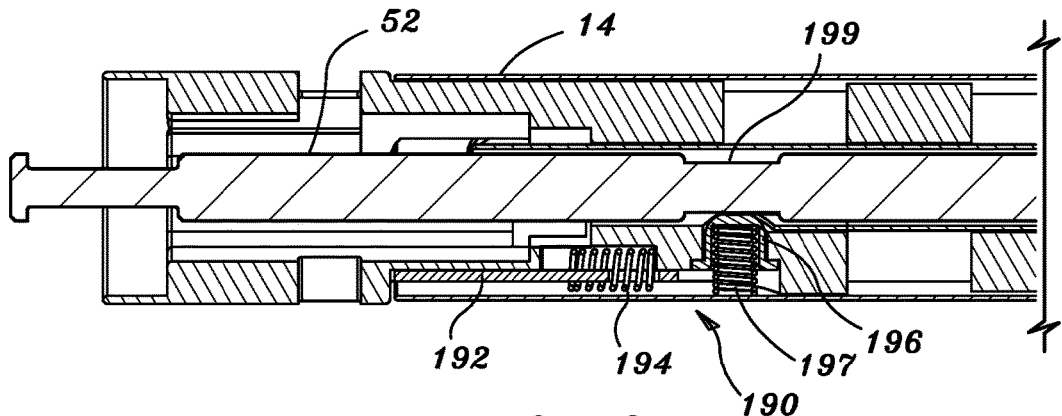
FIG. 16 is an enlarged view of the indicated area of detail shown in FIG. 8.
Figure 17:
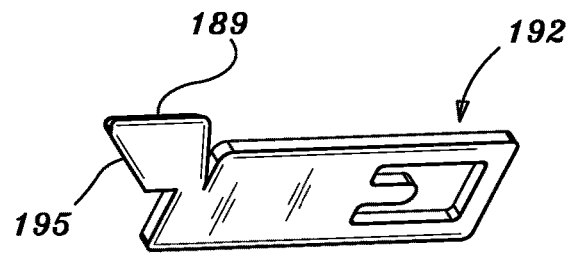
FIG. 17 is a side perspective view of the blocking plate of the surgical instrument shown in FIG. 1.
Figure 18:
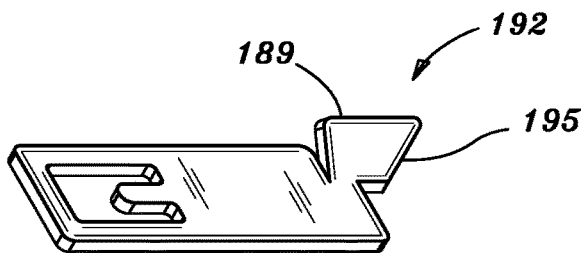
FIG. 18 is a top perspective view of the blocking plate of the surgical instrument shown in FIG. 1.
Figure 21:
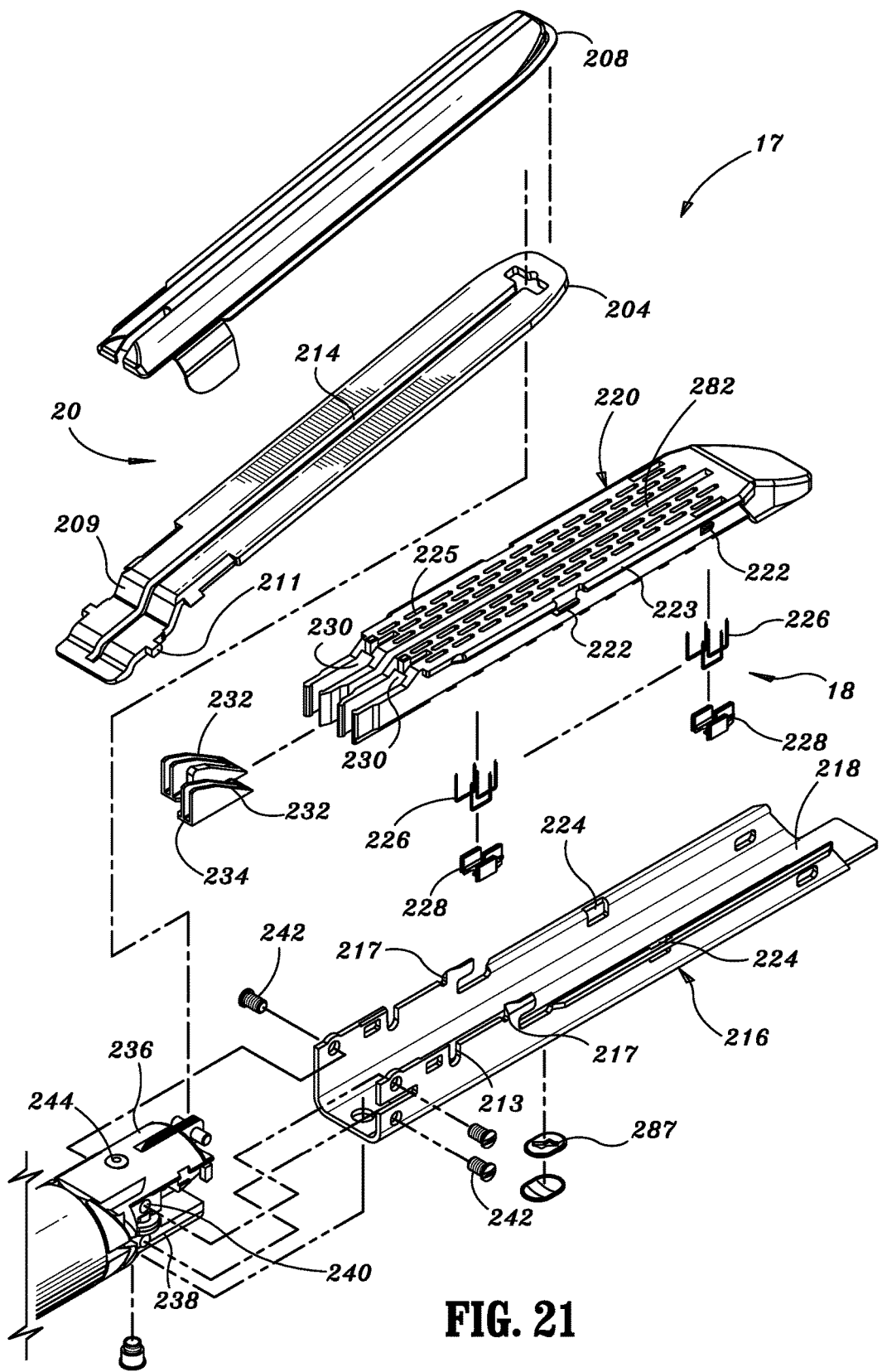
FIG. 21 is a perspective view of the tool assembly of the surgical instrument of FIG. 1 with parts separated.
Figure 22:
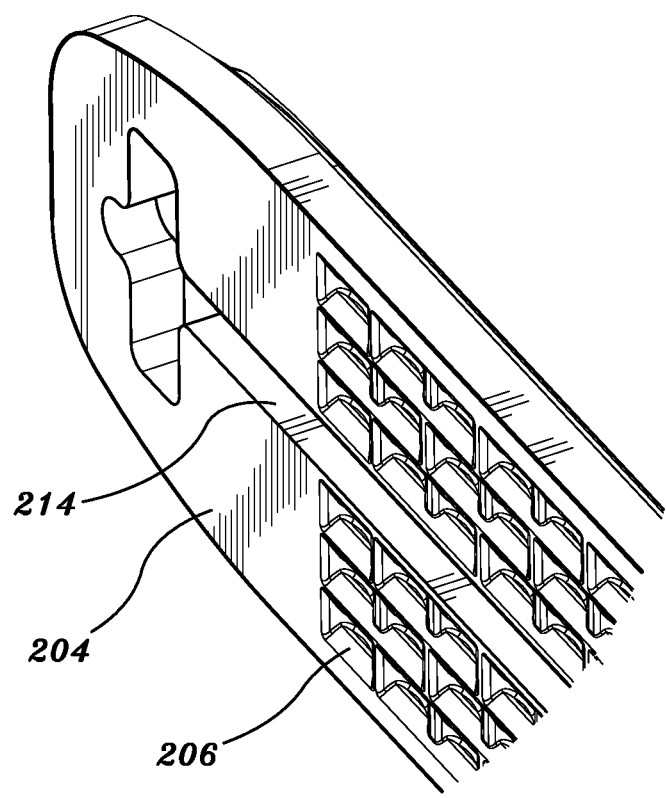
FIG. 22 is an enlarged perspective view of the distal end of the anvil assembly showing a plurality of staple deforming cavities.
Figure 23:
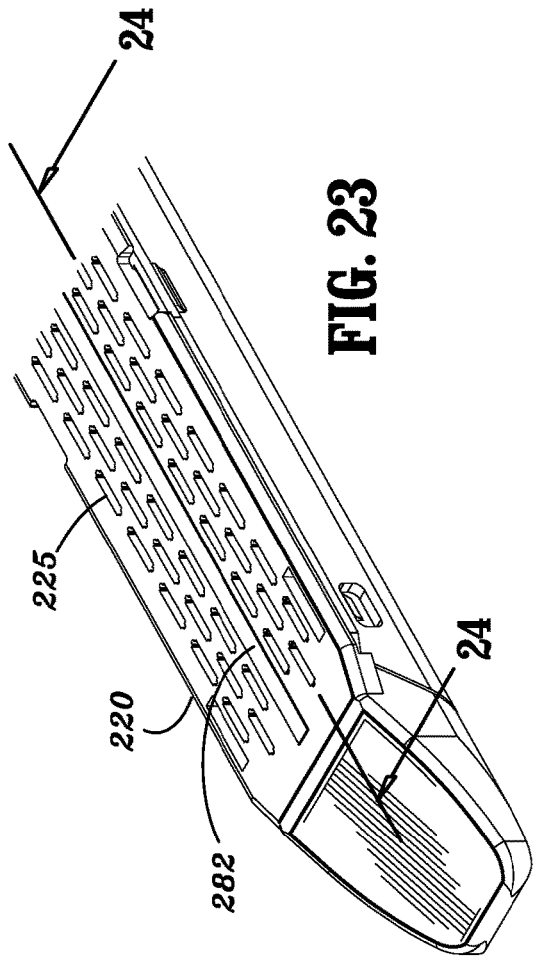
FIG. 23 is an enlarged perspective view of the distal end of the staple cartridge of the surgical instrument shown in FIG. 1.
Figure 24:
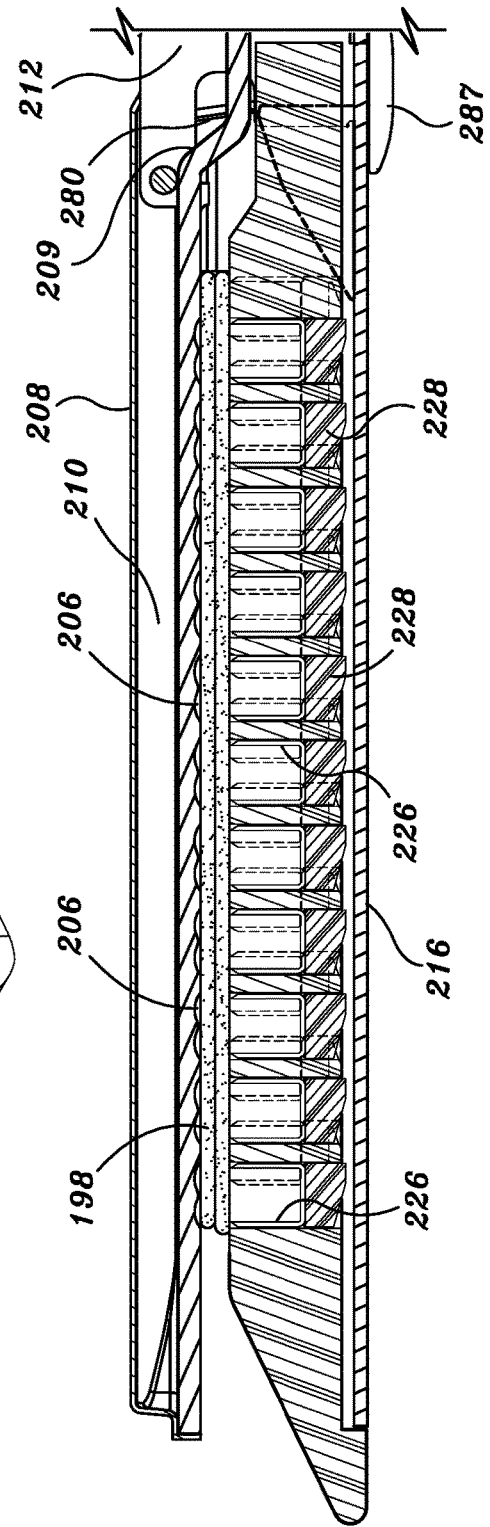
FIG. 24 is a side cross-sectional view taken along section line 24-24 of FIG. 23.

Referring to FIGS. 16-18, the distal end of elongated body 14 includes a control rod locking mechanism 190 which is activated during insertion of a disposable loading unit into elongated body 14. Control rod locking mechanism 190 includes a blocking plate 192 which is biased distally by a spring 194 and includes a proximal finger 189 having angled cam surface 195. A semi-circular engagement member 196 is biased transversely towards control rod 52 by a spring 197. Control rod 52 includes an annular recess 199 configured to receive engagement member 196. Blocking plate 192 is movable from a distal position spaced from engagement member 196 to a proximal position located behind engagement member 196. In the proximal position, engagement member 196 is prevented from being biased from recess 199 by engagement with blocking plate 192. During insertion of a disposable loading unit 16 (See FIG. 1) into the distal end of elongated body 14, as will be described in further detail below, cam surface 195 of blocking plate 192 is engaged by a nub 254 (FIG. 30) on the disposable loading unit 16 as the disposable loading unit is rotated into engagement with elongated body 14 to urge plate 192 to the proximal position. Engagement member 196, which is positioned within recess 199, is retained therein by blocking plate 192 while nub 254 engages cam surface 195 to prevent longitudinal movement of control rod 52 during assembly. When the disposable loading unit 16 is properly positioned with respect to the elongated body 14, nub 254 on the proximal end of the disposable loading unit 16 passes off cam surface 195 allowing spring 194 to return blocking plate 192 to its distal position to permit subsequent longitudinal movement of control rod 52. It is noted that when the disposable loading unit nub passes off cam surface 195, an audible clicking sound is produced indicating that the disposable loading unit 16 is properly fastened to the elongated body 14.

Referring to FIGS. 19 and 20, disposable loading unit 16 includes a proximal housing portion 200 adapted to releasably engage the distal end of body portion 14 (FIG. 1). A mounting assembly 202 is pivotally secured to the distal end of housing portion 200, and is configured to receive the proximal end of tool assembly 17 such that pivotal movement of mounting assembly 202 about an axis perpendicular to the longitudinal axis of housing portion 200 effects articulation of tool assembly 17.

Referring to FIGS. 21-26, tool assembly 17 preferably includes anvil assembly 20 and cartridge assembly 18. Anvil assembly 20 includes anvil portion 204 having a plurality of staple deforming concavities 206 (FIG. 22) and a cover plate 208 secured to a top surface of anvil portion 204 to define a cavity 210 (FIG. 24) therebetween. Cover plate 208 is provided to prevent pinching of tissue during clamping and firing of stapling apparatus 10. Cavity 210 is dimensioned to receive a distal end of an axial drive assembly 212 (See FIG. 27). A longitudinal slot 214 extends through anvil portion 204 to facilitate passage of retention flange 284 of axial drive assembly 212 into the anvil cavity 210. A camming surface 209 formed on anvil portion 204 is positioned to engage axial drive assembly 212 to facilitate clamping of tissue 198. A pair of pivot members 211 formed on anvil portion 204 are positioned within slots 213 formed in carrier 216 to guide the anvil portion between the open and clamped positions. A pair of stabilizing members 215 engage a respective shoulder 217 formed on carrier 216 to prevent anvil portion 204 from sliding axially relative to staple cartridge 220 as camming surface 209 is deformed.

Cartridge assembly 18 includes a carrier 216 which defines an elongated support channel 218. Elongated support channel 218 is dimensioned and configured to receive a staple cartridge 220. Corresponding tabs 222 and slots 224 formed along staple cartridge 220 and elongated support channel 218 function to retain staple cartridge 220 within support channel 218. A pair of support struts 223 formed on staple cartridge 220 are positioned to rest on side walls of carrier 216 to further stabilize staple cartridge 220 within support channel 218.

Staple cartridge 220 includes retention slots 225 for receiving a plurality of fasteners 226 and pushers 228. A plurality of spaced apart longitudinal slots 230 extend through staple cartridge 220 to accommodate upstanding cam wedges 232 of actuation sled 234. A central longitudinal slot 282 extends along the length of staple cartridge 220 to facilitate passage of a knife blade 280. During operation of surgical stapler 10, actuation sled 234 translates through longitudinal slots 230 of staple cartridge 220 to advance cam wedges 232 into sequential contact with pushers 228, to cause pushers 228 to translate vertically within slots 224 and urge fasteners 226 from slots 224 into the staple deforming cavities 206 of anvil assembly 20.

Figure 27:
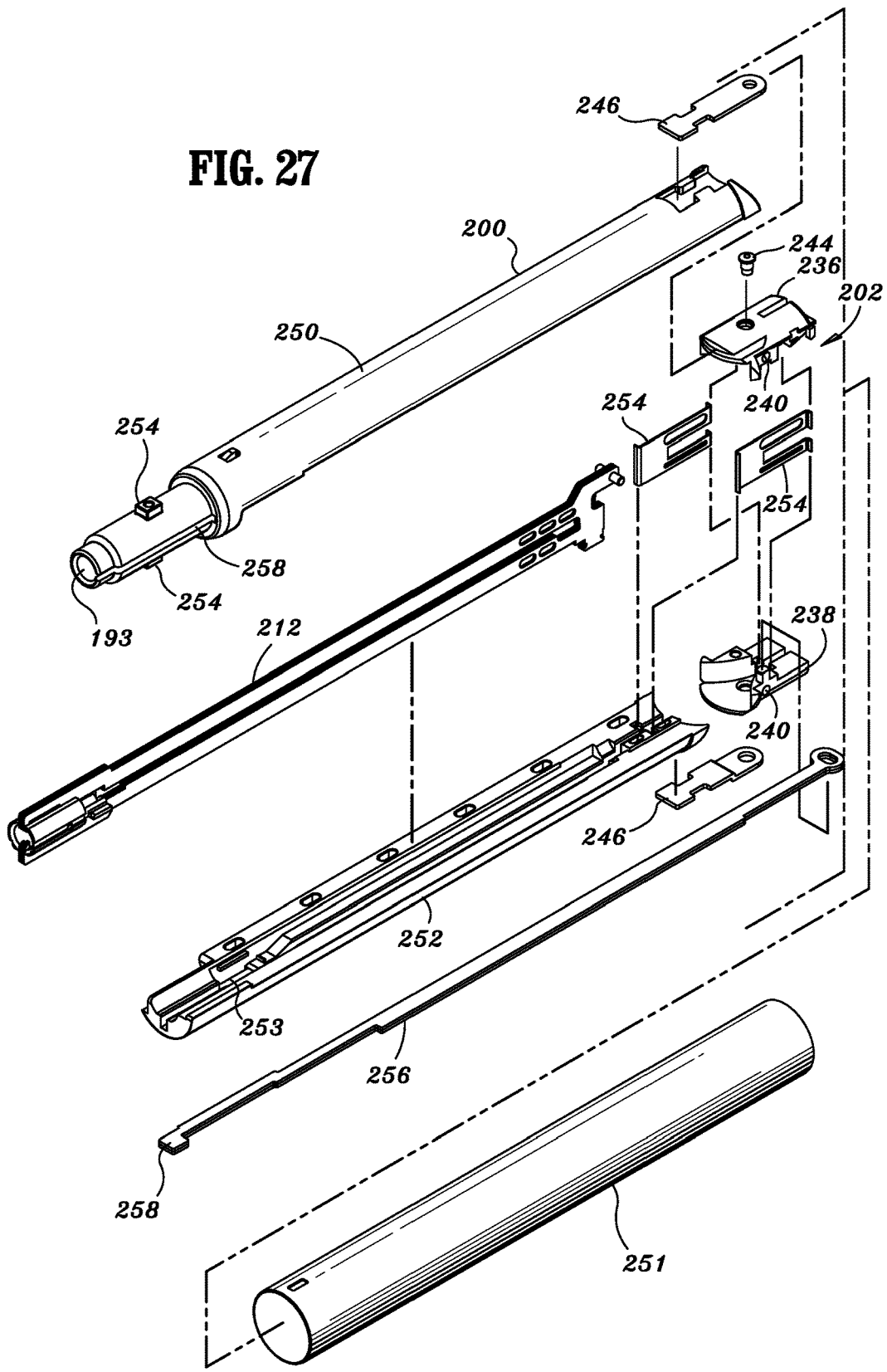
FIG. 27 is an enlarged perspective view with parts separated of the proximal housing portion and mounting assembly of the disposable loading unit shown in FIG. 19.
Figure 31:
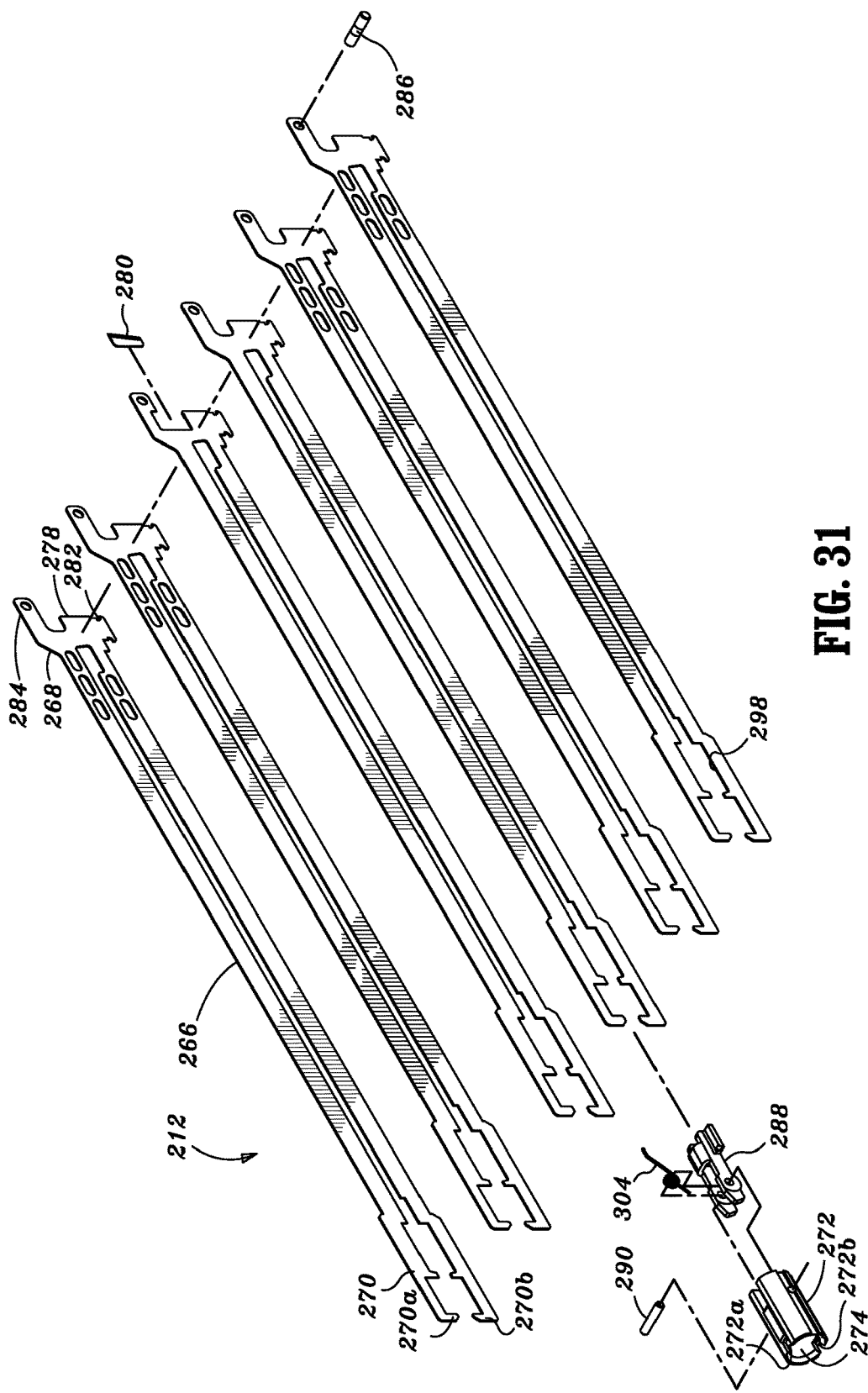
FIG. 31 is a perspective view with parts separated of the axial drive assembly.
Figure 38:
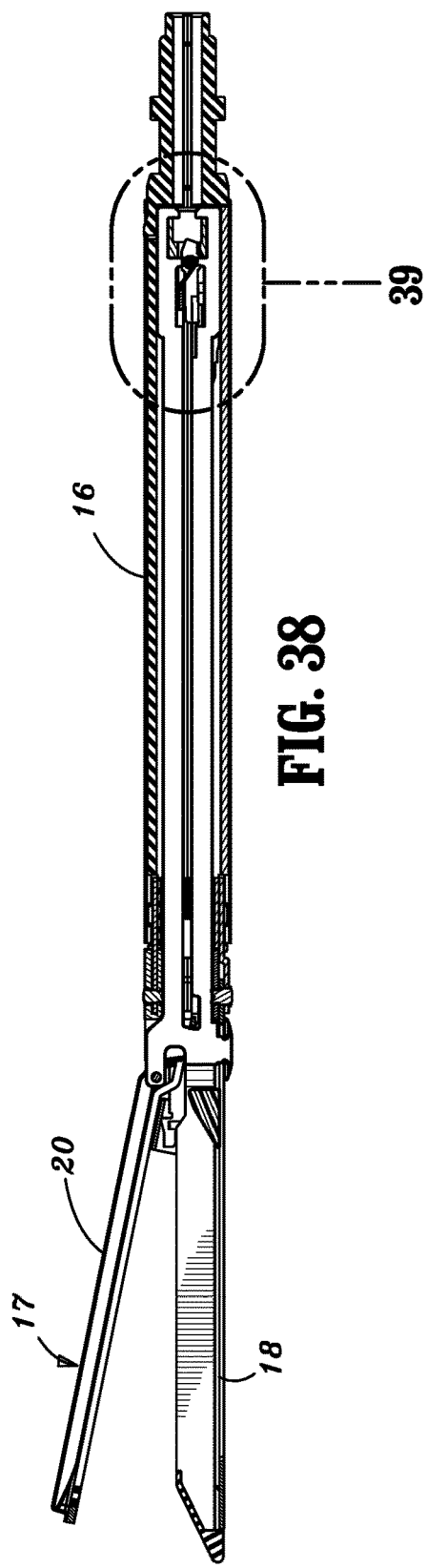
FIG. 38 is a side cross-sectional view of the disposable loading unit shown in FIG. 20.

Referring to FIGS. 27 and 28, mounting assembly 202 includes upper and lower mounting portions 236 and 238. Each mounting portion includes a threaded bore 240 on each side thereof dimensioned to receive threaded bolts 242 (See FIG. 21) for securing the proximal end of carrier 216 thereto. A pair of centrally located pivot members 244 (See FIG. 21) extends between upper and lower mounting portions via a pair of coupling members 246 which engage the distal end of housing portion 200. Coupling members 246 each include an interlocking proximal portion 248 configured to be received in grooves 250 formed in the proximal end of housing portion 200 to retain mounting assembly 202 and housing portion 200 in a longitudinally fixed position in relation thereto.

Housing portion 200 of disposable loading unit 16 includes an upper housing half 250 and a lower housing half 252 contained within an outer casing 251. The proximal end of housing half 250 includes engagement nubs 254 for releasably engaging elongated body 14 and an insertion tip 193. Nubs 254 form a bayonet type coupling with the distal end of body 14 which will be discussed in further detail below. Housing halves 250 and 252 define a channel 253 for slidably receiving axial drive assembly 212. A second articulation link 256 is dimensioned to be slidably positioned within a slot 258 formed between housing halves 250 and 252. A pair of blow out plates 254 are positioned adjacent the distal end of housing portion 200 adjacent the distal end of axial drive assembly 212 to prevent outward bulging of drive assembly 212 during articulation of tool assembly 17.

Referring to FIGS. 29-30, second articulation link 256 includes at least one elongated metallic plate. Preferably, two or more metallic plates are stacked to form link 256. The proximal end of articulation link 256 includes a hook portion 258 configured to engage first articulation link 123 (See FIG. 9) and the distal end includes a loop 260 dimensioned to engage a projection 262 formed on mounting assembly 202. Projection 262 is laterally offset from pivot pin 244 such that linear movement of second articulation link 256 causes mounting assembly 202 to pivot about pivot pins 244 to articulate tool assembly 17.

Referring also to FIGS. 31-34, axial drive assembly 212 includes an elongated drive beam 266 including a distal working head 268 and a proximal engagement section 270. Drive beam 266 may be constructed from a single sheet of material or, preferably, multiple stacked sheets. Engagement section 270 includes a pair of engagement fingers 270a and 270b which are dimensioned and configured to mountingly engage a pair of corresponding retention slots 272a and 272b formed in drive member 272. Drive member 272 includes a proximal porthole 274 configured to receive the distal end 276 of control rod 52 (See FIG. 35) when the proximal end of disposable loading unit 16 is engaged with elongated body 14 of surgical instrument 10.

The distal end of drive beam 266 is defined by a vertical support strut 278 which supports a knife blade 280, and an abutment surface 283 which engages the central portion of actuation sled 234 during a stapling procedure. Surface 285 at the base of surface 283 is configured to receive a support member 287 slidably positioned along the bottom of the staple cartridge 220. Knife blade 280 is positioned to translate slightly behind actuation sled 234 through a central longitudinal slot 282 in staple cartridge 220 (FIG. 30) to form an incision between rows of stapled body tissue. A retention flange 284 projects distally from vertical strut 278 and supports a cylindrical cam roller 286 at its distal end. Cam roller 286 is dimensioned and configured to engage cam surface 209 on anvil body 204 to clamp anvil portion 204 against body tissue.

Referring also to FIGS. 36-39, a locking device 288 is pivotally secured to drive member 270 about a pivot pin 290. Locking device 288 includes a pair of elongate glides 292 and 294 which define a channel 296. A web 298 joins a portion of the upper surfaces of glides 292 and 294, and is configured and dimensioned to fit within elongated slot 298 formed in drive beam 266 at a position distal of drive member 270. Horizontal cams 300 and 302 extend from glides 292 and 294 respectively, and are accommodated along an inner surface of lower housing half 252. As best shown in FIG. 42, a torsion spring 304 is positioned adjacent drive member 270 and engages horizontal cams 300 and 302 of locking device 288 to normally bias locking device 288 downward toward lower housing half 252 onto ledge 310.

Locking device 288 translates through housing portion 200 with axial drive assembly 212. Operation of locking device 288 will be described below.

Sequence of Operation

Referring to FIGS. 40-44, to use stapling instrument 10, a disposable loading unit 16 is first secured to the distal end of elongated body 14. As discussed above, stapling instrument 10 can be used with articulating and non-articulating disposable loading units having linear rows of staples between about 30 mm and about 60 mm. To secure disposable loading unit 16 to elongated body 14, the distal end 276 of control rod 52 is inserted into insertion tip 193 of disposable loading unit 16, and insertion tip 193 is slid longitudinally into the distal end of elongated body 14 in the direction indicated by arrow "A" in FIG. 41 such that hook portion 258 of second articulation link 256 slides within a channel 310 in elongated body 314. Nubs 254 will each be aligned in a respective channel (not shown) in elongated body 14. When hook portion 258 engages the proximal wall 312 of channel 310, disposable loading unit 16 is rotated in the direction indicated by arrow "B" in FIGS. 41-44 to move hook portion 258 of second articulation link 256 into engagement with finger 164 of first articulation link 123. Nubs 254 also forms a bayonet type coupling within annular channel 314 in body 14. During rotation of loading unit 16, nubs 254 engage cam surface 195 (FIG. 41) of block plate 192 to initially move plate 192 in the direction indicated by arrow "C" in FIGS. 41 and 43 to lock engagement member 196 in recess 199 of control rod 52 to prevent longitudinal movement of control rod 52 during attachment of disposable loading unit 16. During the final degree of rotation, nubs 254 disengage from cam surface 195 to allow blocking plate 192 to move in the direction indicated by arrow "D" in FIGS. 42 and 44 from behind engagement member 196 to once again permit longitudinal movement of control rod 52.

Figure 43A:
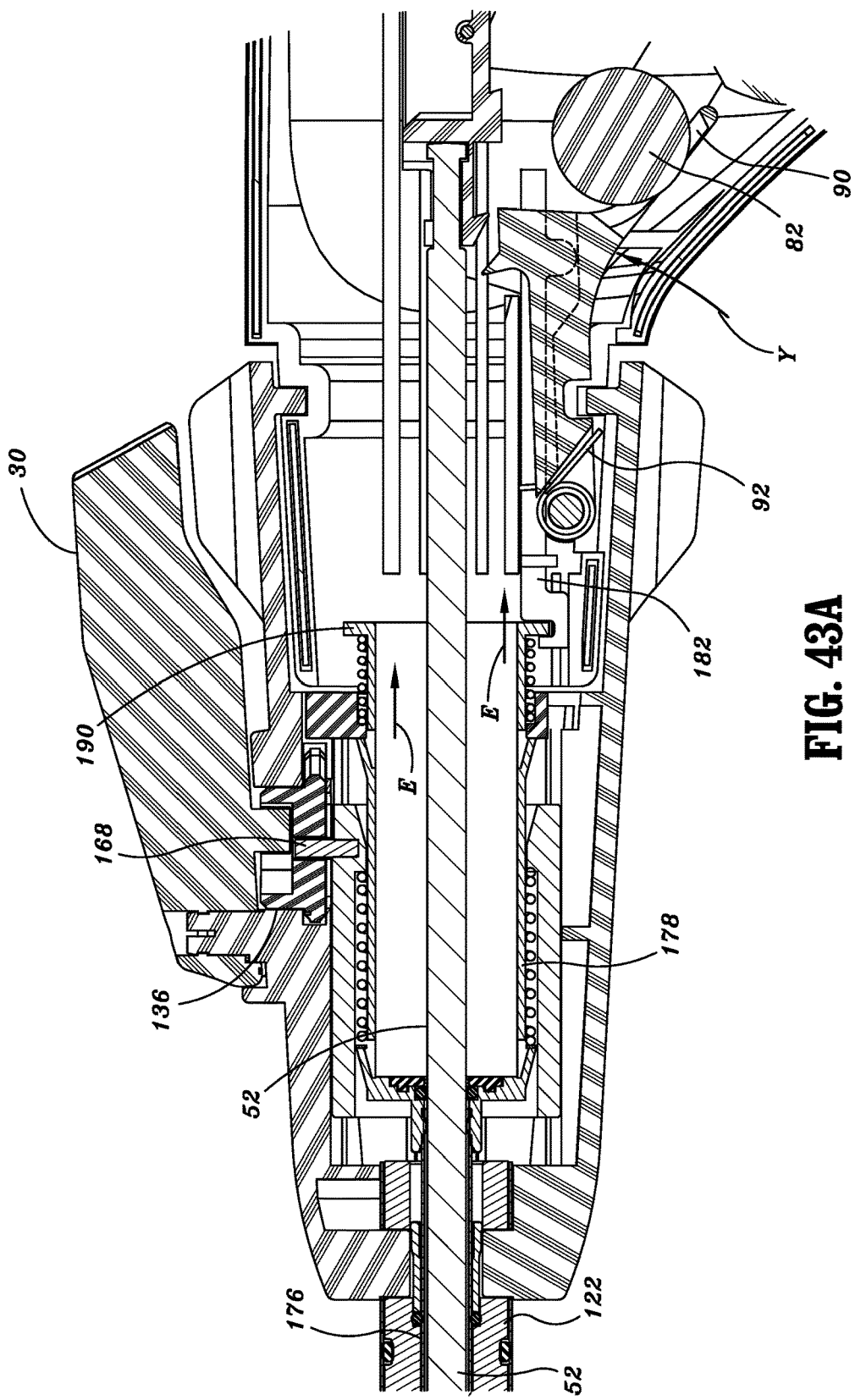
FIG. 43a is a side cross-sectional view of the rotation knob, articulation mechanism, and sensing mechanism during insertion of a disposable loading unit into the elongated body of the surgical instrument.

Referring to FIGS. 43 and 43a, when insertion tip 193 engages the distal end of sensor tube 176, the disposable loading unit sensing mechanism is actuated. Insertion tip 193 engages and moves sensor tube 176 proximally in the direction indicated by arrow "E" in FIG. 43. As discussed above, proximal movement of sensor tube 176 effects proximal movement of sensor cylinder 178 and sensor link 182 in the direction indicated by arrow "E" in FIG. 43a to pivot locking member 83 counter-clockwise, as indicated by arrow "Y" in FIG. 43a, from a non-blocking position to a position blocking movement of actuation shaft 46.

Figure 45:
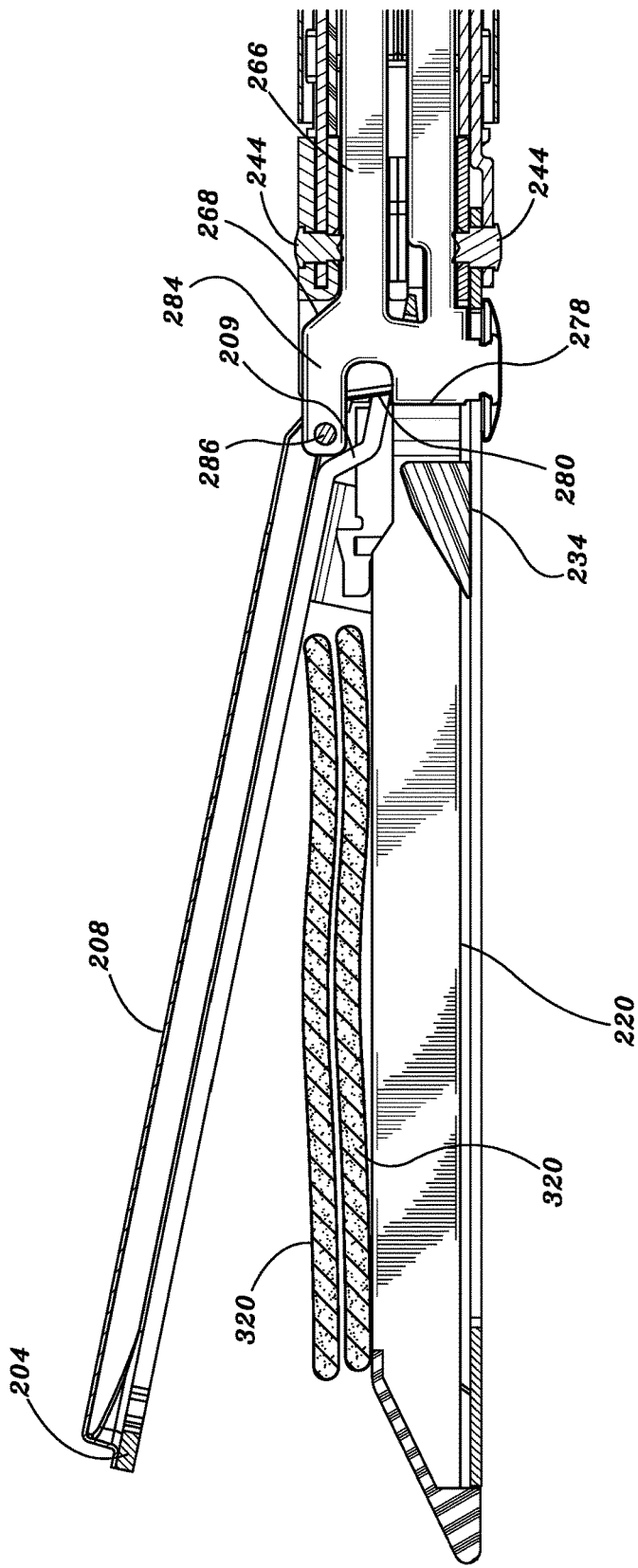
FIG. 45 is a side cross-sectional view of the distal end of the disposable loading unit of FIG. 1 with tissue positioned between the anvil and clamp assemblies.
Figure 46:
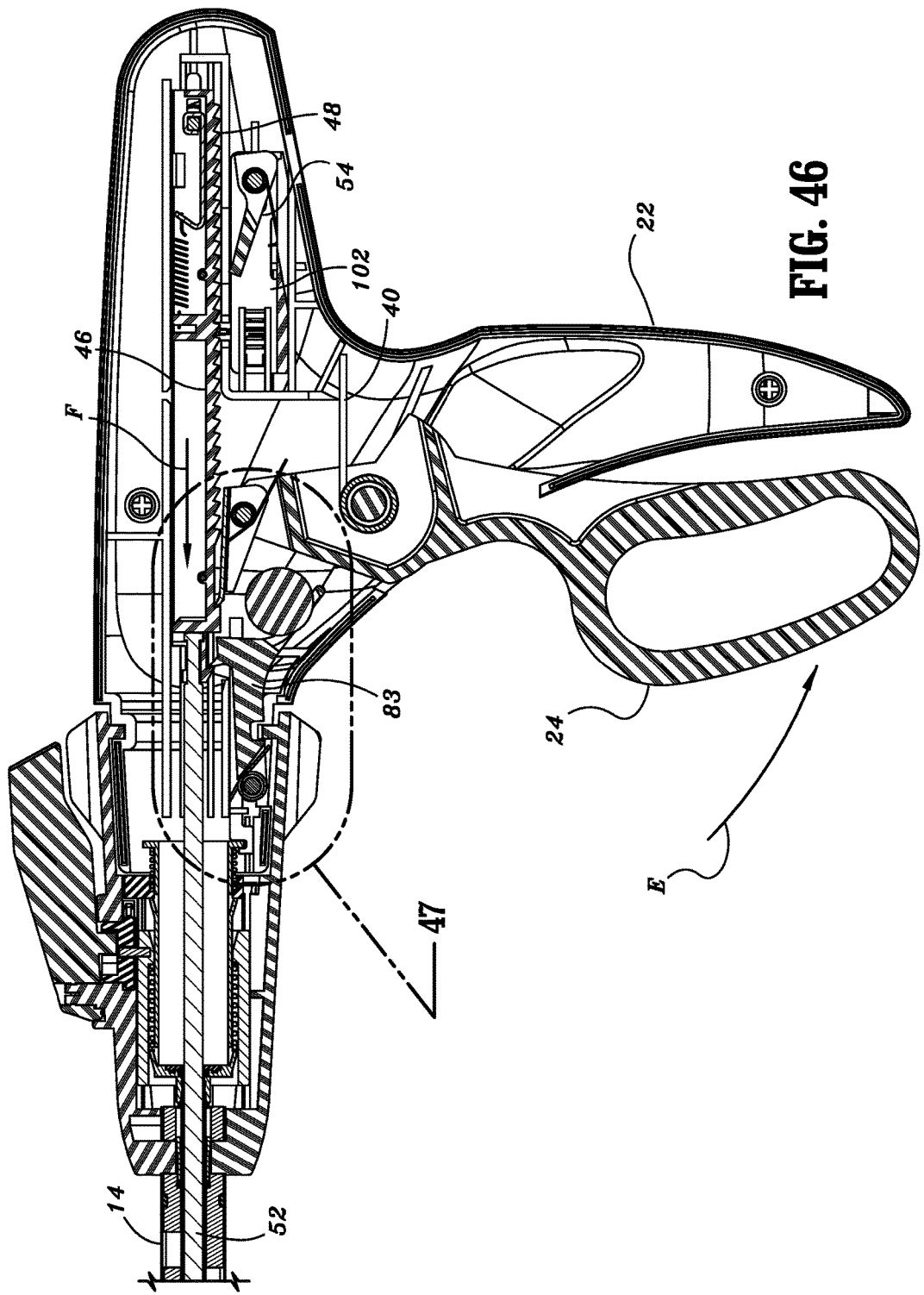
FIG. 46 is a side cross-sectional view of the handle assembly with the movable handle in an actuated position.
Figure 47:
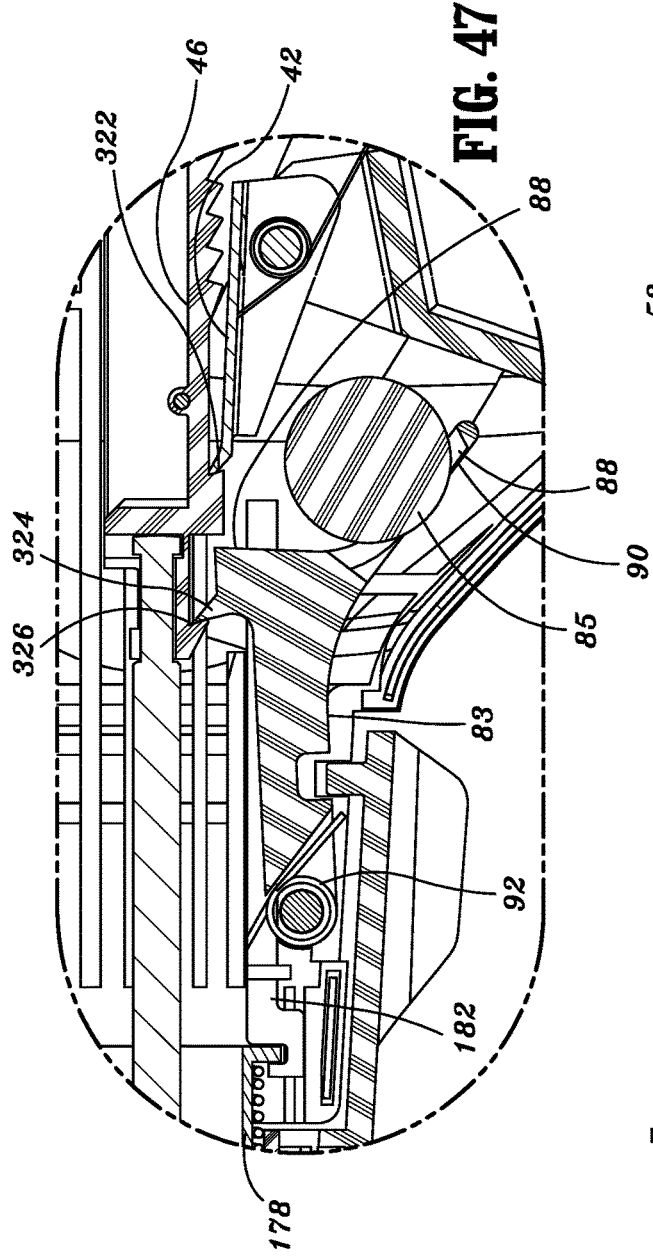
FIG. 47 is an enlarged view of the indicated area of detail shown in FIG. 46.
Figure 48:
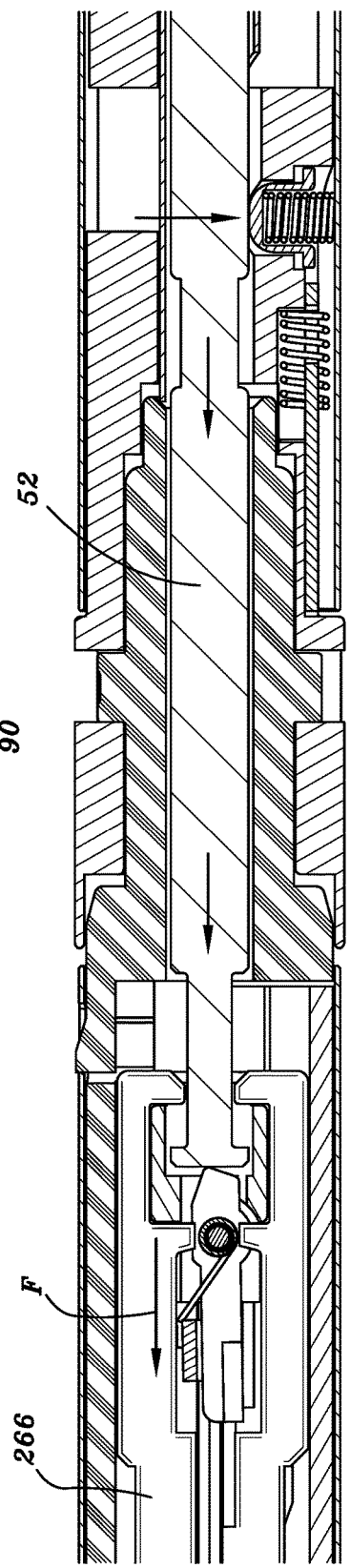
FIG. 48 is a cross-sectional view of the proximal end of the disposable loading unit of FIG. 19 and the distal end of the elongated body of the surgical instrument shown in FIG. 1 with the control rod in a partially advanced position.
Figure 49:
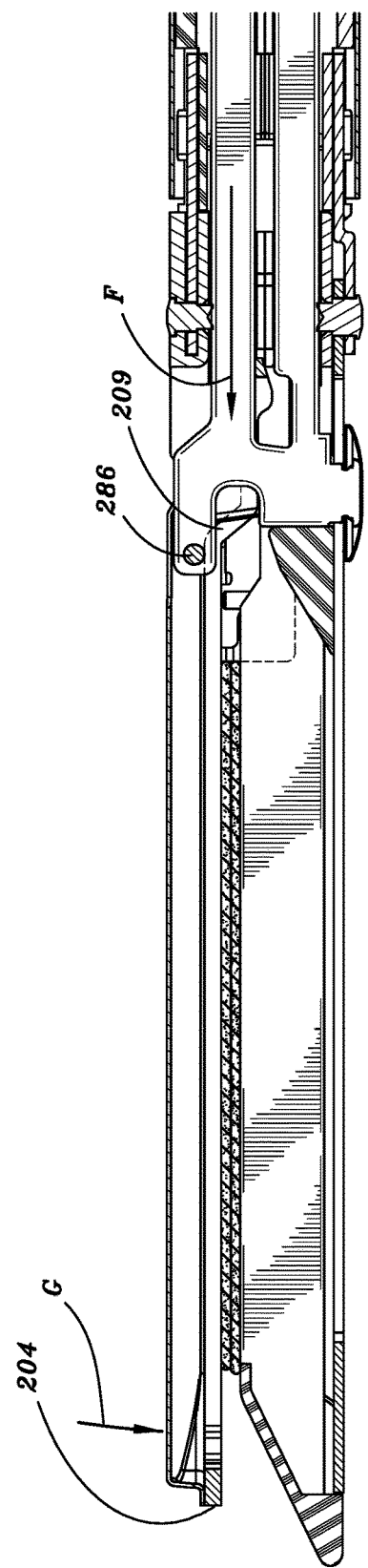
FIG. 49 is a cross-sectional view of the tool assembly of the surgical instrument shown in FIG. 1 positioned about tissue in the clamped position.

Referring to FIGS. 46-49, with a disposable loading unit attached to stapling instrument 10, tool assembly 17 can be positioned about tissue 320 (FIG. 45). To clamp tissue between anvil assembly 20 and cartridge assembly 18, stationary handle 24 is moved in the direction indicated by arrow "E" in FIG. 46 against the bias of torsion spring 40 to move driving pawl 42 into engagement with shoulder 322 on actuation shaft 46. Engagement between shoulder 322 and driving pawl 42 advances actuation shaft 46 and thus advances control rod 52 distally. Control rod 52 is connected at its distal end to axial drive assembly 212 (FIG. 48), including drive beam 266, such that distal movement of control rod 52 effects distal movement of drive beam 266 in the direction indicated by arrow "F" in FIGS. 48 and 49, moving cam roller 286 into engagement with cam surface 209 on anvil portion 204 to urge anvil portion 204 in the direction indicated by arrow "G" in FIG. 49. It is noted that one complete stroke of movable handle 24 advances actuation shaft 46 approximately 15 mm which is sufficient to clamp tissue during the first stroke but not to fire staples.

As discussed above with respect to the anti-reverse clutch mechanism, during the first (clamping) stroke of movable handle 24, slide plate 102 (FIG. 46) prevents locking pawl 54 from engaging toothed rack 48. To maintain actuation shaft 46 in its longitudinal position after handle 24 is released, an engagement member 324 (FIG. 47) is provided on locking member 83 to engage shoulder 326 on actuation shaft 46 and retain shaft 46 in its longitudinal position (See FIG. 47). Upon release of movable handle 24, drive pawl 42 moves over rack 48 as torsion spring 40 returns handle 24 to a position spaced from stationary handle 22. In this position, driving pawl 42 is urged into engagement with toothed rack 48 to retain actuation shaft 46 in its longitudinal fixed position.

In order to fire staples, movable handle 24 is actuated again, i.e., moved through another stroke. As discussed above, stapling apparatus 10 is capable of receiving disposable loading units having linear rows of staples of between about 30 mm and about 60 mm. Since each stroke of the movable handle 24 preferably advances actuation shaft 46 15 mm, and one stroke is required to clamp tissue, the movable handle must be actuated (n+1) strokes to fire staples, where n is the length of the linear rows of staples in the disposable loading unit attached to stapling instrument 10 divided by 15 mm.

Figure 50:
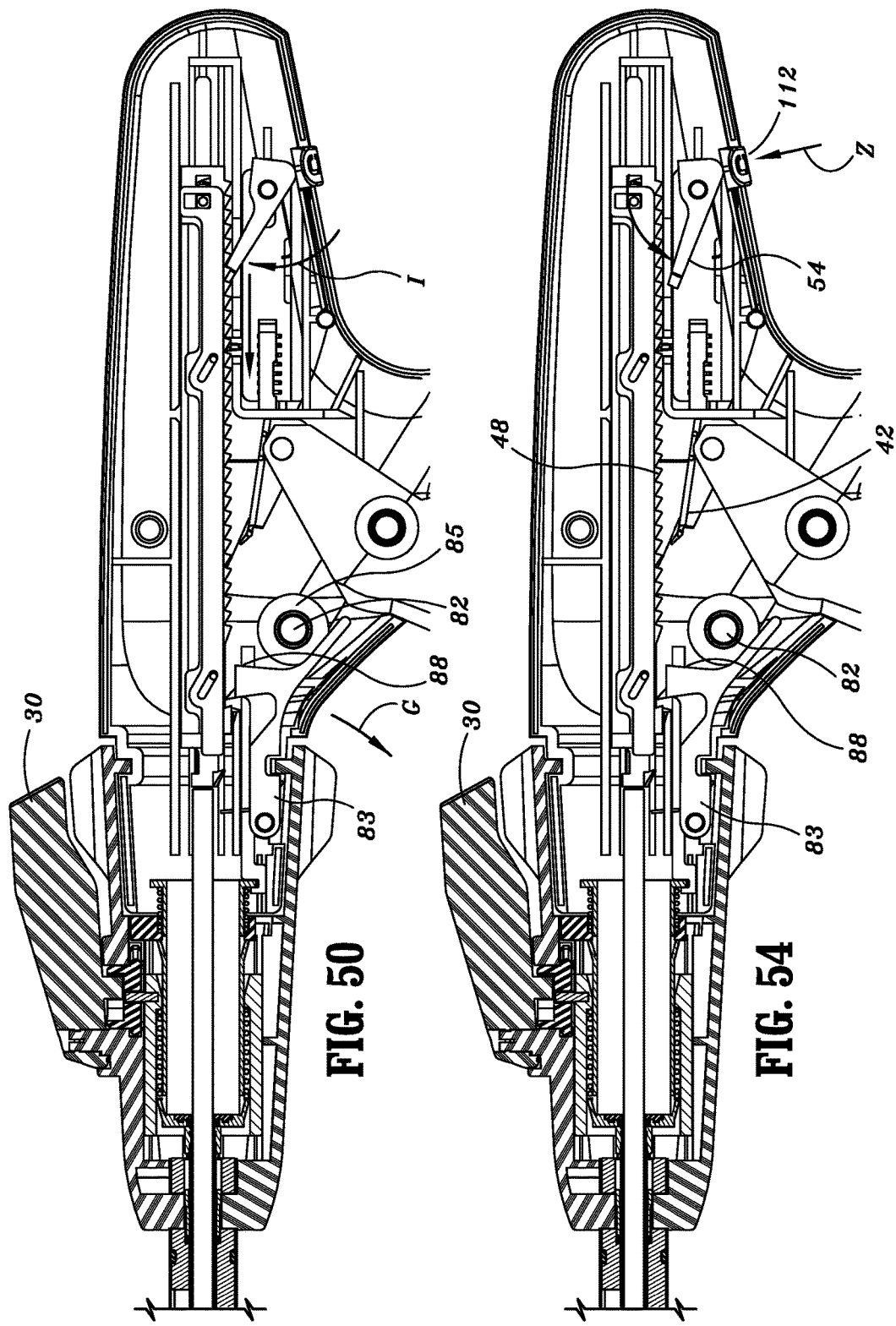
FIG. 50 is a cross-sectional view of the handle assembly of the stapling apparatus of FIG. 1 during the clamping stroke of the apparatus.
Figure 51:
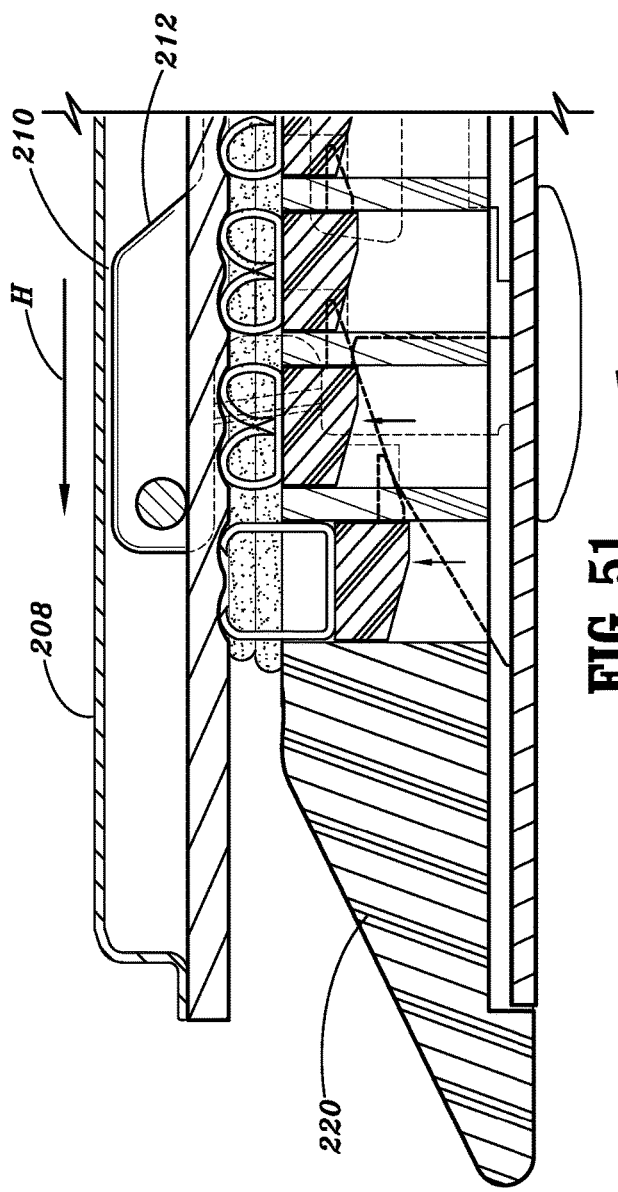
FIG. 51 is a side cross-sectional view of the distal end of the tool assembly of the stapling apparatus shown in FIG. 1 during firing of the apparatus.
Figure 52:
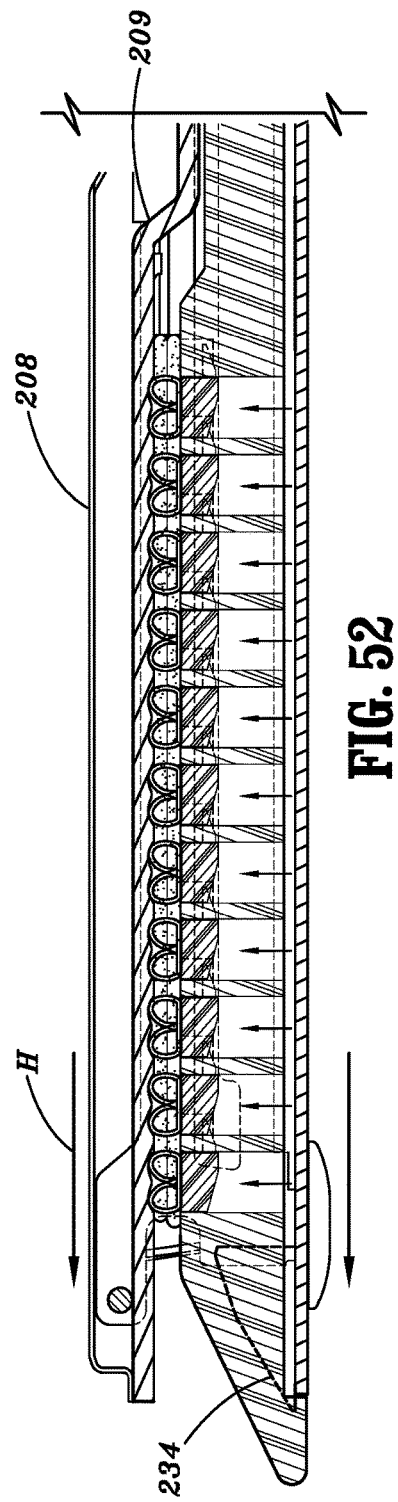
FIG. 52 is a side cross-sectional view of the distal end of the tool assembly of the stapling apparatus shown in FIG. 1 after firing of the apparatus.

Referring to FIG. 50, prior to being able to fire staples, firing lockout assembly 80 (FIG. 4) must be actuated to move locking surface 88 from its blocking position (FIG. 47) to a non-blocking position. This is accomplished by pressing down on plunger 82 to move camming surface 85 into engagement with sidewalls of slot 89 of locking member 83 to pivot locking member 83 in the direction indicated by arrow "G" in FIG. 50 (see also FIG. 5). Thereafter, movable handle 24 may be actuated an appropriate number of strokes to advance actuation shaft 46, and thus control rod 52 and drive beam 266, distally in the direction indicated by arrow "H" in FIGS. 51 and 52 to advance actuation sled 234 through staple cartridge 220 to effect ejection of staples. It is noted that after the first or clamping stroke of movable handle 54 (during the second stroke), slide 102 passes over locking pawl 54 allowing torsion spring 56 to move locking pawl 54 in the direction indicated by arrow "I" in FIG. 50 into engagement with toothed rack 48 to retain actuation shaft 46 in its longitudinal position.

Figure 53:
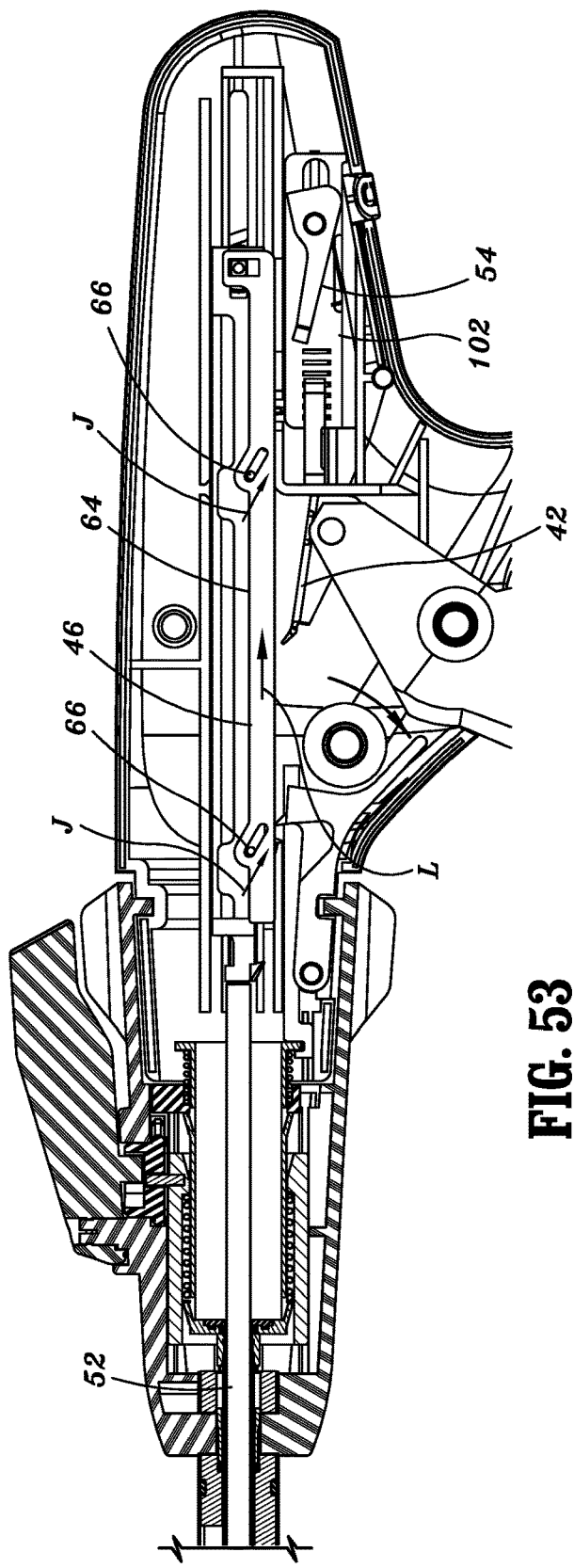
FIG. 53 is a side cross-sectional view of the handle assembly of the apparatus during retraction of the actuation shaft.

Referring to FIG. 53, to retract actuation shaft 46 and thus control rod 52 and drive member 266 after firing staples, retraction knobs 32 (see FIG. 1) are pulled proximally causing pins 66 to move release plate 64 in the direction indicated by arrow "J" in FIG. 53 over teeth 48 to disengage drive pawl 42 from engagement with teeth 48. As discussed above, with respect to the anti-reverse clutch mechanism, locking pawl 54 is urged by slide plate 102 out of engagement with toothed rack 48 (not shown) to permit actuation shaft 46 to be moved proximally, in the direction indicated by arrow "L", after drive pawl 42 is disengaged from teeth 48.

Referring to FIG. 54, in order to retract actuation shaft 46 prior to firing stapling apparatus, i.e., when locking pawl is currently engaged with toothed racked 48, emergency return button 112 is pushed in the direction indicated by arrow "Z" in FIG. 54 to disengage locking pawl 54 from toothed rack 48. Retraction knobs 32 (FIG. 1) must also be concurrently pulled rearwardly, as discussed above, to release drive pawl 42 from rack 48.

Figure 55:
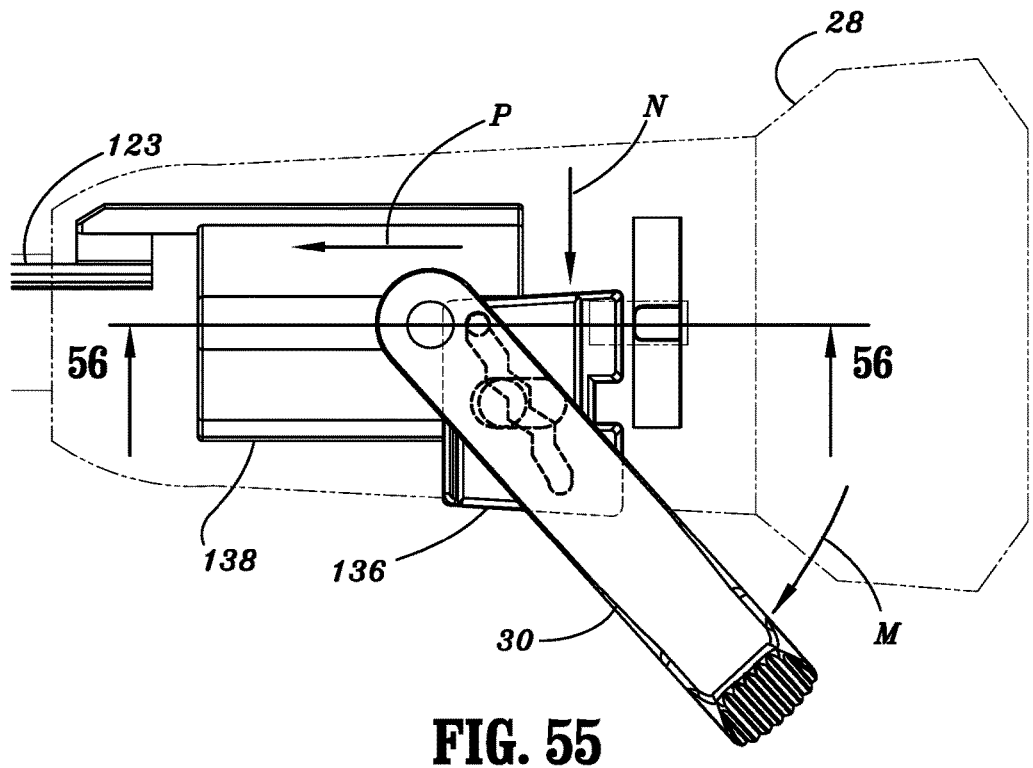
FIG. 55 is a top view of the articulation mechanism of the surgical instrument.
Figure 56:
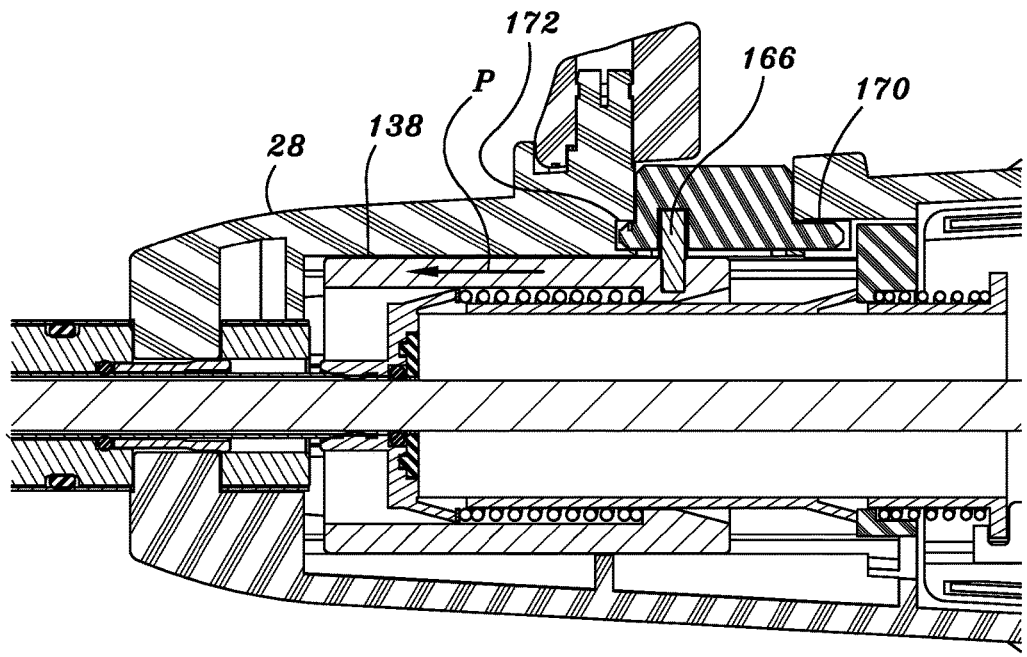
FIG. 56 is a side cross-sectional view of the articulation mechanism and rotation member of the surgical instrument shown in FIG. 1.

Referring to FIGS. 55-61, when an articulating disposable loading unit is secured to elongated body 14 and articulation lever 30 is pivoted in the direction indicated by arrow "M"

in FIG. 55, cam member 136 is moved transversely by projection 142 (FIG. 10) in the direction indicated by arrow "N" between flanges 170 and 172 of rotation knob 28. Since translation member 138 is prevented from rotating by ridges 156 (FIG. 13), pin 166, which is fixedly secured to translation member 138, is forced to move along stepped cam surface 148. Movement of pin 166 causes corresponding movement of translation member 138 in the direction indicated by arrow "P" in FIGS. 55 and 56 to advance first articulation link 123 in the distal direction. The distal end of first articulation link 123 engages the proximal end of second articulation link 256 (FIG. 42) which is connected to projection 262 on mounting assembly 202 to advance second link 256 in the direction indicated by arrow "Q" in FIG. 57. Projection 262 is laterally offset from pivot members 244, such that distal advancement of second articulation link 256 causes mounting assembly 202 and thus tool assembly 17 to pivot in the direction indicated by arrow "R" in FIGS. 57 and 58. Note in FIG. 59 that rotation member 28 can be rotated to rotate elongated body 14 about its longitudinal axis while tool assembly 17 is articulated.

An embodiment of the articulation of tool assembly 17 is illustrated in FIGS. 60-61. In this embodiment, articulation of tool assembly 17 occurs in the opposite direction to that described above. When second articulation link 256 is retracted by rotating articulation lever 30 in a counter-clockwise direction (not shown) as viewed in FIG. 55, pin 66 is forced to move proximally along stepped camming surface 148, moving translation member 138 and first articulation link 123 proximally. Movement of first articulation link 123 proximally, causes second articulation link 256 to move proximally as indicated by arrow "S" in FIG. 58, to rotate tool assembly 17 in a clockwise direction, as indicated by arrow "T" in FIG. 61. As can be appreciated, surgical instrument 10 can be configured such that proximal movement of first articulation link 123 causes tool assembly 17 to rotate in a counter-clockwise direction.

Referring to FIG. 12, movement of pin 166 (FIG. 9) between adjacent step portions 340 causes tool assembly 17 to articulate 22.5 degrees. Camming surface 148 includes five step portions 340. The third step portion corresponds to the non-articulated tool assembly position, whereas the first and the fifth step portions correspond to articulation of tool assembly 17 to forty-five degrees. Each step portion is flat to retain articulation lever 30 in a fixed position when pin 166 is engaged therewith.

Figure 39:
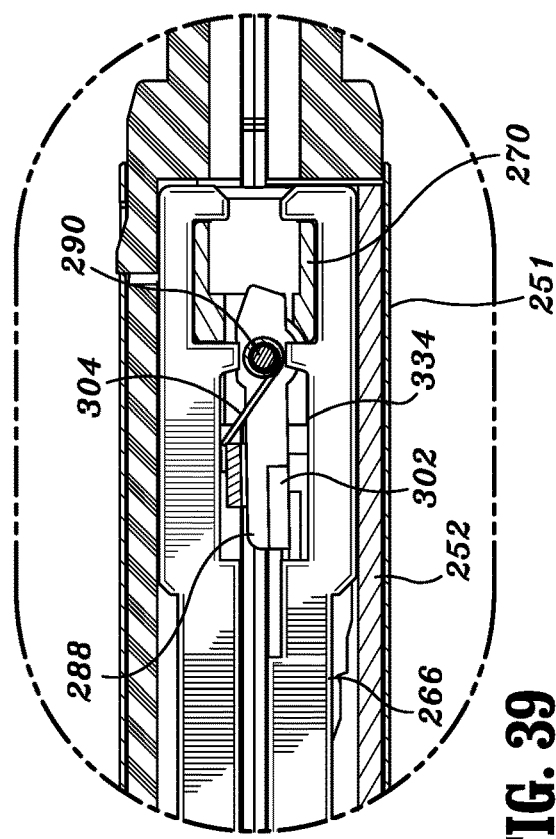
FIG. 39 is an enlarged view of the indicated area of detail shown in FIG. 38.
Figure 40:
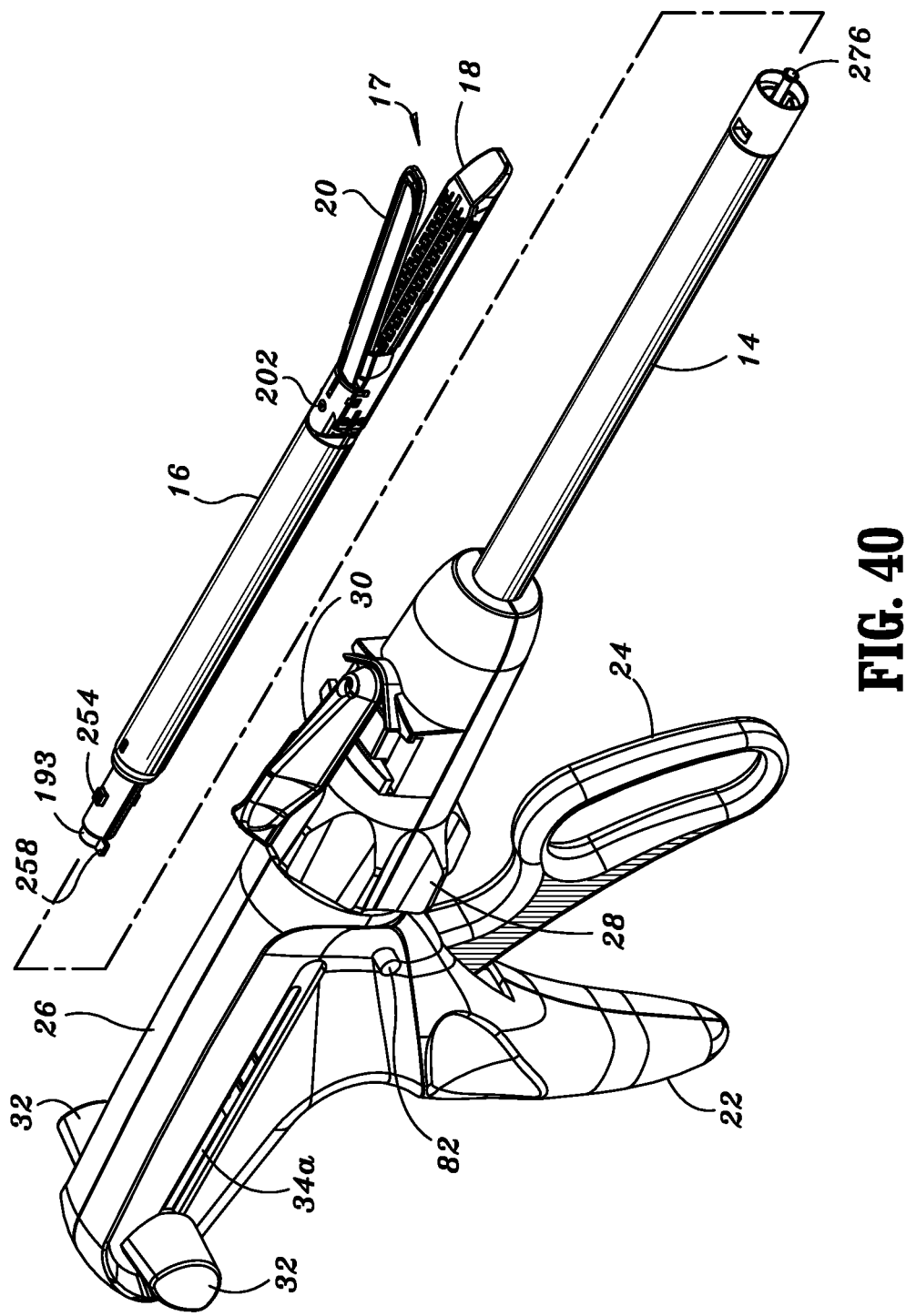
FIG. 40 is a perspective view of the surgical instrument shown in FIG. 1 with the disposable loading unit of FIG. 19 detached from the elongated body.

Referring now to FIGS. 37, 39, 62 and 63, the sequence of lockout operation will be described in detail. In FIG. 39, lockout device 288 is shown in its preferred position with horizontal cams 300 and 302 resting on top of projections 330 formed in the sidewalls of lower housing half 252 (FIG. 37). In this position, locking device 288 is held up out of alignment with projection 332 formed in the bottom surface of lower housing half 252, and web 298 is in longitudinal juxtaposition with shelf 334 defined in drive beam 266. This configuration permits the anvil 20 (FIG. 38) to be opened and repositioned onto the tissue to be stapled until the surgeon is satisfied with the position without activating locking device 288 to disable the disposable loading unit 16.

Figure 62:
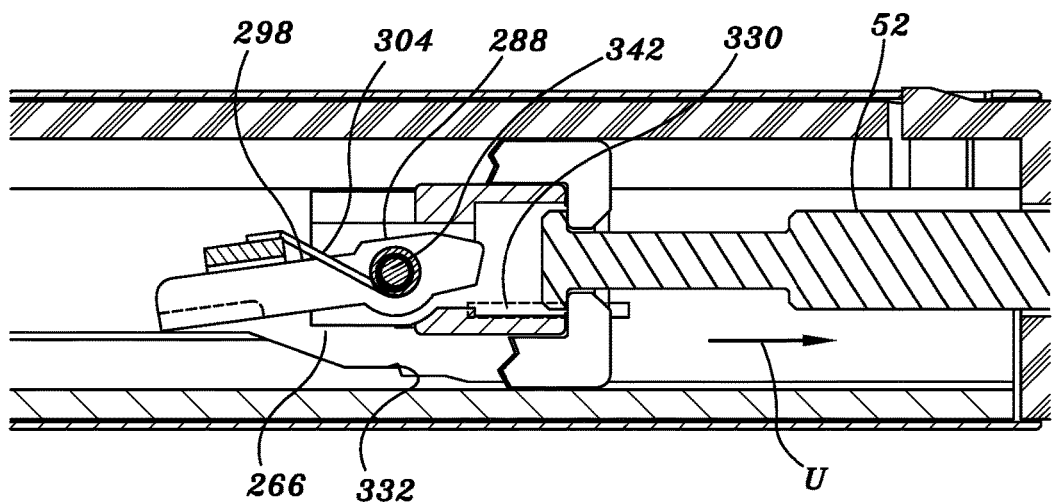
FIG. 62 is a partial cross-sectional view of a portion of the disposable loading unit during retraction of the locking device.
Figure 63:
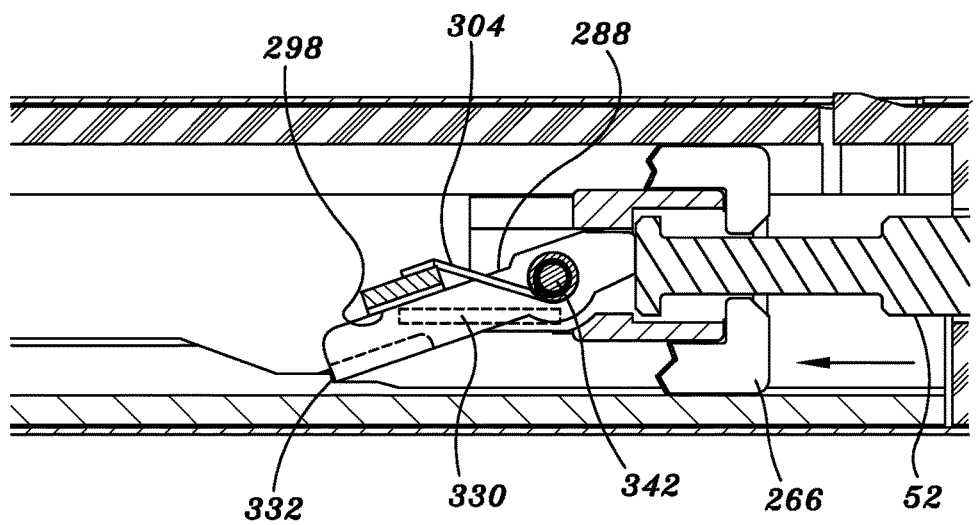
FIG. 63 is a partial cross-sectional view of a portion of the disposable loading unit with the locking device in the locked position.

As shown in FIG. 62, upon distal movement of drive beam 266, locking device 288 rides off of projections 330 (not shown) and is biased into engagement with base lower housing half 252 by spring 304, distal to projection 332. Locking device 288 remains in this configuration throughout firing of the apparatus.

Upon retraction of the drive beam 266 in the direction indicated by arrow "U" in FIG. 62, locking device 288 passes under projections 330 and rides over projection 332 until the distal-most portion of locking device 288 is proximal to projection 332. Spring 304 biases locking device 288 into juxtaposed alignment with projection 332, effectively disabling the disposable loading unit. If an attempt is made to reactuate the apparatus, the control rod 52 will abut a proximal end surface of locking device 288 which surface is diagonally sloped to impart a moment about pivot pin 342 such that the distal end of locking device 288 is rotationally urged into contact with projection 332. Continued distal force in the direction indicated by arrow "W" in FIG. 63, will only serve to increase the moment applied to the locking device thus the locking device will abut projection 332 and inhibit distal movement of the control rod 52.

Referring again to FIGS. 41-44, the disabled or locked disposable loading unit can be removed from the distal end of elongated body 14 by rotating disposable loading unit 16 in the direction opposite to the direction indicated by arrow "B" in FIGS. 41, 42 and 44, to disengage hook portion 258 of second articulation link 256 from finger 164 of first articulation link 123, and to disengage nubs 254 from within channel 314 of elongated body 14. After rotation, disposable loading unit 16 can be slid in the direction opposite to that indicated by arrow "A" in FIG. 41 to detach body 14 from disposable loading unit 16. Subsequently, additional articulating and/or non-articulating disposable loading units can be secured to the distal end of elongated body, as described above, to perform additional surgical stapling and/or cutting procedures. As discussed above, each disposable loading unit may include linear rows of staples which vary from about 30 mm to about 60 mm.

It will be understood that various modifications may be made to the embodiments disclosed herein. For example, the stapling apparatus need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

The invention claimed is:

1. A method of operating a surgical instrument, comprising:
   providing a surgical instrument including a tool assembly and an articulation mechanism,
   the articulation mechanism including:
   a lower clutch having a plurality of recesses; and
   an upper clutch having a plurality of protrusions for engaging at least one of the recesses of the plurality of recesses of the lower clutch; and
   engaging a first protrusion of the plurality of protrusions of the upper clutch with a first recess of the plurality of recesses of the lower clutch, wherein engagement between the first protrusion of the plurality of protrusions and the first recess of the plurality of recesses retains the tool assembly in a first position, the first recess of the plurality of recesses being larger than other recesses of the plurality of recesses.

2. The method according to claim 1, further including biasing the upper clutch towards the lower clutch.

3. The method according to claim 1, further including moving an articulation lever of the articulation mechanism in a rotary fashion to cause corresponding movement of the upper clutch.

4. The method according to claim 1, wherein engagement between the first protrusion of the plurality of protrusions and the first recess of the plurality of recesses retains the tool assembly in a non-articulated position.

5. The method according to claim 1, wherein the lower clutch is at least partially positionable within a receptacle of the surgical instrument.

6. The method according to claim 5, further comprising maintaining the position of the lower clutch along a rotation axis with respect the receptacle of the surgical instrument while rotating the upper clutch about the rotation axis with respect to the lower clutch and with respect to the receptacle.

7. The method according to claim 5, wherein the lower clutch is fixedly positioned with respect to the receptacle.

8. A method of operating a surgical instrument, comprising:
providing a surgical instrument including a tool assembly and an articulation mechanism,
the articulation mechanism including:
a first portion including serrations, a first pair of adjacent serrations being separated by a first angle, a second pair of adjacent serrations being separated by a second angle, the first angle being different from the second angle; and
a second portion including a projection, the projection of the second portion being positioned to engage one of the serrations of the first portion,
engaging the projection of the second portion with one of the serrations of the first portion to retain the tool assembly in a fixed position.

9. The method according to claim 8, further comprising biasing the second portion toward the first portion.

* * * * *